United States Patent
Latil De Ros et al.

(10) Patent No.: US 11,279,962 B2
(45) Date of Patent: Mar. 22, 2022

(54) CHITIN AND CHITOSAN PRODUCING METHODS

(71) Applicant: GREENALTECH, S.L., Barcelona (ES)

(72) Inventors: Derek Georges Latil De Ros, Girona (ES); María Teresa López Cerro, Islles Balears (ES); Eugenia Ruiz Canovas, Granollers-Barcelona (ES); Olga Durany Turk, Barcelona (ES); Jordi Segura De Yebra, Barcelona (ES); Jaume Mercadé Roca, Barcelona (ES); Daniel Pérez Reyes, Barcelona (ES); Xavier Álvarez Mico, Terrassa (ES)

(73) Assignee: Algaktiv, S.L., Parc Cientific de Barcelona (ES)

( * ) Notice: Subject to any disclaimer, the term of this patent is extended or adjusted under 35 U.S.C. 154(b) by 595 days.

(21) Appl. No.: 15/537,247

(22) PCT Filed: Dec. 16, 2015

(86) PCT No.: PCT/EP2015/079993
§ 371 (c)(1),
(2) Date: Jun. 16, 2017

(87) PCT Pub. No.: WO2016/096986
PCT Pub. Date: Jun. 23, 2016

(65) Prior Publication Data
US 2017/0342453 A1 Nov. 30, 2017

(30) Foreign Application Priority Data
Dec. 16, 2014 (EP) .................................. 14382526

(51) Int. Cl.
| | | |
|---|---|---|
| *A61K 36/02* | (2006.01) | |
| *A61K 36/03* | (2006.01) | |
| *A61K 36/04* | (2006.01) | |
| *A61K 36/05* | (2006.01) | |
| *C12P 19/26* | (2006.01) | |
| *A61K 31/722* | (2006.01) | |
| *C08B 37/08* | (2006.01) | |
| *C08B 37/00* | (2006.01) | |
| *C12P 19/04* | (2006.01) | |

(52) U.S. Cl.
CPC ............ *C12P 19/26* (2013.01); *A61K 31/722* (2013.01); *A61K 36/05* (2013.01); *C08B 37/0003* (2013.01); *C08B 37/003* (2013.01); *C12P 19/04* (2013.01)

(58) Field of Classification Search
None
See application file for complete search history.

(56) References Cited

U.S. PATENT DOCUMENTS

| | | |
|---|---|---|
| 2,795,579 A | 6/1957 | Doczi |
| 5,622,834 A | 4/1997 | Vournakis et al. |
| 5,623,064 A | 4/1997 | Vournakis et al. |
| 5,686,115 A | 11/1997 | Vournakis et al. |
| 5,846,952 A | 12/1998 | Vournakis et al. |
| 6,551,596 B2 | 4/2003 | Kralovec |
| 6,649,599 B2 | 11/2003 | Vournakis et al. |
| 6,686,342 B2 | 2/2004 | Vournakis et al. |
| 6,977,076 B2 | 12/2005 | Kralovec |
| 7,205,284 B2 | 4/2007 | Pasco et al. |
| 8,277,849 B2 | 10/2012 | Dillon et al. |
| 8,835,528 B2 | 9/2014 | Pravata |
| 2009/0004699 A1 | 1/2009 | Tsuji et al. |
| 2012/0164072 A1* | 6/2012 | Linder ............ A61P 25/28 424/1.69 |
| 2012/0244603 A1* | 9/2012 | Blank ............ A01G 33/00 435/257.1 |
| 2013/0337067 A1* | 12/2013 | Prakash ............ A61K 48/0041 424/489 |
| 2014/0273176 A1* | 9/2014 | Fleischer ............ C08B 37/003 435/261 |
| 2015/0174153 A1* | 6/2015 | Nothias ............ A61L 27/20 424/422 |

FOREIGN PATENT DOCUMENTS

| | | |
|---|---|---|
| CA | 2 372 026 A1 | 6/1995 |
| CN | 103108638 A | 5/2013 |
| CN | 103519458 A | 1/2014 |

(Continued)

OTHER PUBLICATIONS

Anitha, A. et al., "Chitin and chitosan in selected biomedical applications", Progress in Polymer Science, vol. 39, 2014, pp. 1644-1667.
Bokura, H. and Kobayashi, S. et al., "Chitosan decreases total cholesterol in women: a randomized, double-blind, placebo-controlled trial", European Journal of Clinical Nutrition, vol. 57, 2003, pp. 721-725.
Boucard, N. et al., "The use of physical hydrogels of chitosan for skin regeneration following third-degree burns", Biomaterials, vol. 28, 2007, pp. 3478-3488.
Dai, Y. et al., "Chitosan preparations for wounds and burns: antimicrobial and wound-healing effects", Expert Rev. Anti Infect Ther, vol. 9, No. 7, 2011, pp. 857-879.

(Continued)

*Primary Examiner* — Michael Barker
*Assistant Examiner* — Randall O Winston
(74) *Attorney, Agent, or Firm* — Gary J. Gershik; Amster Rothstein & Ebenstein LLP

(57) ABSTRACT

The invention relates to the field of polymer production, in particular to the production of chitin and chitosan from microalgae belonging to the phylum Haptophyta to the phylum Chlorophyta, or to the phylum Heterokontophyta, particularly from microalgae of the genus *Isochrysis, Chlorella, Bracteacoccus, Chlorococcum, Scenedesmns, Desmodesmus, Haematococcus, Thalassiosira* and *Nannochloropsis*, as well as to microalgal extracts thereof and their uses.

14 Claims, 4 Drawing Sheets

(56) References Cited

FOREIGN PATENT DOCUMENTS

| EP | 1 259 564 | | 11/2002 |
|---|---|---|---|
| EP | 1 452 546 | A2 | 9/2004 |
| EP | 1 939 302 | A1 | 7/2008 |
| KR | 2014094775 | A * | 7/2014 |
| WO | WO9620730 | A1 * | 7/1996 |
| WO | 2004/003175 | A2 | 1/2004 |
| WO | 2010/007332 | A2 | 1/2010 |
| WO | 2010/111710 | A1 | 9/2010 |
| WO | 2015/092030 | A1 | 6/2015 |

OTHER PUBLICATIONS

Dass, C.R. and Choong, P.F.M., et al., "The use of chitosan formulations in cancer therapy", Journal of Microencapsulation, vol. 25, No. 4, 2008, pp. 275-279.
Francis Suh, J.-K. and Matthew, H.W.T., et al., "Application of chitosan-based polysaccharide biomaterials in cartilage tissue engineering; a review", Biomaterials, vol. 21, 2000, pp. 2589-2598.
Jing et al., "Effect of Chitosan on Renal Function in Patients with Chronic Renal Failure", J. Pharm. Pharmacol., vol. 49, 1997, pp. 721-723.
Kim et al., "Inhibitory Effect of Water-Soluble Chitosan on TNF-α and IL-8 Secretion from HMC-1 Cells", Immunopharmacology and Immunotoxicology, vol. 26, No. 3, 2004, pp. 401-409.
Libreros, S. et al., "Induction of proinflammatory mediators by CHI3L1 is reduced by chitin treatment: decreased tumor metastasis in a breast cancer model", Int. J. Cancer, vol. 131, No. 2, 2012 pp. 377-386.
Nadapdap, T.P et al., "Influence of Chitosan from Shrimp Skin to Quality and Quantity of Sperm of Albino Rats after Administration of Lead", Andrology, vol. 3, 2014, doi: 10.4172/2167-0250.1000114.
Okamoto, Y. et al., "Effects of chitin and chitosan on blood coagulation", Carbohydrate Polymers., vol. 53, 2003, pp. 337-342.
Pavis, H. et al., "Pilot Study of Nasal Morphine-Chitosan for the Relief of Breakthrough Pain in Patients With Cancer", Journal of Pain and Symptom Management, vol. 24, No. 6, 2002, pp. 598-602.
Venkatesan, J. and Kim, Se-Kwan et al., "Chitosan Composites for Bone Tissue Engineering-An Overview", Marine Drugs, vol. 8, 2010, pp. 2252-2266.
Vo, J. et al., "Neoadjuvant immunotherapy with chitosan and interleukin-12 to control breast cancer metastasis", OncoImmunology, vol. 3, DOI: 10.4161/21624011.2014.968001, 2014, pp. e968001-1 to e968001-10.
Abdou, et al., "Extraction and characterization of chitin and chitosan from local sources", Biores. Tech., vol. 99, 2008, pp. 1359-1367.
Ali et al., "Characterization of a chitinase gene encoded by virus-sensitive Chlorella strains and expressed during virus infection", Arab J. Biotech, vol. 10, No. 1, 2007, pp. 81-96.
Benjaminson, "Conjugates of chitinase with fluorescein isothiocyanate or lissamine rhodamine as specific stains for chitin in situ", Stain Technology, vol. 44, No. 1, 1969, pp. 27-31.
Blanc et al., "The *Chlorella variabilis* NC64A genome reveals adaptation to photosymbiosis, coevolution with viruses, and cryptic sex", The Plant Cell, vol. 22, 2010, pp. 2943-2955.
Blumreisinger, et al., "Cell wall composition and chlorococcal algae", Phytochemistry, vol. 22, No. 7, 1983, pp. 1603-1604.
Brunner et al., "Chitin-based organic networks: an integral part of cell wall biosilica in the diatom *Thalassiosira pseudonana*", Angew. Chem. Int. Ed., vol. 48, 2009, pp. 9724-9727.
Burczyk et al., "Comparison of nitrogen content amino acid composition and glucosamine content of cell walls of various chlorococcalean algae", Phytochemistry, vol. 51, 1991, pp. 491-497.
Campana-Filho et al., "Extraction, structures and properties of α- and β-chitin", Quim. Nova, vol. 30, 2007, pp. 644-650 (Including English Translation).

Cheba, "Chitin and chitosan: marine bipolymers with unique properties and versatile applications", Global Journal of Biotechnology & Biochemistry, vol. 6, No. 3, 2011 pp. 149-153.
Cheirsilp et al., "Enhanced growth and lipid production of microalgae under mixotrophic culture condition: Effect of light intesity, glucose concentration and fed-batch cultivation condition: Effect of light intensity, glucose concentration and fed-batch cultivation", Bioresource Technology, vol. 110, 2012, pp. 510-516.
Chrétiennot-Dinet et al., "The chitinous nature of filaments ejected by phaeocystis (prymnesiophyceae)", Journal of Phycol., vol. 33, 1997, pp. 666-672.
Chuchird et al., "Digestion of chlorella cells by chlorovirus- encoded polysaccharide degrading enzymes", Microbes and Environment, vol. 16, No. 4, 2001, pp. 206-212.
Dai et al., "Chitosan preparations for wounds and burns: antimicrobial and wound-healing effects", Expert Rev. Anti Infect Ther, vol. 9, No. 7, 2011, pp. 857-879.
Durkin et al., "Chitin in diatoms and its association with the cell wallΔ", Eukaryotic Cell, vol. 8, No. 7, 2009, pp. 1038-1050.
Dutta et al., "Chitin and Chitosan: chemistry, properties and applications", Journal of Scientific & Industrial Research, vol. 63, 2004, pp. 20-31.
Fai et al., "Physico-chemical characteristics and functional properties of chitin and chitosan produced by *Mucor circinelloides* using yam bean as substrate", Molecules, vol. 16, 2011, pp. 7143-7154.
Fuenzalida et al., "Affinity protein-based FRET tools for cellular tracking of chitosan nanoparticles and determination of the polymer degree of acetylation", Biomacromolecules, 2014, pp. A-H.
Galun et al., "Hyphal walls of isolated lichen fungi", Arch. of Microbiol., vol. 108, 1976, pp. 9-16.
Gerken et al., "Enzymatic cell wall degradation of *Chlorella vulgaris* and other microalgae for biofuels production", Planta vol. 237, 2013, pp. 239-253.
Guarnieri et al., "Examination of triaclyglycerol biosynthetic pathways via de novo transcriptomic and proteomic analyses in an unsequenced microalga", Plos One, vol. 6, No. 10, 2011, pp. 1-13.
Guillard, R.R.L. and Ryther, J.H., "Studies of marine planktonic diatoms I. cyclotella nana hustedt, and detonula confervacea (cleve) gran[1].", Canadian Journal of Microbiology, vol. 8, 1962, pp. 229-239.
Hayes et al., "Mining marine shellfish wastes for bioactive molecules: chitin and chiotsan—Part B: Applications", Biotechnol. Journal, vol. 3, 2008, pp. 878-889.
Herasimenka et al., "A selective assay to detect chitin and biologically active nano-machineries for chitin-biosynthesis with their intrinsic chitin-synthase molecules", International Journal of Molecular Sciences, vol. 11, 2010, pp. 3122-3137.
Herth et al., "Chitinous fibrils in the lorica of the flagellate chrysophyte *Poteriochromonas stipitata*", The Journal of Cell Biology, vol. 73, 1977, pp. 311-321.
Hirano et al., "An improved method for the prevention of colloidal chitin by using methanesulfonic acid", Agric. Biol. Chem., vol. 52, No. 8, 1988, pp. 2111-2112.
Hirano et al., "Classification of chitosanases by hydrolytic specificity toward $N^1$, $N^4$-diacetylchitohexaose", Biosci. Biotechnol. Biochem., vol. 76, No. 10, 2012, pp. 1932-1937.
Hoell, et al., "Structure and function of enzymes acting on chitin and chitosan", Biotechnology and Genetic Engineering Reviews 2010, vol. 27, pp. 331-366.
Horisberger et al., "Localization of α-galactomannan and of wheat germ agglutinin receptors in *Schizosaccharomyces pombe*", Archives of Microbiology, vol. 119, 1978, pp. 107-111.
Huang, Wen-Can, and Kim, Jong-Duk, "Cationic surfactant-based method for simultaneous harvesting and cell disruption of a microalgal biomass", Bioresource Technology, vol. 149, 2013, pp. 579-581.
Ito et al., "Anti-ulcer effects of chitin and chitosan, healthy foods, in rats", Jpn. J. Pharmacol., vol. 82, 2000, pp. 218-225.
Kapaun, E., and Reisser, W., "A chitin-like glycan in the cell wall of a *Chlorella* sp. (chlorococcales, chlorophyceae)", Planta, vol. 197, No. 4, 1995, pp. 577-582.

(56) References Cited

OTHER PUBLICATIONS

Kaur S., and Dhillon, G.S., "The versatile biopolymer chitosan: potential sources, evalutation of extraction methods and applications". Critical Reviews in Microbiology, vol. 40, No. 2, 2014, pp. 155-175.
Keller M.D., and Selvin R.C., "Media for the culture of oceanic ultraphytoplankton[1,2]", J. Phycol. vol. 23, 1987, pp. 633-638.
Knorr, D., and Klein, J., "Production and conversion of chitosan with cultures of mucor rouxxi or phycomyces blakesleeanus". Biotechnology Letters, vol. 8, No. 10, 1986, pp. 691-694.
Liang et al., "Biomass and lipid productivities of *Chlorella vulgaris* under autotrophic, heterotrophic and mixotrophic growth conditions", Biotechnol. Lett., vol. 31, 2009, pp. 1043-1049.
Ma et al., "A novel chitosan-collagen-based hydrogel for use as a dermal filler: initial in vitro and in vivo investigations", J. of Mater. Chem. B., vol. 2, 2014, pp. 2749-2763.
Marques et al., "Animal model of impant capsular contracture: effects of chitosan", Aesthetic Surgery Journal, vol. 31, No. 5, 2011, pp. 540-550.
Mayakrishnan et al., "Cardioprotective activity of polysaccharides derived from marine algae: an overview", Trends in Food Science & Technology, vol. 30, 2013, pp. 98-104.
Miranda, C., and Lizárraga, P., "Is chitosan a new panacea? Areas of application", Chapter 1, 2012, pp. 3-46.
Nampally et al., "Fusion of a novel genetically engineered chitosan affinity protein and green fluorescent protein for specific detection of chitosan in vitro and in situ", Applied and Environmental Microbiology, vol. 78, No. 9, 2012, pp. 3114-3119.
Neiderhofer, A., and Müller, B.W., "A method for direct preparation of chitosan with low molecular weight from fungi", European Journal of Pharmaceutics and Biopharmaceutics, vol. 57, 2004, pp. 101-105.
Nêmcová, Y., "Detection of cell wall structural polysaccharides by cellulase-gold and chitinase-gold complexes", Czech Phycology, vol. 3, 2003, pp. 31-36.
N.N., "A promising genus for biofuel productions with chlorella microalgae genome", PhysOrg Laboratoire Information Genomique et Structurale, CNRS, 2010, pp. 1-3.
Nwe, N. and Stevens, W.F., "Production of fungal chitosan by solid substrate fermentation followed by enzymatic extraction", Biotechnology Letters, vol. 24, 2002, pp. 131-134.
Ogawa et al., "Crystal analysis and high-resolution imaging of microfibrillar α-chitin from *Phaeocystis*", Journal of Structural Biology, vol. 171, 2010, pp. 111-116.
Ogawa et al., "Infrared study on deuteration of highly-crystalline chitin", Carbohydrate Polymers, vol. 90, 2012, pp. 650-657.
Perez-Garcia et al., "Heterotrophic cultures of microalgae: Metabolism and potential products", Water Research, vol. 45, 2011, pp. 11-36.
Pochanavanich, P., and Suntornsuk, W., "Fungal chitosan production and its characterization", Letters in Applied Microbiology, vol. 35, 2002, pp. 17-21.
Pombert et al, "The chloroplast genome sequence of the green alga pseudendoclonium akinetum (ulvophyceae) reveals unusual structural features and new insights into the branching order of chlorophyte lineages", Mol. Biol. Evol. vol. 22, No. 9, 2005, pp. 1903-1918.
Pombert et al., "A lack of parasitic reduction in the obligate parasitic green alga *Helicosporidium*", Plos Genetics, 2014, vol. 10, No. 5, pp. 1-13.
Retallack G.J., "Acritarch evidence for an ediacaran adaptive radiation of fungi", Botanica Pacifica, vol. 4, No. 2, 2015, pp. 19-33.
Rinaudo, M., "Chitin and chitosan: properties and applications", Progress in Polymer Science vol. 31, 2006, pp. 603-632.
Roberts G.A.F.,"Thirty years of progress in chitin and chitosan", Progress on chemistry and application of chitin and its, vol. XIII, 2008, pp. 7-15.
Saimoto et al., "Biodegradation of chitin with enzymes and vital components", Macromol. Symp., vol. 120, 1997, pp. 11-18.
Segneanu et al., "Biomass extraction methods", Chapter 15, 2013, pp. 389-400.
Smucker, R.A. and Dawson, R., "Products of photosynthesis by marine phytoplankton: chitin in TCA "protein" precipitates*", Journal of Experimental Marine Biology And Ecology, vol. 104, 1986, pp. 143-152.
Solov'eva et al., "Marine compounds with therapeutic potential in gram-negative sepsis", Marine Drugs, vol. 11, 2013, pp. 2216-2229.
Struszczyk, "Herstellung von Chitosan und einige Anwendungen", Thesis, University of Potsdam, 2000, p. 1 and 16, (XP-002738346).
Sugimoto et al., "vAL-1, a novel polysaccharide lyase encoded by chlorovirus CVK2", FEBS Letters, vol. 559, 2004, pp. 51-56.
Takeda, H., "Sugar composition of the cell wall and the taxonomy of *Chlorella* (chlorophyceae)[1]", J. Phycol., vol. 27, 1991, pp. 224-232.
Wang et al., "A new green technology for direct production of low molecular weight chitosan", Carbohydrate Polymers, vol. 74, 2008, pp. 127-132.
Xia et al., "Biological activities of chitosan and chitooligosaccharides", Food Hydrocolloids, vol. 25, 2011, pp. 170-179.
Yogeshkumar et al., "Chitosan and its applications: a review of literature", International Journal of Research in Pharmaceutical and Biomedical Sciences, vol. 4, No. 1, 2013, pp. 312-331.
International Search Report issued by the International Searching Authority (ISA/O.E.P.M.) dated Mar. 9, 2016 in connection with International Application No. PCT/EP2015/079993.
Brunner et al., "Chitin-based organic networks: An integral part of cell wall biosilica in the diatom Thalassiosira pseudonana", Angewandte Chemie International Edition, vol. 48, 2009, pp. 9724-9727.
Campana-Filho et al., "Extracão, estruturas e propriedades de alpha-e beta-quitina", Quimica Nova, vol. 30, 2007, pp. 644-650.
Chrétiennot-Dinet et al., "The chitinous nature of filaments ejected by Phaeocystis (Prymnesiophyceae)", Journal of Phycology, vol. 33, 1997, pp. 666-672.
Guarnieri et al., "Examination of triacylglycerol biosynthetic pathways via de novo transcriptomic and proteomic analyses in an unsequenced microalga", Plos One, vol. 6, 2011, pp. 1-13.
Nêmcová, "Detection of cell wall structural polysaccharides by cellulose-gold and chitinase-gold complexes", Czech Phycology, Olomouc, vol. 3, 2003, pp. 31-36.
N.N., "A promising genus for biofuel productions with Chlorella microalgae genome", Laboratoire Information Genomique et Structurale, CNRS, 2010, pp. 1-3.
Owaga et al., "Crystal analysis and high-resolution imaging of microfibrillar alphachitin from Phaeocystis", Journal of Structural Biology, vol. 171, 2010, pp. 111-116.
Retallack, "Acritarch evidence for an ediacaran adaptive radiation of fungi", Botanica Pacifica, vol. 4, 2015, pp. 19-33.
Smucker et al., "Products of photosynthesis by marine phytoplankton: chitin in TCA "protein" precipitates", Journal of Experimental Marine Biology and Ecology, vol. 104, 1986, pp. 143-152.
Solovena et al., "Marine compounds with therapeutic potential in gram-negative sepsis", Marine Drugs, vol. 11, 2013, pp. 2216-2229.
Struszczyk, "Herstellung von Chitosan und einige Anwendungen", Thesis, University of Potsdam, 2000, p. 1 and 16.
Menchicchi et al., "Structure of Chitosan Determines Its Interactions with Mucin", *Biomacromolecules*, 2014, vol. 15, pp. 3550-3558.

\* cited by examiner

CHITIN AND CHITOSAN PRODUCING METHODS

FIELD OF THE INVENTION

The invention relates to the field of polymer production, in particular to the production of chitin and chitosan from algae, particularly microalgae, belonging to the phylum Haptophyta, to the phylum Chlorophyta or to the phylum Heterokontophyta, particularly from microalgae of the genus *Isochrysis, Chlorella, Bracteacoccus, Chlorococcum, Scenedesmus, Desmodesmus, Haematococcus, Thalassiosira* or *Nannochloropsis* as well as to microalgal extracts comprising said chitin and/or chitosan and uses thereof.

BACKGROUND OF THE INVENTION

Chitin is a long-chain polymer of N-acetylglucosamine, a derivative of glucose, found in many places throughout the natural world. It is the main component of the cell walls of fungi, the exoskeletons of arthropods such as crustaceans (e.g., crabs, lobsters and shrimps) and insects, the radulae of mollusks, and the beaks and internal shells of cephalopods, including squid and octopuses. Chitin is produced naturally by the action of the enzymes chitin synthases.

Chitin has proven useful for several medical and industrial purposes. Industrial uses of chitin include food processing as edible film and as an additive to thicken and stabilize foods, as well as a fertilized to improve overall crop yields. It has been proposed as a promising substrate for engineering human tissues by use of three-dimensional bioprinting. Due to the flexibility and strength of chitin, it is also a favorable surgical thread. Additionally, chitin accelerates wound healing.

Chitosan is produced commercially by deacetylation of chitin, which is the structural element in the exoskeleton of crustaceans (such as crabs and shrimp) and cell walls of fungi. Chitosan may be produced as well naturally by enzymatic deacetilation of chitin to chitosan performed by those organisms containing chitin deacetylases enzymes (also known as chitin amidohydrolases). These chitin deacetylases recognize a sequence of four GlcNAc (N-acetylglucosamine) units in the substrate, one of which undergoes deacetylation, so the resulting chitosan has a more regular deacetylation pattern than a chitosan treated with hot NaOH. The degree of deacetylation can be determined by NMR spectroscopy, and in commercial chitosans ranges from 60% to 100%. A common method for the synthesis of chitosan is the deacetylation of chitin using sodium hydroxide in excess as a reagent and water as a solvent. This reaction pathway, when allowed to go to completion (complete deacetylation) yields up to 98% product.

Bioconversion of chitin and chitosan is performed by enzymes which are abundant in nature and include chitinases, chitosanases and chitin deacetylases (Hoell I A et al. 2010 Biotech. Gen. Eng. Rev. 27: 331-366).

Chitin can de degraded via two major pathways. When the pathway involves initial hydrolysis of the $(1 \rightarrow 4)$-$\beta$-glycosidic bond, the process is termed chitinolytic. Chitinases are found in glycoside hydrolase families 18 & 19 and hydrolyse chitin into oligosaccharides (mainly dimers) of GlcNAc. Subsequently, $\beta$-N-acetyl hexosaminidases (family 20 glycoside hydrolases; sometimes referred to as chitobiases) further degrade the oligomers, producing GlcNAc monomers. The second pathway for chitin degradation involves deacetylation of chitin to chitosan. Enzymes capable of deacetylating chitin are called chitin deacetylases, and are found in carbohydrate esterase family 4. Hydrolysis of the $(1 \rightarrow 4)$-$\beta$-glycosidic bond in chitosan is accomplished by chitosanases, which occur in families 5, 7, 8, 46, 75 and 80 of the glycoside hydrolases (Hoell I A et al. 2010 Biotech. Gen. Eng. Rev. 27: 331-366).

A number of commercial and possible biomedical uses have been associated to chitosan. By way of example, it can be used in agriculture as a seed treatment and biopesticide, helping plants to fight off fungal infections. In winemaking it can be used as a fining agent, also helping to prevent spoilage. In industry, it can be used in a self-healing polyurethane paint coating. In medicine, it may be useful in bandages to reduce bleeding and as an antibacterial agent; it can also be used to help deliver drugs through the skin, as well as in limiting fat absorption. A bandage containing chitosan (Hemcon®) has recently received FDA approval for marketing as a coagulant in bleeding wounds. Additional uses of chitosan include water processing engineering as part of the filtration process, and manufacture of large scale consumer objects.

Both chitin and chitosan show an increasing number of industrial and medical applications. Around 2000 tons of chitosan are produced every year (mainly from crab and shrimp shells). However, the current production of these polymers does not meet the growing needs by the industry. Thus, there is a need to find sources with non-seasonal production and with stable qualities and properties which the main source, marine crustacean and arthropod shells, are not able to meet. Additionally, chitosans obtained from these sources are naturally inconsistent because they suffer protein contamination, and highly variable acetylation levels and polidispersity, resulting in quite variable physicochemical characteristics.

The presence of glucosamine (GlcN) in the wall of microalgae of the class Trebouxiophyceae and others has been described extensively (Kapaun E & Reisser W 1995 Planta 197: 577-582; Burczyk J et al. 1999 Phytochemistry 51(4): 491-497; Blumreisinger M et al. 1982 Phytochemistry 22(7): 1603-1604), but the presence of chitin or chitosan structures has not been confirmed (Churchird N et al. 2001 Microbes & Environ. 16(4): 206-212, Ali M et al. 2007 Arab. J. Biotech. 10(1): 81-96, Sugimoto I et al. 2003 FEBS Letters 559(1): 51-56).

Article titled "A promising genus for biofuel production with *Chlorella* microalgae genome" by PhysOrg, Laboratoire Information Genomique et Structurale CNRS (September 2010) relates to *Chlorella* genome sequencing, suggesting the presence of putative genes for chitin/chitosan production, although production of said chitin/chitosan is not shown.

On the other hand, the presence of genome sequences putatively identified as homologues to genes responsible for chitin and chitosan synthesis and degradation is known in certain species of the genus *Chlorella* as a result of a supposed horizontal transfer from virus or bacteria. Only the activity of some of these genome sequences, putatively identified as degrading enzymes (chitinases), has been confirmed by means of heterologous recombination in bacteria (Ali et al., 2004). This demonstrates that the sequences are complete and functional in bacteria but not that they are expressed in microalgae (Blanc G et al. 2010 Plant Cell Online 22(9): 2943-2955; Churchird 2001 ad supra, Ali 2007 ad supra, Sugimoto 2003 ad supra). For example, in diatoms, the genera *Phaeodactylum* and *Chaetoceros* contain multiple chitin synthases and deacetylases, but unlike

*Thalassiosira*, they do not produce chitin or chitosan fibers (Durkin C A et al. 2009 Eukaryotic Cell 8(7): 1038-1050).

Therefore, there is a need in the art to identify natural sources of chitin and/or chitosan that satisfy the growing demand in the industry for these polymers.

SUMMARY OF THE INVENTION

The authors of the present invention have found that microalgae belonging to the phylum Haptophyta or to the phylum Chlorophyta are useful in the production of chitin and/or chitosan, and that microalgae belonging to the phylum Heterokontophyta are useful in the production of chitosan. Particularly, the authors have found that haptophytes of the genus *Isochrysis*, as well as chlorophytes of the genus *Chlorococcum, Scenedesmus, Desmodesmuss, Chlorella, Haematococcus* and *Bracteacoccus* and heterokontophytes of the genus *Nannochloropsis* produce chitin and/or chitosan in significant amounts. More in particular, they have found that that the haptophyte *Isochrysis galbana*, as well as the chlorophytes *Chlorococcum* sp., *Scenedesmus* sp., *Desmodesmus subspicatus, Chlorella vulgaris, Chlorella sorokoniana, Chlorella zofingiensis, Chlorella saccharophila, Haematococcus pluvialis* and *Bracteacoccus* sp., and the heterokontophyte *Nannochloropsis gaditana* produce chitin and/or chitosan in significant amounts. The authors of the present invention have also found that *Thalassiosira pseudonana* produces chitosan. Chitin and chitosan are detected in the microalga whole biomass and in the homogenized biomass (see Example 1). Said chitin and chitosan show polydispersity index values tipically equal to or lower than 2, corresponding to highly homogenous compositions (see Example 2).

Therefore, in an aspect the invention relates to a method for the production of chitosan that comprises:
culturing a chitosan producing algal biomass under suitable growing conditions for the production of chitosan, and
recovering an algal extract comprising said chitosan from the culture,
wherein the algal biomass comprises algae belonging to the phylum Haptophyta, to the phylum Chlorophyta, or to the phylum Heterokontophyta.

In another aspect, the invention relates to a method for the production of chitin that comprises:
culturing a chitin producing algal biomass under suitable growing conditions for the production of chitin,
disrupting the algal biomass, and
recovering an algal extract comprising said chitin from the culture,
wherein the algal biomass comprises algae belonging to the phylum Chlorophyta, and
wherein the chitin producing algal biomass is disrupted before recovering said algal extract comprising chitin.

In another aspect, the invention relates to a method for the production of a composition comprising chitin and chitosan that comprises:
culturing a chitin and chitosan producing algal biomass under suitable growing conditions for the production of chitin and chitosan,
disrupting the algal biomass, and
recovering an algal extract comprising chitin and chitosan from the culture,
wherein the algal biomass comprises algae belonging to the phylum Chlorophyta, and
wherein the chitin and chitosan producing algal biomass is disrupted before recovering said algal extract comprising chitin and chitosan.

In another aspect, the invention relates to the use of an alga for the production of chitosan wherein said alga is selected from chitosan producing algae belonging to the phylum Haptophyta, to the phylum Chlorophyta, or to the phylum Heterokontophyta.

In another aspect, the invention relates to the use of an alga for the production of chitin wherein said alga is selected from chitin producing algae belonging to the phylum Chlorophyta.

In another aspect, the invention relates to the use of an alga for the production of a composition comprising chitin and chitosan wherein said alga is selected from chitin and chitosan producing algae belonging to the phylum Chlorophyta.

In another aspect, the invention relates to the chitosan obtained by the method for the production thereof as above.

In another aspect, the invention relates to the chitin obtained by the method for the production thereof as above.

In another aspect, the invention relates to a composition comprising the chitin and chitosan obtained by the method for the production thereof as above.

In another aspect, the invention relates to an algal extract comprising chitosan, obtained by the method for the production of chitosan as above.

In another aspect, the invention relates to an algal extract comprising chitin obtained by the method for the production of chitin as above.

In another aspect, the invention relates to an algal extract comprising chitosan and chitin obtained by the method for the production of chitosan and chitin as above.

In another aspect, the invention relates to chitosan characterized by a molecular weight of 10-60 kDa, a degree of acetilation of 1-40%, a degree of polymerization of 50-500 and/or a polidispersity index of less than or equal to 2.0.

In another aspect, the invention relates to chitin characterized by a degree of polymerization of 50-500, and a polidispersity index of less than or equal to 2.0.

In another aspect, the invention relates to a composition comprising chitin and chitosan, wherein said chitosan is characterized by a molecular weight of 10-60 kDa, a degree of acetilation of 1-40%, a degree of polymerization of 50-500 and/or a polidispersity index of less than or equal to 2.0, and/wherein said chitin is characterized by a degree of polymerization of 50-500 and a polidispersity index of less than or equal to 2.0.

In another aspect, the invention relates to a food, feed, agricultural, cosmeceutical, cosmetic, nutraceutical or pharmaceutical composition comprising the products of the invention as above, or the algal extract of the invention as above, comprising between about 0.1% and about 99.998% by weight of said product, or of said algal extract.

In another aspect, the invention relates to the use of the products of the invention as above, or the algal extract of the invention as above, as an anti-acne agent, an anti-inflammatory agent, an anti-irritant agent, an anti-microbial agent, an anti-oxidant agent, an anti-tumor agent, a conditioning agent, a drug delivery agent, a fat-absorption blocking agent, a film-forming agent, a hypocholesterolemic agent, an immunostimulating agent, a lubricant agent, a wetting agent, a wound healing agent, a dermal filler agent, a material for breast implants or a plant growth promoter agent.

In another aspect, the invention relates to the product of the invention as above, or to the algal extract of the invention as above, for use in the prevention and/or treatment of cancer in a subject.

In a last aspect, the invention relates to the chitosan of the invention for use in the prevention and/or treatment of wound healing, coagulation, blood cholesterol levels, skin burns, skin damage, bone/cartilague disease, inflammation, male infertility, moist wound healing, coagulation, dental plaque, microbial infection, pain, kidney diseases, and immunomodulation.

DETAILED DESCRIPTION OF THE INVENTION

1. Definitions

Figure 1:
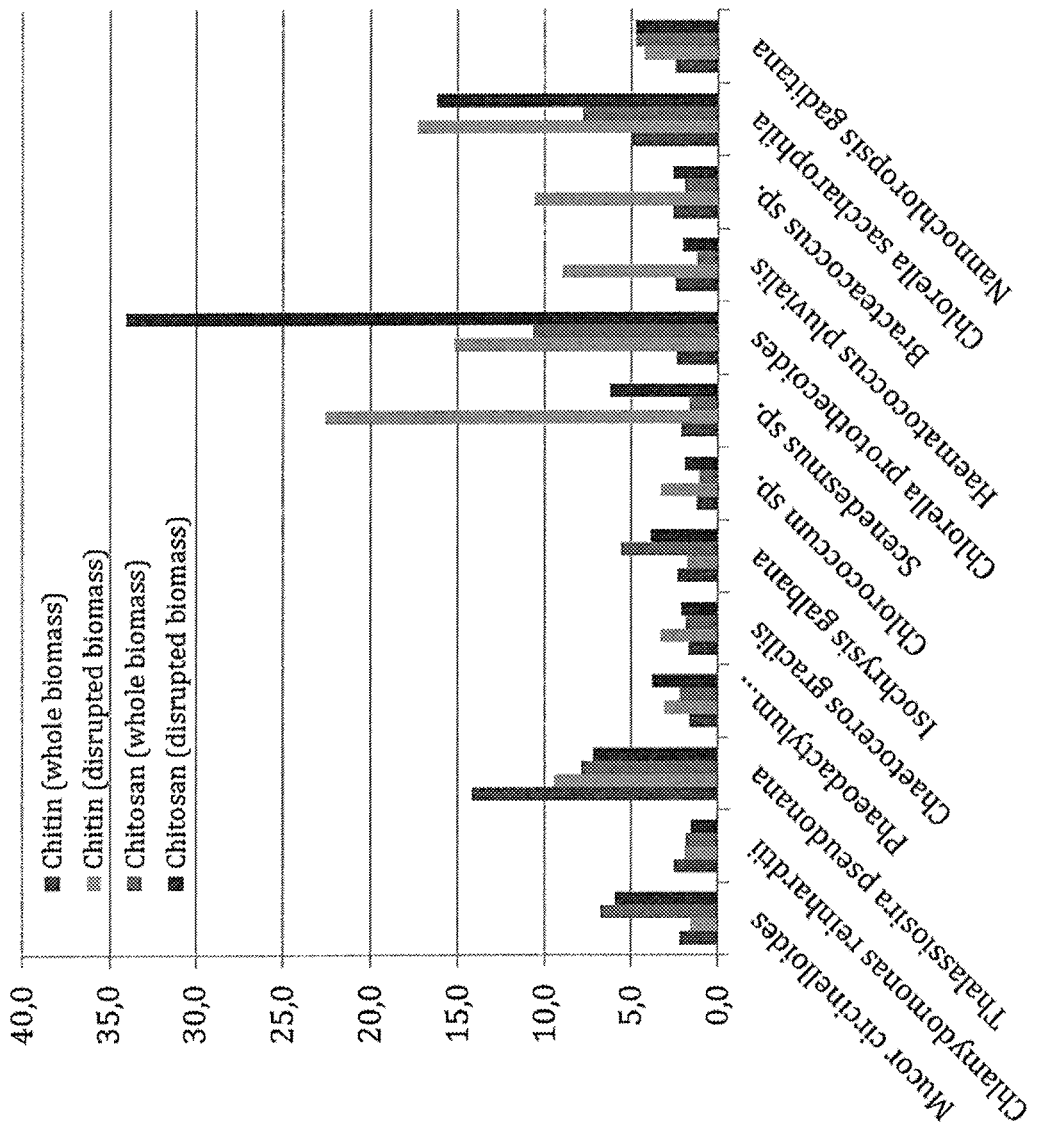
FIG. 1 shows the chitin and chitosan content in samples from a number of genera of haptophyta, chlorophyta and heterokontophyta microalgae. Normalized data (ratios) with respect to autofluorescence of each biomass are shown. Whole and homogenized microalgal biomass was analyzed.

The term "alga", as used herein, relates to a large and diverse group of simple, typically autotrophic organisms, ranging from unicellular to multicellular forms, including both macroalgae and microalgae, i.e., microscopic algae, typically found in freshwater and marine systems. In the context of the present invention, the alga is a microalga, particularly a chitin and/or chitosan producing microalga.

The term "algal extract", as used herein, relates to a product obtained from algae, more particularly obtained from microalgae, for example, by subjecting an algae culture to specific treatments. The components present in an algal extract will vary depending on the algae and the treatments applied thereon. In the context of the invention, the algal extract comprises chitin and/or chitosan.

The term "biomass", as used herein, includes biological material comprising, or deriving from, living or recently living organisms. By extension, the term includes not only the biological material or organic matter which constitutes an organism, but also the biological material or organic matter generated in a biological process, spontaneous or not spontaneous (i.e., provoked). Thus, the expression "chitin and/or chitosan producing microalgal biomass" refers to a microalga biomass comprising chitin and/or chitosan producing microalgae.

The term "chitin", as used herein, relates to a β(1-4) polymer of N-acetyl-D-glucosamine that is the major structural component of the exoskeleton of invertebrates, cuticles of insects and the cell walls of fungi. Chitin is a linear, highly crystalline homo polymer of β-1,4N-acetyl glucosamine (GlcNAc), that consists of β-1,4-linked N-acetyl glucosamine residues that are arranged in antiparallel (α), parallel (β) or mixed (γ, two parallel strands alternate with a single anti-parallel strand) strands, with the (α) configuration being the most abundant. In most organisms, chitin is cross-linked to other structural components, such as proteins and glucans. Chitin is represented by the following formula:

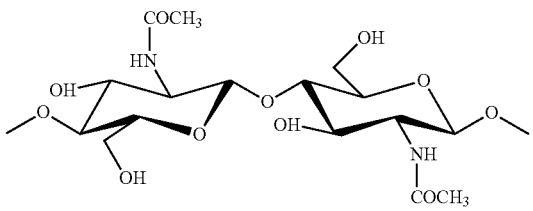

In a particular embodiment, the degree of polymerization of the chitin according to the invention ranges from 50 to 500, preferably between 100 and 250. In a particular embodiment, the chitin according to the invention shows a polydispersity index less than or equal to 2.0, preferably ranging between 1.0 and 2.0.

Chitin derivatives according to the present invention include, without limitation, chitin phosphate, chitin phosphate sulphate, chitin ethylene glycol, aminoethyl-chitin, carboxymethyl chitin, chitosan hydrogel, and hydroxyethyl chitin. Chitin derivatives can be obtained from the chitin according to the present invention by methods known by the skilled person.

The term "chitosan", as used herein, relates to a derivative of chitin obtained by deacetylation of chitin in the solid state under alkaline conditions (such as concentrated NaOH) or by enzymatic hydrolysis in the presence of a chitin deacetylase. It is a linear polysaccharide composed of randomly distributed β-(1-4)-linked D-glucosamine (deacetylated unit) and N-acetyl-D-glucosamine (acetylated unit), characterized by its average molecular weight and its degree of acetylation (proportion of acetylated glucosamine units along the polymer backbone). Chitosan is represented by the following general formula:

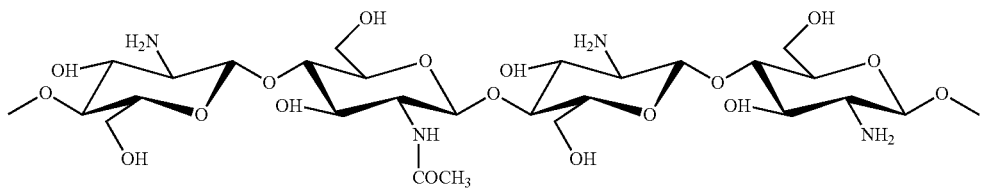

In a particular embodiment, the molecular weight of chitosan according to the invention is between 10 and 60 kDa, more preferably between 15 and 50 kDa. In a particular embodiment, the degree of acetylation ranges from 1 to 40%, preferably between 7 and 35%. In a particular embodiment, the degree of polymerization of chitosan according to the invention ranges from 50 to 500, preferably between 100 and 250. In a particular embodiment, the chitosan according to the invention shows a polydispersity index less than or equal to 2.0, preferably ranging between 1.0 and 2.0. Particularly preferred methods according to the invention for determining the degree of acetylation, the average molecular weight and polydispersity for chitosan, as well as for chitin, are shown in Example 2.

Chitosan derivatives according to the invention include, without limitation, PEG-chitosan (copolymer), chitosan azide, N-phthaloyl chitosan, chitosan-C(6)MPEG (copolymer), chitosan adipate, chitosan fumarate, chitosan lactate, chitosan acetate, chitosan hydrochloride, carboxymethylchitosan, N-sulfonato-N,O-carboxymethylchitosan, chitosan ascorbate, chitosan malate, chitosan glutamate, trimethyl chitosan (TMC), aryl chitosan, thiolated chitosan, N-succinyl-chitosan (Suc-Chi), thiosemicarbazone chitosans, N,O-carboxymethylchitosan (NOCC) and hydroxyl propylated-chitosan (HPC), N-trimethylene chloride chitosan), chitosan phthalate, and trimethyl ammonium chitosan. Chitosan derivatives can be obtained from the chitosan according to the present invention by methods known by the skilled person.

The term "class", as used herein, relates to the taxonomic rank used in the biological classification of living and fossil organisms that comes above the taxonomic rank of order and below the taxonomic rank of phylum.

The term "composition", as used herein, relates to a material composition that comprises at least two components, as well as any product resulting, directly or indirectly, from the combination of the different components in any quantity thereof. Those skilled in the art will observe that the composition may be formulated as a single formulation or may be presented as separate formulations of each of the components, which may be combined for joint use as a combined preparation. The composition may be a kit-of-parts wherein each of the components is individually formulated and packaged.

The term "degree of acetylation", as used herein, relates to presence of acetyl functional groups in a compound. Removal of said acetyl functional groups is known as deacetylation. Methods to determine the degree of acetylation/deacetylation are known by the skilled person and include, without limitation, nuclear magnetic resonance (NMR) spectroscopy.

The term "degree of polymerization", as used herein, relates to the number of monomelic units in a macromolecule or polymer. Methods to determine the degree of polymerization are known by the skilled person and are based, mainly, in number average degree of polymerization and weight average degree of polymerization. Number average degree of polymerization is found by finding the weighted mean of mole fraction; weight average degree of polymerization is found by finding the weighted mean of weight fraction.

The term "family", as used herein, relates to the taxonomic rank used in the biological classification of living and fossil organisms that comes above the taxonomic rank of genus and below the taxonomic rank of order.

The term "genus", as used herein, relates to the taxonomic rank used in the biological classification of living and fossil organisms that comes above the taxonomic rank of species and below the taxonomic rank of family.

The term "microalga", as used herein, relates to microscopic algae, typically found in freshwater and marine systems, comprising unicellular species that exist individually, in chains, or in groups. They do not have roots, stems or leaves, but most of them are capable of performing photosynthesis.

The term "molecular weight", as used herein, relates to the average molar mass of a molecule. Unlike small molecules, the molecular weight of a polymer is not one unique value. Rather, a given polymer will have a distribution of molecular weights depending for example on the way the polymer is produced. Therefore, as it is used herein, the term molecular weight for polymers refers to the distribution of molecular weight, or of the average molecular weight. Methods to determine the molecular weight are known by the skilled person and include, without limitation, 1H-NMR.

The term "order", as used herein, relates to the taxonomic rank used in the biological classification of living and fossil organisms that comes above the taxonomic rank of family and below the taxonomic rank of class.

The term "phylum", as used herein, relates to the taxonomic rank used in the biological classification of living and fossil organisms that comes above the taxonomic rank of class and below the taxonomic rank of kingdom. In relation to algae, fungi and plants, the rank phylum is also known as division.

The term "polydispersity index", also known as "dispersity", relates to a measure of the width of molecular weight distributions. This parameter measures the heterogeneity of sizes of molecules or particles in a mixture. Methods to determine dispersity are known by the skilled person and include, without limitation, size exclusion chromatography, light scattering measurement and mass spectrometry (MALDI, electrospray ionization).

2. Method for the Production of Chitosan of the Invention

The authors of the present invention have found that algae belonging to the phylum Haptophyta, Chlorophyta or Heterokontophyta are useful in the production of chitosan, and that algae belonging to the phylum Chlorophyta are useful in the production of chitin. Particularly, haptophytes of the genus *Isochrysis*, as well as chlorophytes of the genus *Chlorococcum, Scenedesmus, Desmodesmuss, Chlorella, Haematococcus* and *Bracteacoccus* and heterokontophytes of the genus *Nannochloropsis* produce chitin and/or chitosan in significant amounts. The authors have found that chitin and/or chitosan produced by these green microalgae is located within the cell wall, in contrast to other organisms wherein chitin and/or chitosan locate(s) in the exterior of the cell wall (see Example 1). Furthermore, chitin and chitosan as obtained according to the present invention show a low polydispersity index, that is to say, chitin and chitosan obtained according to the method of the invention are highly homogeneous (see Example 2), rendering these compounds suitable for therapeutic applications.

In a first aspect, the invention relates to a method for the production of chitosan (method for the production of chitosan of the invention, or first method of the invention) that comprises
  culturing a chitosan producing algal biomass under suitable growing conditions for the production of chitosan, and
  recovering an algal extract comprising said chitosan from the culture, wherein the algal biomass comprises algae belonging to the phylum Haptophyta, to the phylum Chlorophyta, or to the phylum Heterokontophyta.

Thus, in a first step of the first method of the invention, said method comprises culturing chitosan producing algal biomass under suitable growing conditions that allow the production of chitosan.

According to the invention, the chitosan producing algal biomass, particularly microalgal biomass, includes not only the biological material which constitutes the alga organism, but also the biological material or organic matter generated in a biological process, spontaneous or not, associated to said alga organism. The chitosan producing algal biomass according to the invention includes an algal biomass comprising chitosan producing algae, more particularly microalgae. Methods to determine whether an organism, particularly an alga, more particularly a microalga, is a chitosan producing microalga are known by the skilled person and include, without limitation, chitosan specific detection by chitosan-binding specific proteins, as described, in a way of a non-limiting example, by Nampally (Nampally M et al. 2012 Appl. Environ. Microbiol. 78(9): 3114-3119; see Example 1 in this application).

The chitosan producing algal biomass according to the invention includes an algal biomass comprising chitosan producing algae, in particular, an algal biomass that belongs to algae belonging to the phylum Haptophyta, to the phylum Chlorophyta, or to the phylum Heterokontophyta. In particular, the chitosan producing algal biomass, preferably chitosan producing microalgal biomass, belongs to algae belonging to the phylum Haptophyta, to the phylum Chlorophyta, or to the phylum Heterokontophyta, Phylum Haptophyta The phylum Haptophyta relates to a division of algae comprising the haptophytes. They are characterized by cells typically having two slightly unequal flagella, both of which are smooth, and a unique organelle called a haptonema, which is superficially similar to a flagellum but differs in the arrangement of microtubules and in its use. In a particular embodiment, the haptophyte of the phylum Haptophyta is a haptophyte belonging to the Prymnesiophyceae class or to the Pavlovophyceae class. In a particular embodiment, the haptophyte of the phylum Haptophyta is a microalga.

In a particular embodiment, the haptophyte belonging to the Prymnesiophyceae class is a haptophyte belonging to the Isochrysidales order, more particularly to the Isochrysidaceae family or to the Noelaerhabdaceae family.

In a particular embodiment, the haptophyte of the Isochrysidaceae family belongs to the *Isochrysis* genus or to the *Tisochrysis* genus. The *Isochrysis* genus includes, without limitation, *Isochrysis galbana, Isochrysis litoralis* and *Isochrysis maritime*. Particularly preferred haptophytes belonging to the *Isochrysis* genus include, without limitation, *Isochrysis* sp., *Isochrysis* aff. *galbana, Isochrysis galbana, Isochrysis nuda* and *Isochrysis litoralis*. More preferably, the haptophyte is *Isochrysis galbana*. Particularly preferred haptophytes belonging to the *Tisochrysis* genus include, without limitation, *Tisochrysis lutea* and *Tisochrysis* sp.

In a particular embodiment, the haptophyte of the Noelaerhabdaceae family belongs to the *Emiliania* genus. Particularly preferred haptophytes belonging to the *Emiliania* genus include, without limitation, *Emiliania huxleyi*, and *Emiliania* sp.

In a particular embodiment, the haptophyte belonging to the Pavlovophyceae class is a haptophyte belonging to the Pavlovales order, more particularly to the Pavlovaceae family. Preferably, the haptophyte of the Pavlovaceae family belongs to the *Pavlova* genus. Particularly preferred haptophytes belonging to the *Pavlova* genus include, without limitation, *Pavlova gyrans, Pavlova lutheri, Pavlova pinguis*, and *Pavlova* sp.

Phylum Chlorophyta

The phylum Chlorophyta relates to a division of green algae comprising the chlorophytes, and that includes green algae belonging to the classes Prasinophyceae, Ulvophyceae, Trebouxiophyceae, Chlorodendrophyceae and Chlorophyceae. In a particular embodiment, the chlorophyte of the phylum Chlorophyta is a chlorophyte belonging to the Trebouxiophyceae class, to the Chlorophyceae class, or to the Chlorodendrophyceae class (according to the Chlorophyta classification by Pombert; Pombert J F et al. 2005 Mol. Biol. Evol. 22(9): 1903-1918). In a particular embodiment, the chlorophyte of the phylum Chlorophyta is a microalga.

In a particular embodiment, the chlorophyte belonging to the Trebouxiophyceae class is a chlorophyte belonging to the Chlorellales order, more particularly to the Chlorellaceae family. Preferably, the chlorophyte belonging to the Chlorellaceae family belongs to the *Chlorella* genus. The *Chlorella* genus includes, without limitation, *Chlorella autotrophica, Chlorella minutissima, Chlorella pyrenoidosa, Chlorella variabilis* and *Chlorella vulgaris*. Particularly preferred chlorophytes belonging to the *Chlorella* genus include, without limitation, *Chlorella acuminata* Gerneck C, *Chlorella angustoellipsoidea* N. Hanagata & M. Chihara S, *Chlorella anitrata* var. *minor* P, *Chlorella anitrata* P, *Chlorella antarctica* (F. E. Fritsch) Wille C, *Chlorella aureoviridis* Meyer S, *Chlorella autotrophica* Shihira & R. W. Krauss S, *Chlorella botryoides* J. B. Petersen C, *Chlorella caldaria* (Tilden) M. B. Allen S, *Chlorella Candida* Shihira & R. W. Krauss S, *Chlorella capsulata* R. R. L. Guillard, H. C. Bold & F. J. MacEntee S, *Chlorella chlorelloides* (Naumann) C. Bock, L. Krienitz & T. Pröschold C, *Chlorella cladoniae* Chodat U, *Chlorella coelastroides* Chodat U, *Chlorella colonialis* C. Bock, Krienitz & Pröschold C, *Chlorella communis* Artari S, *Chlorella conductrix* (K. Brandt) Beyerinck S, *Chlorella conglomerata* (Artari) Oltmanns U, *Chlorella desiccata* P, *Chlorella ellipsoidea* var. *minor* L. Moewus C, *Chlorella ellipsoidea* Gerneck S, *Chlorella elongata* (Hindák) C. Bock, Krienitz et Pröschold, C, *Chlorella emersonii* var. *rubescens* (P. J. L. Dangeard) Fott, Lochead & Clemenqon S, *Chlorella emersonii* var. *globosa* Shihira & R. W. Krauss S, *Chlorella emersonii* Shihira & R. W. Krauss S, *Chlorella faginea* (Gerneck) Wille C, *Chlorella fusca* var. *vacuolata* I. Shihira & R. W. Krauss S, *Chlorella fusca* var. *rubescens* (P. J. L. Dangeard) Kessler, Czygan, Fott & Nováková S, *Chlorella fusca* Shihira & R. W. Krauss S, *Chlorella glucotropha* P, *Chlorella homosphaera* Skuja S, *Chlorella infusionum* Beijerinck C, *Chlorella infusionum* var. *auxenophila* Shihira & R. W. Krauss C, *Chlorella kessleri* Fott & Nováková S, *Chlorella koettlitzii* (Fritsch) Wille U, *Chlorella kolkwitzii* Naumann S, *Chlorella lacustris* Chodat U, *Chlorella lewinii* C. Bock, Krienitz & Pröschold C, *Chlorella lichina* Chodat U, *Chlorella lobophora* V. M. Andreyeva S, *Chlorella luteo-viridis* Chodat S, *Chlorella luteo-viridis* var. *lutescens* Chodat S, *Chlorella marina* Butcher C, *Chlorella miniata* (Kützing) Oltmanns C, *Chlorella minor* Naumann S, *Chlorella minutissima* Fott & Nováková C, *Chlorella mirabilis* V. M. Andreyeva C, *Chlorella mucosa* Korshikov S, *Chlorella mutabilis* Shihira & R. W. Krauss S, *Chlorella nocturna* Shihira & R. W. Krauss C, *Chlorella nordstedtii* Printz C, *Chlorella oblonga* Naumann S, *Chlorella oocystoides* Hindak C, *Chlorella ovalis* Butcher C, *Chlorella paramecii*

Loefer U, *Chlorella parasitica* (K. Brandt) Beijerinck C, *Chlorella parva* P, *Chlorella peruviana* G. Chacón Roldán C, *Chlorella photophila* Shihira & R W. Krauss C, *Chlorella pituita* C. Bock, Krienitz & Pröschold C, *Chlorella pringsheimii* Shihara & R. W>Krauss S, *Chlorella protothecoides* var. *mannophila* Shihira & R. W. Krauss U, *Chlorella protothecoides* var. *galactophila* Shihira & R. W. Krauss U, *Chlorella protothecoides* var. *acidicola* Albertano & Taddei S, *Chlorella protothecoides* Krüger S, *Chlorella protothecoides* var. *communis* Shihira & R. W. Krauss U, *Chlorella pulchelloides* C. Bock, Krienitz & Pröschold C, *Chlorella pyrenoidosa* H. Chick S, *Chlorella pyrenoidosa* var. *vacuolata* (I. Shihira & R. W. Krauss) A. E. Ergashev C, *Chlorella pyrenoidosa* var. *duplex* (Kützing) West S, *Chlorella pyrenoidosa* var. *tumidus* West C, *Chlorella regularis* var. *aprica* Shihira & R. W. Krauss C, *Chlorella regularis* var. *ubricata* Shihira & R. W. Krauss C, *Chlorella regularis* var. *minima* P, *Chlorella regularis* (Artari) Oltmanns S, *Chlorella reisiglii* S. Watanabe S, *Chlorella reniformis* S. Watanabe S, *Chlorella rotunda* C. Bock, Krienitz & Pröschold C, *Chlorella rubescens* Chodat U, *Chlorella rugosa* J. B. Petersen C, *Chlorella saccharophila* var. *ellipsoidea* (Gerneck) Fott & Nováková S, *Chlorella saccharophila* (Krüger) Migula S, *Chlorella salina* Kufferath C, *Chlorella salina* Butcher C, *Chlorella simplex* (Artari) Migula U, *Chlorella singularis* C. Bock, Krienitz & Pröschold C, *Chlorella sorokiniana* Shihira & R. W. Krauss C, *Chlorella spaerckii* Ålvik C, *Chlorella sphaerica* Tschermak-Woess C, *Chlorella stigmatophora* Butcher C, *Chlorella subsphaerica* H. Reisigl C, *Chlorella terricola* Gollerbach [Hollerbach] S, *Chlorella trebouxioides* M. Puncochárová S, *Chlorella vannielii* Shihira & R. W. Krauss C, *Chlorella variabilis* Shihira & R. W. Krauss S, *Chlorella viscosa* Chodat C, *Chlorella volutis* C. Bock, Krienitz & Pröschold C, *Chlorella vulgaris f. suboblonga* V. M. Andreeva C, *Chlorella vulgaris* var. *autotrophica* (Shihira & Krauss) Fott & Nováková C, *Chlorella vulgaris* Beyerinck [Beijerinck] C-type, *Chlorella vulgaris* var. *tertia* Fott & Novakova C, *Chlorella vulgaris f. globosa* V. M. Andreyeva C, *Chlorella vulgaris* var. *viridis* Chodat S, *Chlorella vulgaris* var. *luteo-viridis* (Chodat) Shihira & R. W. Krauss S, *Chlorella vulgaris f. minuscula* V. M. Andreyeva C, *Chlorella zofingiensis* Dönz S, and *Chlorella* sp. Preferably, the cholorophyte belonging to the *Chlorella* genus is *Chlorella saccharophila* or *Chlorella vulgaris* (CS41).

In a particular embodiment, the chlorophyte belonging to the Chlorophyceae class is a chlorophyte belonging to the Sphaeropleales order or to the Chlamydomonadales order:

In a more particular embodiment, the chlorophyte belonging to the Sphaeropleales order is a chlorophyte belonging to Scenedesmaceae family, to the Neochloridaceae family, to the Bracteacoccaceae family, or to the Selenastraceae family.

More particularly, the cholorophyte belonging to the Scenedesmaceae family are selected from microalgae belonging to the *Scenedesmus* genus, to the *Desmodesmus* genus, or to the *Coelastrella* genus.

The *Scenedesmus* genus includes, without limitation, *Scenedesmus dimorphus, Scenedesmus acuminatus, Scenedesmus subspicatus* and *Scenedesmus* sp. Particularly preferred chlorophytes belonging to the *Scenedesmus* genus include, without limitation, the following:

*Scenedesmus abundans* var. *asymmetrica* (Schroeder) G. M. Smith S
*Scenedesmus abundans* var. *peruvianus* (E. Hegewald) E. Hegewald S
*Scenedesmus abundans* (O. Kirchner) Chodat S
*Scenedesmus abundans* var. *longicauda* G. M. Smith C
*Scenedesmus abundans* var. *bicaudatus* Proshkina-Lavrenko S
*Scenedesmus abundans* var. *skujae* Compère C
*Scenedesmus abundans* var. *brevicauda* G. M. Smith C
*Scenedesmus aciculatus* P. González C
*Scenedesmus aculeolatus* Reinsch S
*Scenedesmus aculeotatus* Reinsch C
*Scenedesmus acuminatus* var. *minor* G. M. Smith S
*Scenedesmus acuminatus f. contortus* L. Krienitz P
*Scenedesmus acaminatus* var. *briseriatus* Reinhard S
*Scenedesmus acuminatus f. globosus* T. Hortobágyi P
*Scenedesmus acuminatus* var. *[javanensis] f. globosus* Uherkovich S
*Scenedesmus acuminatus f. procerus* T. Hortobágyi P
*Scenedesmus acuminatus f. maximus* Uherkovich P
*Scenedesmus acuminatus* var. *tetradesmoides* G. M. Smith S
*Scenedesmus acuminatus* var. *biseriatus* Reinhard C
*Scenedesmus acuminatus f. tortuosus* (Skuja) Korshikov S
*Scenedesmus acuminatus f. tetradesmoides* (G. M. Smith) Korshikov U
*Scenedesmus acuminatus* var. *bernardii* (G. M. Smith) Dedusenko S
*Scenedesmus acuminatus* (Lagerheim) Chodat S
*Scenedesmus acuminatus* var. *inermius* (Playfair) Playfair C
*Scenedesmus acuminatus* var. *tortuosus* (Skuja) Ooshima S
*Scenedesmus acuminatus* var. *elongatus* G. M. Smith S
*Scenedesmus acutiformis* var. *bicaudatus* Guglielmetti S
*Scenedesmus acutiformis* Schröder S
*Scenedesmus acutiformis* var. *tricostatus* Schröder S
*Scenedesmus acutiformis* var. *costatus* (Huber-Pestolozzi) Pankow C
*Scenedesmus acutiformis* var. *brasiliensis* (Bohlin) West & G. S. West P
*Scenedesmus acutus* var. *obliquus* Rabenhorst S
*Scenedesmus acutus* Meyen S
*Scenedesmus acutus* var. *dimorphus* (Turpin) Rabenhorst S
*Scenedesmus acutus f. tetradesmiformis* (Wolosz.) Uherkovich P
*Scenedesmus acutus f. alternans* Hortobagyi S
*Scenedesmus acutus f. alterans* Hortobagyi C
*Scenedesmus acutus* var. *globosus* Hortobágyi C
*Scenedesmus acutus* var. *globosus* Hortobágyi C
*Scenedesmus acutus* var. *globosus* Hortobágyi C -continued

*Scenedesmus acutus* f. *costulatus* (Chodat) Uherkovich P
*Scenedesmus aldavei* Hegewald C
*Scenedesmus alternans* var. *prescottii* B. Fott & J. Komárek P
*Scenedesmus alternans* var. *apiculatus* West & G. S. West S
*Scenedesmus alternans* Reinsch S
*Scenedesmus ambuehlii* F. Hindák C
*Scenedesmus anhuiensis* S. S. Wang C
*Scenedesmus anomalus* (G. M. Smith) Ahlstrom & Tiffany S
*Scenedesmus antennatus* Brébisson S
*Scenedesmus antillarum* Comas González S
*Scenedesmus apicaudatus* (W. & G. S. West) Chodat P
*Scenedesmus apiculatus* var. *irregularis* Dedusenko-Shchegoleva C
*Scenedesmus apiculatus* Corda U
*Scenedesmus apiculatus* (West & G. S. West) Chodat U
*Scenedesmus apiculatus* f. *skujae* Chodat C
*Scenedesmus arcuatus* f. *prescottii* (B. Fott & J. Komárek) H. Kuosa P
*Scenedesmus arcuatus* var. *capitatus* G. M. Smith S
*Scenedesmus arcuatus* var. *irregularis* E. A. Flint S
*Scenedesmus arcuatus* (Lemmermann) Lemmermann C
*Scenedesmus arcuatus* var. *platydiscus* G. M. Smith S
*Scenedesmus arcuatus* var. *gracilis* (T. Hortobágyi) F. Hindák P
*Scenedesmus arcuatus* f. *gracilis* T. Hortobágyi C
*Scenedesmus aristatus* var. *major* Pèterfi P
*Scenedesmus aristatus* Chodat S
*Scenedesmus armatus* var. *ecornis* Chodat C
*Scenedesmus armatus* var. *exaculeatus* Chodat C
*Scenedesmus armatus* var. *subalternans* G. M. Smith S
*Scenedesmus armatus* var. *spinosus* F. E. Fritsch & Rich S
*Scenedesmus armatus* var. *bicaudatus* (Guglielmetti) Chodat S
*Scenedesmus armatus* var. *smithii* Chodat P
*Scenedesmus armatus* var. *microspinosus* (T. Hortobágyi) E. Hegewald & F. Hindák P
*Scenedesmus armatus* var. *longispina* (R. Chodat) E. Hegewald & F. Hindák P
*Scenedesmus armatus* var. *boglariensis* f. *simplex* Péterfi P
*Scenedesmus armatus* var. *dispar* Philipose S
*Scenedesmus armatus* var. *pluricostatus* P. Bourrelly C
*Scenedesmus armatus* var. *boglariensis* f. *semicostatus* Péterfi P
*Scenedesmus armatus* var. *boglariensis* f. *deflexus* Péterfi P
*Scenedesmus armatus* var. *boglariensis* f. *brevicaudatus* Pèterfi P
*Scenedesmus armatus* var. *bolgariensis* f. *bicaudus* C
*Scenedesmus armatus* (R. Chodat) R. Chodat S
*Scenedesmus armatus* var. *bolgariensis* Hortobágyi C
*Scenedesmus armatus* var. *bajaensis* Uherkovich P
*Scenedesmus armatus* var. *boglariensis* Hortobagyi P
*Scenedesmus armatus* var. *platydiscus* (G. M. Smith) Fott & Komarek P
*Scenedesmus armatus* var. *boglariensis* f. *bicaudatus* Hortobagyi P
*Scenedesmus arthrodesmiformis* Schröder S
*Scenedesmus arvernensis* R. &F. Chodat C
*Scenedesmus asymmetricus* (Schröder) Chodat S
*Scenedesmus asymmetricus* var. *multispinosus* Hortobágyi C
*Scenedesmus bacillaris* Gutwinski C
*Scenedesmus baculiformis* Chodat C
*Scenedesmus bajacalifornicus* L. A. Lewis & Flechtner ex E. Hegewald, C. Bock & Krienitz C
*Scenedesmus balatonicus* Hortobagyi P
*Scenedesmus basiliensis* Chodat C
*Scenedesmus bernardii* G. M. Smith S
*Scenedesmus bicaudatus* var. *brevicaudatus* Hortobágyi C
*Scenedesmus bicaudatus* Dedusenko S
*Scenedesmus bicaudatus* (Hansgirg) Chodat S
*Scenedesmus bicellularis* R. Chodat S
*Scenedesmus bidentatus* Hansgirg C
*Scenedesmus bijuga* (Turpin) Lagerheim C
*Scenedesmus bijuga* var. [*alternans*] f. *parvus* G. M. Smith S
*Scenedesmus bijuga* var. *disciformis* (Chodat) C. R. Leite P
*Scenedesmus bijuga* var. *alternans* (Reinsch) Hansgirg C
*Scenedesmus bijugatus* var. *granulatus* Schmidle S
*Scenedesmus bijugatus* var. *radiatus* (Reinsch) Hansgirg P
*Scenedesmus bijugatus* var. *seriatus* Chodat C
*Scenedesmus bijugatus* Kützing S
*Scenedesmus bijugatus* var. *costatus* Huber-Pestalozzi S
*Scenedesmus bijugatus* f. *arcuatus* Lemmermann S
*Scenedesmus bijugatus* f. *major* Isabella & R. J. Patel P
*Scenedesmus bijugatus* var. *arcuatus* Lemmermann S
*Scenedesmus bijugatus* var. *bicellularis* (Chodat) Philipose S
*Scenedesmus bijugatus* var. *disciformis* Chodat S
*Scenedesmus bijugatus* f. *disciformis* (Chodat) Volk P
*Scenedesmus bijugus* var. *alternans* (Reinsch) Hansgirg S
*Scenedesmus bijugus* var. *duplex* Playfair C
*Scenedesmus bijugus* var. *inermis* (Playfair) V. May P
*Scenedesmus bijugus* var. *obtusiusculus* (Chodat) G. M. Smith C -continued

*Scenedesmus bijugus* var. *ralfsii* (Playfair) V. May P
*Scenedesmus bijugus* (Turpin) Lagerheim C
*Scenedesmus bijugus* var. *arcuatus* Lemmermann S
*Scenedesmus brasiliensis* var. *norvegicus* Printz C
*Scenedesmus brasiliensis* var. *cinnamomeus* Y. V. Roll S
*Scenedesmus brasiliensis* var. *quadrangularis* (Corda) Borge P
*Scenedesmus brasiliensis* var. *serrato - perforatus* (R. J. Patel & P. K. Isabella George) E. Hegewald & F. Hindák P
*Scenedesmus brasiliensis* f. *granulatus* Isabella & R. J. Patel P
*Scenedesmus brasiliensis* Bohlin S
*Scenedesmus breviaculeatus* Chodat, R. C
*Scenedesmus brevispina* (G. M. Smith) R. Chodat C
*Scenedesmus brevispina* f. *granulatus* Hortobágyi S
*Scenedesmus caribeanus* Kom. P
*Scenedesmus carinatus* (Lemmermann) Chodat S
*Scenedesmus carinatus* f. *brevicaudatus* Uherkovich S
*Scenedesmus carinatus* var. *bicaudatus* Uherkovich C
*Scenedesmus carinatus* var. *diagonalis* Shen U
*Scenedesmus caudata* Corda S
*Scenedesmus caudato-aculeolatus* Chodat C
*Scenedesmus caudatus* f. *abundans* Kirchner S
*Scenedesmus caudatus* f. *setosus* Kirchner S
*Scenedesmus caudatus* Corda P
*Scenedesmus chlorelloides* Chodat C
*Scenedesmus circumfusus* var. *bicaudatus* f. *granulatus* Hortobagyi P
*Scenedesmus circumfusus* Hortobágyi C
*Scenedesmus circumfusus* var. *bicaudatus* Hortobágyi C
*Scenedesmus circumfusus* var. *semiquadrispinosus* Hortobagyi C
*Scenedesmus coalitus* Hortobagyi P
*Scenedesmus coelastroides* (Bohlin) Schmidle S
*Scenedesmus columnatus* var. *bicaudatus* Hortobágyi S
*Scenedesmus columnatus* Hortobágyi S
*Scenedesmus communis* E. Hegewald S
*Scenedesmus corallinus* Chodat S
*Scenedesmus costato-granulatus* var. *elegans* (T. Hortobágyi) E. Hegewald & L. Krienitz S
*Scenedesmus costatogranulatus* Skuja S
*Scenedesmus costatus* Schmidle S
*Scenedesmus costatus* var. *coelastroides* Bohlin S
*Scenedesmus costulatus* Chodat S
*Scenedesmus crassidentatus* Péterfi P
*Scenedesmus crassus* Chodat S
*Scenedesmus cumbricus* (G. S. West) Chodat S
*Scenedesmus cuneatus* A. P. Skabichevskij S
*Scenedesmus curvatocornis* Proshkina-Lavrenko S
*Scenedesmus curvatus* Bohlin C
*Scenedesmus dactylococcoides* Chodat S
*Scenedesmus denticulatus* f. *granulatus* Hortobagyi C
*Scenedesmus denticulatus* f. *carinatus* P. Mosto P
*Scenedesmus denticulatus* var. *australis* Playfair C
*Scenedesmus denticulatus* Lagerheim S
*Scenedesmus denticulatus* var. *linearis* Hansgirg S
*Scenedesmus denticulatus* var. *fenestratus* (Teiling) Uherk. P
*Scenedesmus denticulatus* var. *minor* Shen C
*Scenedesmus denticulatus* var. *gracilis* Playfair C
*Scenedesmus denticulatus* var. [*linearis*] f. *granulatus* Hortobágyi S
*Scenedesmus denticulatus* var. *disciformis* Hortobágyi C
*Scenedesmus denticulatus* var. *brevispinus* (Smith) May C
*Scenedesmus denticulatus* var. *lunatus* West & G. S. West S
*Scenedesmus denticulatus* var. *pseudogranulatus* L. Péterfi P
*Scenedesmus deserticola* L. A. Lewis & V. R. Flechtner ex E. Hegewald, C. Bock & Krienitz C
*Scenedesmus diagonalis* Fang C
*Scenedesmus dimorphus* (Turpin) Kützing S
*Scenedesmus dimorphus* f. *granulatus* Isabella & R. J. Patel S
*Scenedesmus dirmorphus* var. *longispina* Compère C
*Scenedesmus disciformis* (Chodat) Fott & Komárek S
*Scenedesmus dispar* Brébisson S
*Scenedesmus dispar* f. *denticulatus* Uherkovich C
*Scenedesmus dispar* f. *elegans* Uherkovich C
*Scenedesmus dispar* f. *semidenticulatus* Uherkovich C
*Scenedesmus dispar* var. *robustus* Uherkovich C
*Scenedesmus dispar* var. *costatogranulatus* Hortobagyi C
*Scenedesmus dispar* var. *rabae* Uherkovich C
*Scenedesmus dispar* var. *samoensis* Wille P
*Scenedesmus dissociatus* (P. A. Verses & F. R. Trainor) E. Hegewald & N. Hanagata S
*Scenedesmus distentus* (T. Holtmann) E. Hegewald & N. Hanagata S
*Scenedesmus echinulatus* Dedusenko S
*Scenedesmus ecornis* var. *mucronulatus* Chodat S
*Scenedesmus ecornis* var. *polymorphus* Chodat P
*Scenedesmus ecornis* (Ehrenberg) Chodat C -continued

*Scenedesmus ecornis* var. *flexuosus* Lemmermann S
*Scenedesmus ecornis* var. *disciformis* (Chodat) Chodat S
*Scenedesmus elegans* L. S. Péterfi S
*Scenedesmus elegans* f. *regularis* L. S. Péterfi S
*Scenedesmus ellipsoideus* Chodat P
*Scenedesmus ellipticus* Corda C
*Scenedesmus eupectinatus* Dedusenko S
*Scenedesmus falcatus* f. *tortuosa* Skuja S
*Scenedesmus falcatus* Chodat S
*Scenedesmus fenestratus* Teiling C
*Scenedesmus flavescens* Chodat S
*Scenedesmus flavescens* var. *breviaculeatus* (P. Bourrelly) E. Hegewald P
*Scenedesmus flavescens* var. *longicaudatus* E. Hegewald P
*Scenedesmus flexuosus* (Lemmermann) Ahlstrom S
*Scenedesmus furcosus* Hortobágyi S
*Scenedesmus fuscus* (Shihira & R. W. Krauss) Hegewald C
*Scenedesrmus fuscus* var. *peruvianus* E. Hegewald C
*Scenedesmus fusiformis* Meneghini C
*Scenedesmus gracilis* Matvienko C
*Scenedesmus gracils* Matvienko S
*Scenedesmus graevenitzii* Bernard S
*Scenedesmus grahneisii* (Heynig) Fott C
*Scenedesmus granulatus* var. *verrucosus* Dedusenko S
*Scenedesmus granulatus* f. *spinosus* Hortobagyi C
*Scenedesmus granulatus* West & G. S. West S
*Scenedesmus granulatus* f. *elegans* T. Hortobágyi S
*Scenedesmus granulatus* f. *salina* P
*Scenedesmus granulatus* f. *disciformis* Hortobagyi C
*Scenedesmus granulatus* var. *verrucocostatus* Hortobagyi C
*Scenedesmus gujaratensis* Isabella & R. J. Patel C
*Scenedesmus gutwinskii* Chodat S
*Scenedesmus gutwinskii* var. *heterospina* Bodrogközy S
*Scenedesmus gutwinskii* var. *bacsensis* Uherkovich P
*Scenedesmus hanleyi* R. F. Fleming C
*Scenedesmus heimii* var. *longispina* P. Mosto C
*Scenedesmus helveticus* Chodat S
*Scenedesmus heteracanthus* P. González C
*Scenedesmus hindakii* E. Hegewald & N. Hanagata C
*Scenedesmus hirsutus* F. Hindák C
*Scenedesmus hortobagyi* Philipose C
*Scenedesmus houlensis* Rayss S
*Scenedesmus huangshanensis* S. S. Wang C
*Scenedesmus hystrix* var. *regularis* H. Alten S
*Scenedesmus hystrix* var. [*armatus*] f. *depauperata* Wille U
*Scenedesmus hystrix* Lagerheim S
*Scenedesmus hystrix* var. *armatus* R. Chodat S
*Scenedesmus incrassatulus* var. *alternans* (Bohlin) Dedusenko S
*Scenedesmus incrassatulus* var. *mononae* G. M. Smith S
*Scenedesmus incrassatulus* Bohlin S
*Scenedesmus indicus* Philipose C
*Scenedesmus inermis* (Fott) Hegewald S
*Scenedesmus insignis* (W. & G. S. West) Chodat S
*Scenedesmus intermaedius* f. *granulatus* Hortobgyi S
*Scenedesmus intermedius* var. *acutispinus* (Y. V. Roll) E. Hegwald & An S
*Scenedesmus intermedius* var. *inflatus* (Svirenko) E. Hegewald & S. S. An P
*Scenedesmus intermedius* Chodat S
*Scenedesmus intermedius* var. *acaudatus* Hortobagyi P
*Scenedesmus intermedius* var. *bicaudatus* Hortobágyi S
*Scenedesmus intermedius* var. *balatonicus* Hortobágyi S
*Scenedesmus javanensis* f. *schroeteri* (Huber-Pestalozzi) Comas & Komárek S
*Scenedesmus javanensis* Chodat S
*Scenedesmus jovais* P
*Scenedesmus kerguelensis* Wille C
*Scenedesmus kissii* Hortobágyi C
*Scenedesmus komarekii* E. H. Hegewald S
*Scenedesmus komarekii* var. *hirsutus* (F. Hindák) E. Hegewald & F. Hindák P
*Scenedesmus lefevrei* Deflandre S
*Scenedesmus lefevrei* var. *manguinii* Lefèvre & Bourrelly C
*Scenedesmus lefevrei* var. *muzzanensis* Huber-Pestalozzi S
*Scenedesmus linearis* Komárek S
*Scenedesmus littoralis* Hanagata C
*Scenedesmus longispina* R. Chodat C
*Scenedesmus longus* var. *brevispina* G. M. Smith S
*Scenedesmus longus* var. *naegelii* Brébisson S
*Scenedesmus longus* var. *minutus* G. M. Smith S
*Scenedesmus longus* var. *carpetana* P. González C
*Scenedesmus longus* Meyen S
*Scenedesmus longus* f. *bidigitatus* Isabella & R. J. Patel C
*Scenedesmus luna* Corda S

*Scenedesmus lunatus* (W. & G. S. West) Chodat S
*Scenedesmus magnus* Meyen S
*Scenedesmus magnus* var. *naegelii* (Brébisson) Tsarenko S
*Scenedesmus maximus* var. *peruviensis* E. Hegewald C
*Scenedesmus maximus* (West & G. S. West) Chodat S
*Scenedesmus maximus* var. *arcuatus* S
*Scenedesmus microspina* Chodat S
*Scenedesmus minutus* (G. M. Smith) Chodat S
*Scenedesmus mirus* Hortobagyi C
*Scenedesmus morzinensis* Deflandre C
*Scenedesmus multicauda* Massjuk S
*Scenedesmus multiformis* Hegewald & Hindák S
*Scenedesmus multispina* Svirenko C
*Scenedesmus multistriatus* (Trenkwalder) N. Hanagata C
*Scenedesmus naegelii* Brébisson C
*Scenedesmus nanus* Chodat P
*Scenedesmus notatus* Corda S
*Scenedesmus nygaardii* Huber S
*Scenedesmus oahuensis* var. *clathratus* S
*Scenedesmus oahuensis* var. *clathratus* f. *longiclathratus* G. Tell S
*Scenedesmus oahuensis* (Lemmermann) G. M. Smith S
*Scenedesmus obliquus* var. *dimorphus* (Turpin) Hansgirg S
*Scenedesmus obliquus* (Turpin) Kützing S
*Scenedesmus obliquus* var. *inermius* Playfair S
*Scenedesmus obliquus* f. *tetradesmoides* Dedusenko-Shchegoleva C
*Scenedesmus obliquus* var. *alternans* Khristyuk U
*Scenedesmus obliquus* f. *alternans* (Reinsch) Compère U
*Scenedesmus obliquus* f. *magnus* Bernard S
*Scenedesmus obliquus* var. *acuminatus* (Lagerheim) Chodat S
*Scenedesmus obliquus* var. *antennatus* (Brébisson) Playfair P
*Scenedesmus obtusiusculus* Chodat S
*Scenedesmus obtusus* var. *ecornis* Franzé U
*Scenedesmus obtusus* var. *apiculatus* (West & G. S. West) P. Tsarenko C
*Scenedesmus obtusus* var. *graevenitzii* (Bernard) H. Kuosa P
*Scenedesmus obtusus* var. *alternans* (Reinsch) Compère S
*Scenedesmus obtusus* f. *disciformis* (Chodat) Compère C
*Scenedesmus obtusus* var. *cornutus* Franzé P
*Scenedesmus obtusus* Meyen C - type
*Scenedesmus oocystiformis* (J. W. G. Lund) N. Hanagata S
*Scenedesmus opoliensis* var. *diagonalis* Shen C
*Scenedesmus opoliensis* var. *dispar* Shen C
*Scenedesmus opoliensis* var. *aculeatus* Hortobagyi P
*Scenedesmus opoliensis* f. *granulatus* Hortobagyi P
*Scenedesmus opoliensis* var. *extensus* Hortobagyi C
*Scenedesmus opoliensis* var. *polycostatus* Hortobagyi & Nemeth C
*Scenedesmus opoliensis* P. G. Richter S
*Scenedesmus opoliensis* var. *mononensis* Chodat S
*Scenedesmus opoliensis* var. *setosus* Dedusenko S
*Scenedesmus opoliensis* var. *asymmetricus* Printz C
*Scenedesmus opoliensis* var. *carinatus* Lemmermann S
*Scenedesmus opoliensis* var. *alatus* N. Dedusenko-Shchegoleva S
*Scenedesmus opoliensis* var. *contacta* Prescott S
*Scenedesmus opoliensis* var. *aculeolatus* Printz C
*Scenedesmus opoliensis* var. *hyperabundans* C
*Scenedesmus opoliensis* var. *abundans* C
*Scenedesmus opoliensis* var. *bicaudatus* Hortobagyi P
*Scenedesmus ornatus* (Lemmerm.) G. M. Smith S
*Scenedesmus ovalternus* Chodat S
*Scenedesmus ovalternus* var. *graevenitzii* (Bernard) Chodat S
*Scenedesmus ovalternus* Brébisson S
*Scenedesmus pannonicus* Hortobágyi S
*Scenedesmus papillatus* C.-C. Jao S
*Scenedesmus papillosum* Pankow C
*Scenedesmus parisiensis* Chodat C
*Scenedesmus parvus* (G. M. Smith) Bourrelly S
*Scenedesmus pecsensis* Uherkovich C
*Scenedesmus pecsensis* f. *denticulatus* Uherkovich P
*Scenedesrmus pecsensis* var. *setosus* Uherkovich P
*Scenedesmus pectinatus* Meyen S
*Scenedesmus pectinatus* var. *distentus* T. Holtmann C
*Scenedesmus perforatus* var. *circumcinctus* S
*Scenedesmus perforatus* f. *denticulatus* C
*Scenedesmus perforatus* Lemmermann S
*Scenedesmus perforatus* f. *bicaudatus* Compère S
*Scenedesmus perforatus* var. *spinosus* G. Tell S
*Scenedesmus perforatus* var. *argentinensis* S
*Scenedesmus perforatus* var. *clathlatus* f. *longiclathratus* S
*Scenedesmus perforatus* var. *ornatus* S
*Scenedesmus perforatus* var. *oahuensioides* S

*Scenedesmus perforatus* var. *major* S
*Scenedesmus perforatus* var. *pologranulatus* S
*Scenedesmus perforatus* var. *iberaënsis* S
*Scenedesmus perforatus* var. *perornatus* S
*Scenedesmus perforatus* var. *papillatus* S
*Scenedesmus perforatus* var. *clathlatus* S
*Scenedesmus perforatus* var. *spinosus* S
*Scenedesmus perforatus* var. *ornatus* f. *mirabilis* S
*Scenedesmus perforatus* var. [*ornatus*] f. *mirabilis* S
*Scenedesmus perforatus* var. *ornatus* f. *cornutus* S
*Scenedesmus planctonicus* (Korshikov) Fott P
*Scenedesmus planctonicus* (Korshikov) Fott S
*Scenedesmus platydiscus* (G. M. Smith) Chodat C
*Scenedesmus pleiomriphus* F. Hindák C
*Scenedesmus polessicus* P. Tsarenko C
*Scenedesmus polydenticulatus* Hortobagyi C
*Scenedesmus polyglobulus* Hortobágyi C
*Scenedesmus polyspinosus* Hortobágyi C
*Scenedesmus praetervisus* Chodat P
*Scenedesmus prismaticus* Bruhl & Biswas C
*Scenedesmus prismaticus* var. *spinosus* S. S. Wang C
*Scenedesmus producto-capitatus* var. *planus* Roll C
*Scenedesmus producto-capitatus* var. *alternans* Swirenko C
*Scenedesmus producto-capitatus* Schmula C
*Scenedesmus productocapitatus* var. *indicus* Hegewald C
*Scenedesmus protuberans* f. *minor* S. H. Li S
*Scenedesmus protuberans* var. *aristatus* (Chodat) Dedusenko C
*Scenedesmus protuberans* var. *cornutogranulatus* Hortobagyi C
*Scenedesmus protuberans* var. *minor* Ley P
*Scenedesmus protuberans* F. E. Fritsch & M. F. Rich S
*Scenedesmus pseudoarmatus* T. Hortobágyi C
*Scenedesmus pseudobernardii* f. *globosus* L. Krienitz C
*Scenedesmus pseudobernardii* f. *procerus* (T. Hortobágyi) L. Krienitz P
*Scenedesmus pseudobernardii* Comas & Komárek S
*Scenedesmus pseudodenticulatus* E. Hegewald S
*Scenedesmus pseudogranulatus* Massjuk C
*Scenedesmus pseudogranulatus* var. *hystricoides* Massjuk S
*Scenedesmus pseudohystrix* Massjuk S
*Scenedesmus pyrus* Corda S
*Scenedesmus quadrialatus* S. S. Wang C
*Scenedesmus quadricauda* var. *eualternans* Proshkina-Lavrenko C
*Scenedesmus quadricauda* f. *bicaudatus* Isabella & R. J. Patel P
*Scenedesmus quadricauda* var. *westii* G. M. Smith S
*Scenedesmus quadricauda* var. *longispina* (Chodat) G. M. Smith S
*Scenedesmus quadricauda* var. *lefevrii* (Delandre) Dedusenko C
*Scenedesmus quadricauda* var. *parvus* G. M. Smith S
*Scenedesmus quadricauda* var. *vesiculosus* Proshkina-Lavrenko S
*Scenedesmus quadricauda* var. *coutei* S
*Scenedesmus quadricauda* var. *setosus* (Kirchner) Hansgirg S
*Scenedesmus quadricauda* f. *major* Isabella & R. J. Patel P
*Scenedesmus quadricauda* f. *major* S
*Scenedesmus quadricauda* var. *helvieticus* (Chodat) Dedusenko S
*Scenedesmus quadricauda* var. *striatus* Dedusenko C
*Scenedesmus quadricauda* var. *inflatus* Svirenko S
*Scenedesmus quadricauda* var. *asymemetricus* Schröder C
*Scenedesmus quadricauda* var. *papillatus* Svirenko S
*Scenedesmus quadricauda* var. *ellipticus* West & G. S. West P
*Scenedesmus quadricauda* var. *rectangularis* G. S. West P
*Scenedesmus quadricauda* f. *vidyanagarensis* Isabella & R. J. Patel P
*Scenedesmus quadricauda* var. *microspina* (Chodat) Philipose S
*Scenedesmus quadricauda* var. *insignis* West & G. S. West S
*Scenedesmus quadricauda* Chodat S
*Scenedesmus quadricauda* var. *oahuensis* Lemmermann S
*Scenedesmus quadricauda* var. *armatus* (Chodat) Dedusenko S
*Scenedesmus quadricauda* var. *dispar* Brébisson P
*Scenedesmus quadricauda* var. *quadrispina* (Chodat) G. M. Smith S
*Scenedesmus quadricauda* var. *longispinus* G. M. Smith C
*Scenedesmus quadricauda* var. *incurvus* Playfair C
*Scenedesmus quadricauda* var. *horridus* Kirchner C
*Scenedesmus quadricauda* f. *minus* Ralfs C
*Scenedesmus quadricauda* f. *crassiaculeatus* Uherkovich C
*Scenedesmus quadricauda* f. *granulatus* Hortobagyi P
*Scenedesmus quadricauda* var. *ecornis* Francé P
*Scenedesmus quadricauda* var. *maximus* (West & G. S. West) Chodat S
*Scenedesmus quadricauda* var. *acutispinus* Roll S
*Scenedesmus quadricauda* (Turpin) Brébisson C
*Scenedesmus quadricauda* var. *asymmetricus* Schröder S
*Scenedesmus quadricauda* var. *bicaudata* Hansgirg S
*Scenedesmus quadricauda* var. *abundans* (Kirchner) Hansgirg S

*Scenedesmus quadricauda* var. *dentatus* Dedusenko S
*Scenedesmus quadricauda* var. *opoliensis* (P. G. Richter) West & G. S. West P
*Scenedesmus quadricauda* var. *maximus* West & G. S. West S
*Scenedesmus quadricauda* var. *inermius* Playfair C
*Scenedesmus quadricauda* var. *africanus* Fritsch C
*Scenedesmus quadricaudata* var. *biornata* Kiss S
*Scenedesmus quadricaudus* var. *aculeolatus* Printz C
*Scenedesmus quadricaudus* var. *spinosus* Dedusenko S
*Scenedesmus quadrispina* var. *longispinus* Chuang C
*Scenedesmus quadrispina* Chodat C
*Scenedesmus quadrispina* f. *crassispinosus* Péterfi P
*Scenedesmus raciborskii* Woloszynska C
*Scenedesmus ralfsii* Playfair S
*Scenedesmus reginae* (T. Holtmann) E. Hegewald & N. Hanagata P
*Scenedesmus regularis* Svirenko S
*Scenedesmus reniformis* Playfair C
*Scenedesmus rostrato-spinosus* R. Chodat C
*Scenedesmus rostrato-spinosus* var. *serrato-pectinatus* Chodat S
*Scenedesmus rotundus* H. C. Wood P
*Scenedesmus rotundus* L. A. Lewis & Flechtner C
*Scenedesmus rubescens* (P. J. L. Dangeard) E. Kessler, M. Schafer, C. Hummer, A. Kloboucek & V. A. R. Huss S
*Scenedesmus scenedesmoides* Chodat S
*Scenedesmus schnepfii* E. Hegewald & S. S. An C
*Scenedesmus schroeteri* Huber-Pestalozzi S
*Scenedesmus securiformis* Playfair C
*Scenedesmus semicristatus* Uherkovich S
*Scenedesmus semipulcher* Hortobágyi C
*Scenedesmus sempervirens* Chodat S
*Scenedesmus senilis* Corda P
*Scenedesmus serrato-perforatus* R. J. Patel & P. K. Isabella George C
*Scenedesmus serratus* (Corda) Bohlin S
*Scenedesmus serratus* f. *interruptus* Philipose C
*Scenedesmus serratus* f. *minor* Chodat S
*Scenedesmus setiferus* Chodat P
*Scenedesmus sihensis* Negoro S
*Scenedesmus smithii* Teiling U
*Scenedesmus smithii* Chodat C
*Scenedesmus smithii* var. *spinulosus* S. S. Wang C
*Scenedesmus soli* Hortobagyi C
*Scenedesmus sooi* Hortobágyi C
*Scenedesmus sooi* var. *tiszae* Uherkovich C
*Scenedesmus spicatus* West & G. S. West S
*Scenedesmus spinoso-aculeolatus* Chodat C
*Scenedesmus spinosus* var. *bicaudatus* Hortobágyi P
*Scenedesmus spinosus* var. *microspinosus* T. Hortobágyi C
*Scenedesmus spinosus* Chodat S
*Scenedesmus spinulatus* K. Biswas C
*Scenedesmus striatus* Dedusenko-Shchegoleva C
*Scenedesmus striatus* var. *apliculatus* Dedusenko-Shchegoleva C
*Scenedesmus subspicatus* Chodat S
*Scenedesmus tenuispina* Chodat S
*Scenedesmus tenuispina* var. *breviaculeatus* P. Bourrelly C
*Scenedesmus terrestris* (H. Reisigl) N. Hanagata S
*Scenedesmus tetradesmiformis* var. *pontieuxini* Uherkovich P
*Scenedesmus tetradesmiformis* (Wolosz.) Chodat P
*Scenedesmus transilvanicus* f. *regularis* (L. Péterfi) Kiriakow S
*Scenedesmus transilvanicus* Kirjakov S
*Scenedesmus tricostatus* (R. Chodat) P. Mosto P
*Scenedesmus tropicus* var. *perornatus* S
*Scenedesmus tropicus* W. B. Crow S
*Scenedesmus tschudyi* R. F. Fleming C
*Scenedesmus vacuolatus* Shihira & Krauss C
*Scenedesmus variabilis* var. *cornutus* (Franzé) De Wildeman P
*Scenedesmus velitaris* Komárek C
*Scenedesmus verrucosus* González Guerrero U
*Scenedesmus verrucosus* Y. V. Roll S
*Scenedesmus vesiculosus* f. *pseudovesiculosus* L. Péterfi P
*Scenedesmus vesiculosus* (Proshkina-Lavrenko) Péterfi C
*Scenedesmus westii* (G. M. Smith) Chodat S
*Scenedesmus wisconsinensis* (G. M. Smith) Chodat S
*Scenedesmus wisconsinensis* var. *reginae* T. Holtmann S
*Scenedesmus wuhanensis* Wei C
*Scenedesmus wuhuensis* S. S. Wang C
*Scenedesmus yiduensis* D. Zhu & L. Bi C The *Desmodesmus* genus includes, without limitation, species as follows:

*Desmodesmus abundans* (Kirchner) E. Hegewald C
*Desmodesmus abundans* var. *peruvianus* (E. Hegewald) E. Hegewald P
*Desmodesmus aculeolatus* (Reinsch) P. M. Tsarenko C
*Desmodesmus ambuehlii* (F. Hindák) E. Hegewald P
*Desmodesmus armatus* var. *boglariensis* Hortob. C
*Desmodesmus armatus* var. *subalternans* (G. M. Smith) E. Hegewald C
*Desmodesmus armatus* var. *spinosus* (F. E. Fritsch & Rich) E. Hegewald C
*Desmodesmus armatus* var. *pluricostatus* (P. Bourrelly) E. Hegewald P
*Desmodesmus armatus* var. *microspinosus* (T. Hortobágyi) E. Hegewald P
*Desmodesmus armatus* var. *longispinus* (R. Chodat) E. Hegewald C
*Desmodesmus armatus* var. *bicaudatus* (Guglielmetti) E. Hegewald C
*Desmodesmus armatus* (R. Chodat) E. Hegewald C
*Desmodesmus arthrodesmiformis* (Schröder) S. S. An, T. Friedl & E. Hegewald C
*Desmodesmus asymmetricus* (Schröder) E. Hegewald C
*Desmodesmus baconii* M. Fawley, K. Fawley & E. Hegewald C
*Desmodesmus bicaudatus* (Dedusenko) P. M. Tsarenko C
*Desmodesmus bicellularis* (R. Chodat) S. S. An, T. Friedl & E. Hegewald C
*Desmodesmus brasiliensis* var. *serrato -perforatus* (R. J. Patel & P. K. Isabella George) E. Hegewald P
*Desmodesmus brasiliensis* var. *serrato-perforatus* (R. J. Patel & P. K. Isabella George) E. Hegewald P
*Desmodesmus brasiliensis* (Bohlin) E. Hegewald P
*Desmodesmus caudato-aculeatus* (Chodat) P. M. Tsarenko C
*Desmodesmus caudato-aculeatus* var. *spinosus* (Dedusenko) P. M. Tsarenko C
*Desmodesmus communis* var. *rectangularis* (G. S. West) E. Hegewald C
*Desmodesmus communis* (E. Hegewald) E. Hegewald C
*Desmodesmus communis* var. *polisicus* P. Tsarenko & E. Hegewald C
*Desmodesmus costatogranulatus* var. *costatus* E. Hegewald & P. Tsarenko C
*Desmodesmus costatogranulatus* (Skuja) E. Hegewald C
*Desmodesmus costatogranulatus* var. *elegans* (T. Hortobágyi) E. H. Hegewald S
*Desmodesmus cuneatus* (A. P. Skabichevskij) E. Hegewald C
*Desmodesmus curvatocornis* (Proshkina-Lavrenko) E. Hegewald C
*Desmodesmus denticulatus* var. *linearis* (Hansgirg) E. Hegewald C
*Desmodesmus denticulatus* var. *fenestratus* (Teiling) E. Hegewald P
*Desmodesmus denticulatus* (Lagerheim) S. S. An, T. Friedl & E. Hegewald C
*Desmodesmus dispar* (Brébisson) E. Hegewald C
*Desmodesmus echinulatus* (Dedusenko) P. M. Tsarenko C
*Desmodesmus elegans* (Hortobágyi) E. H. Hegewald & Vanormelingen C
*Desmodesmus eupectinatus* (Dedusenko) P. M. Tsarenko C
*Desmodesmus fennicus* E. H. Hegew & Vanormelingen C
*Desmodesmus flavescens* (Chodat) E. Hegewald C
*Desmodesmus flavescens* var. *longicaudatus* (E. Hegewald) E. Hegewald P
*Desmodesmus flavescens* var. *breviaculeatus* (P. Bourrelly) E. Hegewald P
*Desmodesmus gracilis* (Matvienko) P. Tsarenko C
*Desmodesmus grahneisii* (Heynig) E. Hegewald C
*Desmodesmus granulatus* (West & G. S. West) Tsarenko C
*Desmodesmus hystricoides* (Massjuk) P. Tsarenko C
*Desmodesmus hystrix* (Lagerheim) E. Hegewald C
*Desmodesmus insignis* (West & G. S. West) E. Hegewald C
*Desmodesmus intermedius* var. *inflatus* (Svirenko) E. Hegewald C
*Desmodesmus intermedius* (Chodat) E. Hegewald C
*Desmodesmus intermedius* var. *balatonicus* (Hortobágyi) P. Tsarenko C
*Desmodesmus intermedius* var. *acutispinus* (Roll) E. Hegewald C
*Desmodesmus intermedius* var. *papillatus* (Svirenko) Pankow C
*Desmodesmus itascaensis* M. Fawley, K. Fawley & E. Hegewald C
*Desmodesmus kissii* (T. Hortobágyi) E. Hegewald P
*Desmodesmus komarekii* (E. H. Hegewald) E. H. Hegewald C
*Desmodesmus komarekii* var. *hirsutus* (F. Hindák) E. Hegewald P
*Desmodesmus lefevrei* (Deflandre) S. S. An, T. Friedl & E. H. Hegewald C
*Desmodesmus lefevrei* var. *muzzanensis* (Huber-Pestalozzi) S. S. An, T. Friedl & E. Hegewald C
*Desmodesmus lunatus* (West & G. S. West) E. Hegewald C
*Desmodesmus magnus* (Meyen) P. Tsarenko C
*Desmodesmus maximus* var. *peruviensis* (E. Hegewald) E. Hegewald P
*Desmodesmus maximus* (West & G. S. West) E. H. Hegewald C
*Desmodesmus microspina* (Chodat) P. Tsarenko C
*Desmodesmus multicauda* (Massjuk) P. Tsarenko C
*Desmodesmus multiformis* (Hegewald & Hindák) Hegewald C
*Desmodesmus multivariabilis* E. Hegewald, A. Schmidt, A. Braband, & P. Tsarenko C
*Desmodesmus multivariabilis* var. *turskensis* P. Tsarenko & E. Hegewald C
*Desmodesmus opoliensis* var. *alatus* (N. Dedusenko-Shchegoleva) E. Hegewald C
*Desmodesmus opoliensis* var. *mononensis* (Chodat) E. Hegewald C
*Desmodesmus opoliensis* (P. G. Richter) E. Hegewald C
*Desmodesmus opoliensis* var. *carinatus* (Lemmermann) E. Hegewald C
*Desmodesmus pannonicus* (Hortobágyi) E. Hegewald C
*Desmodesmus perdix* M. Fawley, K. Fawley & E. Hegewald C
*Desmodesmus perforatus* var. *spinosus* (G. Tell) E. Hegewald C
*Desmodesmus perforatus* (Lemmermann) E. Hegewald C
*Desmodesmus perforatus* f. *bicaudatus* (P. Compère) E. Hegewald P
*Desmodesmus perforatus* var. *mirabilis* C
*Desmodesmus perforatus* var. *iberaënsis* C

| | |
|---|---|
| *Desmodesmus pirkollei* E. Hegewald | C |
| *Desmodesmus pleiomorphus* (F. Hindák) E. Hegewald | P |
| *Desmodesmus polyspinosus* (T. Hortobágyi) E. Hegewald | P |
| *Desmodesmus protuberans* (F. E. Fritsch & M. F. Rich) E. Hegewald | C |
| *Desmodesmus pseudodenticulatus* (E. Hegewald) E. Hegewald | C |
| *Desmodesmus pseudohystrix* (Massjuk) P. Tsarenko | S |
| *Desmodesmus pseudoserratus* M. Fawley, K. Fawley & E. Hegewald | C |
| *Desmodesmus quadricaudatus* (Turpin)? | S |
| *Desmodesmus regularis* (L. Péterfi) E. H. Hegewald & P. Vanormelingen | C |
| *Desmodesmus santosii* E. Hegewald, K. Fawley & M. Fawley | C |
| *Desmodesmus schnepfii* (E. Hegewald & S. S. An) E. Hegewald | P |
| *Desmodesmus serrato-pectinatus* (Chodat) P. Tsarenko | C |
| *Desmodesmus serratoides* M. Fawley, K. Fawley & E. Hegewald | C |
| *Desmodesmus serratus* (Corda) S. S. An, T. Friedl & E. Hegewald | C |
| *Desmodesmus spinosus* (Chodat) E. Hegewald | C |
| *Desmodesmus spinulatus* (K. Biswas) E. Hegewald | P |
| *Desmodesmus subspicatus* (Chodat) E. Hegewald & A. Schmidt | C |
| *Desmodesmus subspicatus* var. *bicaudatus* (Proshkina-Lavrenko) P. Tsarenko | C |
| *Desmodesmus tropicus* (W. B. Crow) E. Hegewald | C |
| *Desmodesmus tropicus* var. *longiclathratus* (G. Tell) S. L. Jeon & E. Hegewald | C |
| *Desmodesmus ultrasquamatus* E. H. Hegewald & Vanormelingen | C |

The *Coelastrella* genus includes, without limitation, species *Coelastrella aeroterrestrica* A. Tschaikner, G. Gärtner & W. Kofler C, *Coelastrella corconica* (T. Kalina & M. Puncochárová) E. Hegewald & N. Hanagata C, *Coelastrella ellipsoidea* (P. M. Novis & G. Visnovksy) K. Gopalakrishnan, P. M. Novis & G. Visnovsky C, *Coelastrella levieostata* Korshikov C, *Coelastrella multistriata* var. *grandicosta* K. Gopalakrishnan, P. M. Novis & G. Visnovsky C, *Coelastrella multistriata* (Trenkwalder) Kalina & Puncochárová S, *Coelastrella multistriata* var. *corcontica* Kalina & Puncochárová C, *Coelastrella oocystiformis* (J. W. G. Lund) E. Hegewald & N. Hanagata C, *Coelastrella rubescens* (Vinatzer) Kaufnerová & Eliás C, *Coelastrella saipanensis* N. Hanagata C, *Coelastrella striata* var. *multistriata* (Trenkwalder) Kalina & Puncochárová S, *Coelastrella striolata* var. *multistriata* (Trenkwalder) Kalina & Puncochárová C, *Coelastrella striolata* Chodat C-type, *Coelastrella terrestris* (Reisigl) Hegewald & N. Hanagata C and *Coelastrella vacuolata* (I. Shihira & R. W. Krauss) Hegewald & N. Hanagata C.

More particularly, the cholorophyte belonging to the Neoehloridaceae family belongs to the *Neoehloris* genus. The *Neochloris* genus includes, without limitation, *Neochloris alveolaris* H. C. Bold S, *Neochloris aquatica* Starr C-type, *Neochloris bilobata* G. Vinatzer S, *Neochloris cohaerens* R. D. Groover & H. C. Bold S, *Neochloris conjuncta* P. A. Archibald C, *Neochloris dissecta* (Korshikov) Tsarenko C, *Neochloris fusispora* G. Arce & H. C. Bold S, *Neochloris gelatinosa* Herndon C, *Neochloris minuta* G. Arce & H. C. Bold S, *Neochloris oleoabundans* S. Chantanachat & H. C. Bold S, *Neochloris pseudoalveolaris* Deason & Bold S, *Neochloris pseudostigmatica* Bischoff & H. C. Bold C, *Neochloris pyrenoidosa* Arce & H. C. Bold C, *Neochloris terrestris* W. Herndon S, *Neochloris texensis* P. A. Archibald S, *Neochloris vigenis* Archibald C, *Neochloris vigensis* P. A. Archibald C, and *Neochloris wimmeri* (Hilse) Archibald & Bold C.

More particularly, the cholorophyte belonging to the Bracteacoccaceae family belongs to the *Bracteacoccus* genus. The *Bracteacoccus* genus includes, without limitation, *Bracteacoccus aerius* H. W. Bischoff & H. C. Bold C, *Bracteacoccus aggregatus* Tereg C-type, *Bracteacoccus anomalus* (E. J. James) R. C. Starr U, *Bracteacoccus bohemiensis* Fuciková, Fletchner & L. A. Lewis C, *Bracteacoccus bullatus* Fuciková, Fletchner & L. A. Lewis C, *Bracteacoccus cinnabarinus* (Kol & F. Chodat) Starr S, *Bracteacoccus cohaerens* H. W. Bischoff & H. C. Bold S, *Bracteacoccus deserticola* Fuciková, Fletchner & L. A. Lewis C, *Bracteacoccus engadinensis* (Kol & F. Chodat) Starr S, *Bracteacoccus gametifer* (Chodat) Starr U, *Bracteacoccus gerneckii* (Wille) Starr U, *Bracteacoccus giganteus* H. W. Bischoff & H. C. Bold C, *Bracteacoccus glacialis* Fuciková, Fletchner & L. A. Lewis C, *Bracteacoccus grandis* H. W. Bischoff & H. C. Bold C, *Bracteacoccus helveticus* (Kol & F. Chodat) Starr U, *Bracteacoccus irregularis* (J. B. Petersen) Starr S, *Bracteacoccus medionucleatus* H. W. Bischoff & H. C. Bold C, *Bracteacoccus minor* (Chodat) Petrová C, *Bracteacoccus minor* var. *desertorum* Friedmann & Ocampo-Paus C, *Bracteacoccus minor* var. *glacialis* E. A. Flint S, *Bracteacoccus minutus* Schwarz S, *Bracteacoccus occidentalis* Fuciková, Fletchner & L. A. Lewis C, *Bracteacoccus polaris* Fuciková, Fletchner & L. A. Lewis C, *Bracteacoccus pseudominor* H. W. Bischoff & H. C. Bold C, *Bracteacoccus terrestris* (Kol & F. Chodat) Starr S, and *Bracteacoccus xerophilus* Fuciková, Fletchner & L. A. Lewis C.

More particularly, the cholorophyte belonging to the Selenastraceae family belongs to the *Ankistrodesmus* genus. The *Ankistrodesmus* genus includes, without limitation, the following species:

| | |
|---|---|
| *Ankistrodesmus acerosus* Komárek & Comas González | C |
| *Ankistrodesmus acicularis* var. *heteropolis* Skuja | P |
| *Ankistrodesmus acicularis* (Braun) Korshikov | S |
| *Ankistrodesmus acicularis* var. *mirabilis* (West & G. S. West) Korshikov | S |
| *Ankistrodesmus acicularis* var. *stipitatus* Korshikov | C |

-continued

*Ankistrodesmus acutissimus* Wm. Archer P
*Ankistrodesmus amalloides* Chodat & Oettli P
*Ankistrodesmus angustus* C. Bernard S
*Ankistrodesmus antarcticus* Kol & E. A. Flint C
*Ankistrodesmus arcticus* Prescott P
*Ankistrodesmus arcuatus* Korshikov S
*Ankistrodesmus bernardensis* Chodat & Oettli C
*Ankistrodesmus bernardii* Komárek C
*Ankistrodesmus bibraianus* (Reinsch) Korshikov S
*Ankistrodesmus biplexus* (Reinsch) Hortobagyi S
*Ankistrodesmus braunii* (Nägeli) Lemmermann S
*Ankistrodesmus braunii* var. *pygmaeus* Printz P
*Ankistrodesmus braunii* var. *minutus* Playfair C
*Ankistrodesmus braunii* f. *tarfosum* Chodat P
*Ankistrodesmus braunii* var. *pusillus* Printz S
*Ankistrodesmus braunii* var. *pusillus* Printz P
*Ankistrodesmus braunii* var. *lacustris* (Chodat) Chodat P
*Ankistrodesmus caribeum* (Hindák) Ergashev P
*Ankistrodesmus chlorogonioides* Guglielmetti C
*Ankistrodesmus chodatii* (Tanner-Fullman) Brunnthaler S
*Ankistrodesmus closterioides* var. *pfitzeri* (Schroeder) Ergashev P
*Ankistrodesmus closterioides* (Bohlin) Printz S
*Ankistrodesmus contortus* Thuret S
*Ankistrodesmus contortus* f. *minor* Wille P
*Ankistrodesmus convolutus* var. *obtusus* Printz P
*Ankistrodesmus convolutus* var. *minutus* (Nägeli) Rabenhorst P
*Ankistrodesmus convolutus* Corda S
*Ankistrodesmus cucumiformis* J. H. Belcher & Swale C
*Ankistrodesmus curvulus* J. H. Belcher & Swale S
*Ankistrodesmus densus* Korshikov C
*Ankistrodesmus dulcis* Playfair C
*Ankistrodesmus dulcis* var. *cingulum* Playfair C
*Ankistrodesmus dybowskii* (Woloszynska) Ergashev P
*Ankistrodesmus ecsediensis* Hortobágyi P
*Ankistrodesmus extensus* Korshikov C
*Ankistrodesmus falcatus* var. *mirabilis* West & G. S. West S
*Ankistrodesmus falcatus* var. *fasciculatus* Margalef P
*Ankistrodesmus falcatus* f. *terrestris* Bristol S
*Ankistrodesmus falcatus* var. [*mirabilis*] f. *dulcis* C
*Ankistrodesmus falcatus* f. *elongatus* Komárková-Legnerová P
*Ankistrodesmus falcatus* var. *turfosus* (Chodat) Korshikov C
*Ankistrodesmus falcatus* var. *serians* (Zach.) Lemmermann P
*Ankistrodesmus falcatus* var. *bifurcatus* Palik P
*Ankistrodesmus falcatus* var. *anguineus* (Hansgirg) Guglielmetti P
*Ankistrodesmus falcatus* f. *stipitata* Korshikov P
*Ankistrodesmus falcatus* f. *serians* (Zacharias) Teiling P
*Ankistrodesmus falcatus* f. *pererrans* Beck-Mannagetta P
*Ankistrodesmus falcatus* f. *marthiae* Kammerer P
*Ankistrodesmus falcatus* f. *longissimus* Printz P
*Ankistrodesmus falcatus* f. *longisetus* Nygaard P
*Ankistrodesmus falcatus* f. *hagmanniorum* Kammerer P
*Ankistrodesmus falcatus* f. *gigas* Cholnok P
*Ankistrodesmus falcatus* f. *elongatus* Nygaard P
*Ankistrodesmus falcatus* f. *dulcis* (Playfair) Nygaard P
*Ankistrodesmus falcatus* f. *brevis* Nygaard P
*Ankistrodesmus falcatus* var. *spiralis* (W. B. Turner) G. S. West S
*Ankistrodesmus falcatus* var. *spiralis* (W. B. Turner) K. Möbius S
*Ankistrodesmus falcatus* var. *biplex* (Reinsch) G. S. West P
*Ankistrodesmus falcatus* (Corda) Ralfs C
*Ankistrodesmus falcatus* var. *radiatus* (Chodat) Lemmermann P
*Ankistrodesmus falcatus* var. *contortus* (Thuret) Playfair S
*Ankistrodesmus falcatus* var. *setiforme* Nygaard S
*Ankistrodesmus falcatus* var. *setigerus* (Schröder) G. S. West P
*Ankistrodesmus falcatus* var. *gracile* P
*Ankistrodesmus falcatus* var. *tumidus* (West & West) G. S. West S
*Ankistrodesmus falcatus* var. *spirilliformis* G. S West S
*Ankistrodesmus falcatus* var. *duplex* (Kützing) G. S. West S
*Ankistrodesmus falcatus* var. *stipitatus* (Chodat) Lemmermann S
*Ankistrodesmus falcatus* var. *acicularis* (A. Braun) G. S. West S
*Ankistrodesmus falciformis* Sokoloff P
*Ankistrodesmus fasciculatus* (Lundberg) Komárková-Legnerová C
*Ankistrodesmus fasciculatus* var. *turfosus* (Chodat) Vischer P
*Ankistrodesmus flexuosus* f. *longisetus* (Nygaard) Ergashev P
*Ankistrodesmus flexuosus* (Komárek) Ergashev P
*Ankistrodesmus fractus* (West & G. S. West) Collins C
*Ankistrodesmus fusiformis* Corda ex Korshikov C - type
*Ankistrodesmus fusiformis* f. *stipitatus* Korshikov P
*Ankistrodesmus gelifactum* (Chodat) Bourrelly S
*Ankistrodesmus gelifactus* (Chodat) Bourrelly S

*Ankistrodesmus genevensis* Reverdin S
*Ankistrodesmus gracilis* var. *giganteus* Thérézien P
*Ankistrodesmus gracilis* (Reinsch) Korshikov C
*Ankistrodesmus hindakii* (Hindák) Ergashev P
*Ankistrodesmus komarekii* (Komárek) Ergashev P
*Ankistrodesmus lacuster* (Chodat) Ostenfeld P
*Ankistrodesmus lacustris* (Chodat) Ostenfeld S
*Ankistrodesmus longissimus* (Lemmermann) Wille S
*Ankistrodesmus longissimus* var. *septatum* (Chodat) Komárková-Legnerová C
*Ankistrodesmus longissimus f. minor* Hortobágyi P
*Ankistrodesmus longissimus f. minor* Huber-Pestalozzi P
*Ankistrodesmus longissimus* var. *rostafinskii* Kol P
*Ankistrodesmus longissimus* var. *africanus* (Hindák) Ergashev P
*Ankistrodesmus longissimus* var. *tenuissimum* (G. M. Smith) Bourrelly P
*Ankistrodesmus lundbergii* Koshikov S
*Ankistrodesmus lunulatus* J. H. Belcher & Swale S
*Ankistrodesmus marinus* Butcher C
*Ankistrodesmus mayorii* G. S. West S
*Ankistrodesmus minutissimus* Korshikov S
*Ankistrodesmus minutus* (Nägeli) Chodat P
*Ankistrodesmus mirabilis* (West & G. S. West) Lemmermann S
*Ankistrodesmus mucosus* Korshikov S
*Ankistrodesmus nannoselene* Skuja S
*Ankistrodesmus nitzschioides* var. *crysia* Szalai P
*Ankistrodesmus nitzschioides* var. *spiralis* Printz S
*Ankistrodesmus nitzschioides* G. S. West S
*Ankistrodesmus nivalis* Chodat P
*Ankistrodesmus obtusus* Korshikov S
*Ankistrodesmus pehrii* Beck-Mannagetta P
*Ankistrodesmus pfitzeri* (Schröder) G. S. West S
*Ankistrodesmus polymorphus* (Fresenius) Sámano, Bishop, & Sokoloff P
*Ankistrodesmus pseudobraunii* J. H. Belcher & Swale S
*Ankistrodesmus pseudomirabilis* Korshikov S
*Ankistrodesmus pseudomirablis* var. *spiralis* Korshikov S
*Ankistrodesmus pseudosabulosum* (Hindák) Ergashev P
*Ankistrodesmus pyrenogerum* (Chodat) Guarrera & Khnemann P
*Ankistrodesmus quaternatus* West & G. S. West S
*Ankistrodesmus quaternus* West & G. S. West C
*Ankistrodesmus rhaphidioides* (Hansgirg) Ergashev P
*Ankistrodesmus rotundus* Korshikov S
*Ankistrodesmus sabrinensis* J. H. Belcher & Swale S
*Ankistrodesmus selenastrum* West C
*Ankistrodesmus septatus* Chodat & Oettli P
*Ankistrodesmus septatus* Oettli P
*Ankistrodesmus setigerus f. minor* G. S. West C
*Ankistrodesmus setigerus* (Schröder) G. S. West S
*Ankistrodesmus setigerus* var. *undosus* Hortobágyi P
*Ankistrodesmus setigerus* var. *multipyrenoidus* Hortobágyi P
*Ankistrodesmus setigerus* var. G. S Hortobágyi P
*Ankistrodesmus sigmoideus* (Rabenhorst) Brühl & Biswas P
*Ankistrodesmus spiralis* var. *fasciculatus* G. M. Smith S
*Ankistrodesmus spiralis* (W. B. Turner) Lemmermann C
*Ankistrodesmus spirochromus* (Reverdin) Reverdin P
*Ankistrodesmus spirotaenia* G. S. West S
*Ankistrodesmus stipitatus* (Chodat) Komárková-Legnerová P
*Ankistrodesmus subcapitatus* Korshikov S
*Ankistrodesmus subtilis* Hindák S
*Ankistrodesmus tatrae* Kol S
*Ankistrodesmus tjibodensis* (Bernard) Printz P
*Ankistrodesmus tortilis* West & G. S. West S
*Ankistrodesmus tortus* Komárek & Comas González C
*Ankistrodesmus turneri* (West & G. S. West) Komárek & Comas González P
*Ankistrodesmus viretii* (Chodat) Chodat S
*Ankistrodesmus viretii* Chodat P
*Ankistrodesmus viridis* (J. Snow) Bourrelly S In a more particular embodiment, the chlorophyte belonging to the Chlamydomonadciles order is a chlorophyte belonging to Dunaliellaceae family, to the Haematococcaceae family, to the Palmellopsidaceae family, or to the Chlorococcaceae family.

More particularly, the cholorphyte belonging to the Dunaliellaceae family belongs to the *Dunaliella* genus. The *Dunaliella* genus includes, without limitation, *Dunaliella acidophila*, *Dunaliella bardawil*, *Dunaliella bioculata*, *Dunaliella lateralis*, *Dunaliella maritime*, *Dunaliella minuta*, *Dunaliella parva*, *Dunaliella peircei*, *Dunaliella polymorpha*, *Dunaliella primolecta*, *Dunaliella pseudosalina*, and *Dunaliella quartolecta*. Particularly preferred species include, without limitation, *Dunaliella acidophila* (Kalina) Massyuk C, *Dunaliella assymetica* Massyuk C, *Dunaliella baasbecldngii* Massyuk C, *Dunaliella bardawil* Ben-Amotz & Avron S, *Dunaliella bioculata* Bucher C, *Dunaliella carpatica* Massyuk C, *Dunaliella cordata* Pascher & Jahoda S, *Dunaliella euchlora* Lerche S, *Dunaliella gracilis* Massyuk C, *Dunaliella granulata* Massyuk C,

*Dunaliella lateralis* Pascher & Jahoda C, *Dunaliella maritima* Massyuk C, *Dunaliella media* Lerche C, *Dunaliella minuta* W. Lerche C, *Dunaliella parva* W. Lerche C, *Dunaliella peircei* Nicolai & Baas-Becking C, *Dunaliella polymorpha* Butcher C, *Dunaliella primolecta* Butcher C, *Dunaliella pseudosalina* Massyuk & Radchenko C, *Dunaliella quartolecta* Butcher C, *Dunaliella ruineniana* Massyuk C, *Dunaliella salina* (Dunal) Teodoresco C-type, *Dunaliella terricola* Massyuk C, *Dunaliella tertiolecta* Butcher C, *Dunaliella turcomanica* Massyuk C, *Dunaliella viridis* var. *palmelloides* Massyuk C, *Dunaliella viridis* Teodoresco C, and *Dunaliella viridis* f. euchlora (Lerche) Massyuk S. Preferably, the cholorophyte belonging to the *Dunaliella* genus is *Dunaliella salina*.

More particularly, the cholorophyte belonging to the Haematococcaceae family belongs to the *Haematococcus* genus. The *Haematococcus* genus includes, without limitation, *Haematococcus capensis, Haematococcus carocellus, Haematococcus droebakensis, Haematococcus lacustris, Haematococcus murorum, Haematococcus pluvialis, Haematococcus thermalis* and *Haematococcus zimbabwiensis*. Particularly preferred species include, without limitation, *Haematococcus allmanii* Hassall S, *Haematococcus buetschlii* Blochmann S, *Haematococcus capensis* var. *novae-zelandiae* Pocock C, *Haematococcus capensis* var. *piriformis f. caudata* Pocock P, *Haematococcus capensis* Pocock S, *Haematococcus capensis* var. *piriformis* Pocock P, *Haematococcus capensis* var. *torpedo* Pocock P, *Haematococcus carocellus* R. H. Thompson & D. E. Wujek C, *Haematococcus droebakensis* Wollenweber S, *Haematococcus droebakensis* var. *fastigatus* Wollenweber C, *Haematococcus grevillei* C. Agardh S, *Haematococcus hookeriana* Berkeley & Hassall S, *Haematococcus insignis* Hassall S, *Haematococcus lacustris* (Girod-Chantrans) Roststafinski S, *Haematococcus murorum* Hassall C, *Haematococcus pluvialis* Flotow C-type, *Haematococcus salinus* Dunal S, *Haematococcus sanguineus* C. Agardh S, *Haematococcus thermalis* Lemmermann C, and *Haematococcus zimbabwiensis* Pockock C. Preferably, the cholorophyte belonging to the *Haematococcus* genus is *Haematococcus pluvialis*.

More particularly, the cholorophyte belonging to the Palmellopsidaceae family belongs to the *Chlamydocapsa* genus. The *Chlamydocapsa* genus includes, without limitation, *Chlamydocapsa ampla* (Kützing) Fott C-type, *Chlamydocapsa bacillus* (Teiling) Fott C, *Chlamydocapsa lobata* Broady C, *Chlamydocapsa maxima* (Mainx) Ettl & Gärtner C, *Chlamydocapsa mucifera* Hindák C, *Chlamydocapsa planctonica* (West & G. S. West) Fott C, and *Chlamydocapsa retrospectans* Fiddian C.

More particularly, the chlorophyte belonging to the Chlorococcaceae family belongs to the *Chlorococcum* genus. The *Chlorococcum* genus includes, without limitation, *Chlorococcum acidum, Chlorococcum aegyptiacum, Chlorococcum botryoides, Chlorococcum choloepodis, Chlorococcum citriforme, Chlorococcum costatozygotum, Chlorococcum diplobionticum, Chlorococcum dissectum, Chlorococcum echinozygotum, Chlorococcum elbense, Chlorococcum elkhartiense, Chlorococcum ellipsoideum, Chlorococcum hypnosporum, Chlorococcum infusionum, Chlorococcum isabeliense, Chlorococcum lobatum, Chlorococcum macrostigmatum, Chlorococcum minimum, Chlorococcum minutum, Chlorococcum novae-angliae, Chlorococcum oleofaciens, Chlorococcum olivaceum, Chlorococcum pamirum, Chlorococcum pinguideum, Chlorococcum polymorphum, Chlorococcum pseudodictyosphaerium, Chlorococcum pyrenoidosum, Chlorococcum refringens, Chlorococcum salinum, Chlorococcum schizochlamys, Chlorococcum schwarzii, Chlorococcum submarinum, Chlorococcum tatrense* and *Chlorococcum vacuolatum*. Particularly preferred chlorophytes belonging to the *Chlorococcum* genus include *Chlorococcum acidum* P. A. Archibald & H. C. Bold C, *Chlorococcum aegyptiacum* P. A. Archibald C, *Chlorococcum africanum* Reinsch C, *Chlorococcum aplanosporum* Arce & Bold S, *Chlorococcum aquaticum* Archibald S, *Chlorococcum arenosum* Archibald & Bold S, *Chlorococcum aureurn* Archibald & Bold S, *Chlorococcum botryoides* Rabenhorst C, *Chlorococcum chlorococcoides* (Korshikov) Philipose C, *Chlorococcum choloepodis* (J. Kühn) D. E. Wujek & P. Timpano C, *Chlorococcum choloepodis* (J. Kühn) R. Thompson P, *Chlorococcum citriforme* Archibald & Bold C, *Chlorococcum compactum* Ettl & Gärtner S, *Chlorococcum costatozygotum* Ettl & Gärtner C, *Chlorococcum croceum* Archibald & Bold S, *Chlorococcum diplobionticoideum* Chantanachat & Bold S, *Chlorococcum diplobionticum* Herndon C, *Chlorococcum dissectum* Korshikov S, *Chlorococcum echinozygotum* Starr C, *Chlorococcum elbense* Archibald C, *Chlorococcum elkhartiense* P. A. Archibald & H. C. Bold C, *Chlorococcum ellipsoideum* Deason & H. C. Bold C, *Chlorococcum ellipsoideum* (Korshikov) Philipose S, *Chlorococcum fissum* P. A. Archibald & H. C. Bold C, *Chlorococcum gelatinosum* P. A. Archibald & H. C. Bold S, *Chlorococcum gigas* (Kützing) Grunow S, *Chlorococcum granulosum* Archibald S, *Chlorococcum humicola* var. *incrassatum* F. E. Fritsch & R. P. John S, *Chlorococcum humicola* (Nägeli) Rabenhorst S, *Chlorococcum hypnosporum* Starr C, *Chlorococcum infusionum* var. *macrostigmatica* L. Moewus C, *Chlorococcum infusionum* (Schrank) Meneghini C-type, *Chlorococcum intermedium* Deason & Bold S, *Chlorococcum isabeliense* P. A. Archibald & H. C. Bold C, *Chlorococcum lacustre* Archibald & Bold S, *Chlorococcum littorale* M. Chihara, T. Nakayama & I. Inouye C, *Chlorococcum lobatum* (Korshikov) F. E. Fritsch & R. P. John C, *Chlorococcum loculatum* Archibald & Bold S, *Chlorococcum macrostigmatum* R. C. Starr C, *Chlorococcum microstigmatum* Archibald & Bold S, *Chlorococcum minimum* Ettl & Gärtner C, *Chlorococcum minutum* R. C. Starr C, *Chlorococcum multinucleatum* Starr S, *Chlorococcum murorum* Greville C, *Chlorococcum nivale* Archibald S, *Chlorococcum novae-angliae* P. A. Archibald & H. C. Bold C, *Chlorococcum olefaciens* Trainor P, *Chlorococcum oleofaciens* Trainor & H. C. Bold C, *Chlorococcum olivaceum* Rabenhorst P, *Chlorococcum oviforme* Archibald & Bold S, *Chlorococcum paludosum* Archibald & Bold S, *Chlorococcum pamirum* P. A. Archibald C, *Chlorococcum papillatum* Demczenko C, *Chlorococcum perforatum* Arce & Bold S, *Chlorococcum perplexum* Archibald & Bold S, *Chlorococcum pinguideum*

Arce & H. C. Bold C, *Chlorococcum pleiopyrenigerum* (L. Moewus) Ettl & Gärtner C, *Chlorococcum polymorphum* Bischoff & Bold S, *Chlorococcum pseudodictyosphaerium* Metting C, *Chlorococcum pulchrum* Archibald & Bold S, *Chlorococcum punctatum* Arce & H. C. Bold S, *Chlorococcum pyrenoidosum* P, *Chlorococcum refringens* P. A. Archibald & H. C. Bold S, *Chlorococcum regulare* West S, *Chlorococcum reticulatum* Archibald & Bold S, *Chlorococcum robustum* Ettl & Gärtner S, *Chlorococcum rugosum* Archibald & Bold S, *Chlorococcum salinum* Archibald C, *Chlorococcum salsugineum* Archibald & Bold S, *Chlorococcum scabellum* Deason & Bold S, *Chlorococcum schizochlamys* (Korshikov) Philipose C, *Chlorococcum schwarzii* Ettl & Gärtner C, *Chlorococcum sphacosum* Archibald & Bold S, *Chlorococcum starrii* Trainor & Verses S, *Chlorococcum submarinum* Ålvik C, *Chlorococcum tatrense* Archibald C, *Chlorococcum tetrasporum* Arce & Bold S, *Chlorococcum texanum* Archibald & Bold S, *Chlorococcum typicum* Archibald & Bold S, *Chlorococcum uliginosum* Archibald & Bold S, *Chlorococcum vacuolatum* R. C. Starr C, *Chlorococcum viride* (C. Agardh) Chevallier P, *Chlorococcum vitiosum* Printz C, and *Chlorococcum wimmeri* (F. W. Hilse) Rabenhorst C.

In a particular embodiment, the chlorophyte belonging to the Chlorodendrophyceae class is a chlorophyte belonging to the Chlorodendrales order, more particularly to the Chlorodendraceae family. Preferably, the chlorophyte belonging to the Chlorodendraceae family belongs to the *Tetraselmis* genus. The *Tetraselmis* genus includes, without limitation, *Tetraselmis alacris* Butcher C, *Tetraselmis apiculata* (Butcher) Butcher C, *Tetraselmis arnoldii* (Proshkina-Lavrenko) R. E. Norris, Hori & Chihara C, *Tetraselmis ascus* (Proskauer) R. E. Norris, Hori & Chihara C, *Tetraselmis astigmatica* R. E. Norris & Hori C, *Tetraselmis bichlora* (H. Ettl & O. Ettl) R. E. Norris, Hori & Chihara S, *Tetraselmis bilobata* (Roukhiyajnen) R. E. Norris, Hori & Chihara C, *Tetraselmis bolosiana* (Margalef) R. E. Norris, Hori & Chihara C, *Tetraselmis chui* Butcher C, *Tetraselmis contracta* (N. Carter) Butcher C, *Tetraselmis convolutae* (Parke & Manton) R. E. Norris, Hori & Chihara S, *Tetraselmis cordiformis* (H. J. Carter) Stein C-type, *Tetraselmis desikacharyi* Marin, Hoef-Emden & Melkonian C, *Tetraselmis elliptica* (G. M. Smith) R. E. Norris, Hori & Chihara C, *Tetraselmis fontiana* (Margalef) R. E. Norris, Hori & Chihara C, *Tetraselmis gracilis* (Kylin) Butcher C, *Tetraselmis hazenii* Butcher C, *Tetraselmis helgolandica* (Kylin) Butcher C, *Tetraselmis helgolandica* var. *tsingtaoensis* (C. K. Tseng & T. J. Chang) R. E. Norris, T. Hori & M. Chihara C, *Tetraselmis impellucida* (McLachlan & Parke) R. E. Norris, Hori & Chihara C, *Tetraselmis incisa* (Nygaard) R. E. Norris, Hori & Chihara S, *Tetraselmis inconspicua* Butcher C, *Tetraselmis indica* Arora & Anil C, *Tetraselmis levis* Butcher C, *Tetraselmis limnetis* Stokes C, *Tetraselmis maculata* Butcher C, *Tetraselmis marina* (Cienkowski) R. E. Norris, Hori & Chihara C, *Tetraselmis mediterranea* (Lucksch) R. E. Norris, Hori & Chihara C, *Tetraselmis micropapillata* (Ålvik) Butcher C, *Tetraselmis rubens* Butcher S, *Tetraselmis striata* Butcher C, *Tetraselmis subcordiformis* (Wille) Butcher C, *Tetraselmis suecica* (Kylin) Butcher C, *Tetraselmis tetrabrachia* C, *Tetraselmis tetrathele* (West) Butcher C, *Tetraselmis verrucosa* f. *rubens* (Butcher) Hori, Norris & Chihara C, *Tetraselmis verrucosa* Butcher C, *Tetraselmis viridis* (Rouchijajnen) R. E. Norris, Hori & Chihara C, and *Tetraselmis wettsteinii* (J. Schiller) Throndsen C.

Phylum Heterokontophyta

The phylum Heterokontophyta relates to a division of algae comprising the heterokontophytes, which show a motile life cycle stage, in which the flagellate cells possess two differently shaped flagella. In a particular embodiment, the heterokontophyte of the phylum Heterokontophyta is a heterokontophyte belonging to the Coscinodiscophyceae class, to the Eustigmatophyceae class, or to the Labyrinthulomycetes class. In a particular embodiment, the heterokontophyte of the phylum Heterokontophyta is a microalga. In a particular embodiment, the heterokontophyte of the phylum Heterokontophyta is a microalga.

In a particular embodiment, the heterokontophyte belonging to the Coscinodiscophyceae class is a heterokontophyte belonging to the Thalassiosirales order, more particularly to the Thalassiosiraceae family or to the Skeletonemaceae family.

In a particular embodiment, the heterokontophyte of the Thalassiosiraceae family belongs to the *Thalassiosira* genus. The *Thalassiosira* genus includes, without limitation, *Thalassiosira pseudonana*, *Thalasiosira aestivalis*, *Thalassiosira antartica*, *Thalassiosira ambigua*, *Thalassiosira punctigera*, *Thalassiosira weissflogii*, *Thalassiosira rotula*, *Thalassiosira eccentric*, *Thalassiosira gravida*, *Thalassiosira decipiens*, *Thalassiosira floridana*, *Thalassiosira guillardii*, *Thalassiosira hyaline*, *Thalassiosira minima*, *Thalassiosira minuscula nordenskioeldii nordenskioeldii*, *Thalassiosira oceanica*, *Thalassiosira* sp, and *Thalassiosira tumida*. A particularly preferred species is *Thalassiosira pseudonana*.

In a particular embodiment, the heterokontophyte of the Skeletonemaceae family belongs to the *Skeletonema* genus. The *Skeletonema* genus includes, without limitation, *Skeletonema barbadense* Greville C-type, *Skeletonema costatum* (Greville) Cleve C, *Skeletonema denticulatum* N. I. Strelnikova C, *Skeletonema dohrnii* Sarno & Kooistra C, *Skeletonema grethae* Zingone & Sarno C, *Skeletonema grevillei* Sarno & Zingone C, *Skeletonema japonicum* Zingone & Sarno C, *Skeletonema marinoi* Sarno & Zingone C, *Skeletonema menzelii* Guillard, Caipenter & Reimann C, *Skeletonema mirabile* Grunow ex Van Heurck C, *Skeletonema munzelii* Guillard, Carpeuter & Reimann, C, *Skeletonema penicillus* Grunow C, *Skeletonema potamos* (C. I. Weber) Hasle C, *Skeletonema probabile* A. P. Jousé C, *Skeletonema pseudocostatum* L. K. Medlin C, *Skeletonema simbirskianum* A. Schmidt C, *Skeletonema stylifera* Brun C, *Skeletonema subsalsum* (Cleve-Euler) Bethge C, *Skeletonema tropicum* Cleve C, *Skeletonema utriculosa* Brun C, *Skeletonema ventricosum* N. W. Anissimowa C, *Skeletonema ardens* Sarno & Zingone C, and *Skeletonema* sp.

In a particular embodiment, the heterokontophyte belonging to the Eustigmatophyeeae class is a heterokontophyte belonging to the Eustigmatales order, more particularly to the Eustigmataceae family. Preferably, the heterokontophyte of the Eustigmataceae family belongs to the *Nannochloropsis* genus. The *Nannochloropsis* genus includes, without limitation, *Nannochloris atomus*, *Nannochloris coccoides*, *Nannochloropsis gaditana*, *Nannochloropsis granulate*, *Nannochloropsis limnetica*, *Nannochloropsis limnetica* var. *dystrophica*, *Nannochloropsis limnetica* var. *globosa*, *Nannochloropsis limnetica* var. *gutta*, *Nannochloropsis lim-* netica var. irregularis, Nannochloris maculate, Nannochloropsis maritime, Nannochloropsis oceanica, Nannochloropsis oculata, Nannochloropsis salina, and Nannochloropsis sp. A particularly preferred species is Nannochloropsis gaditana.

In a particular embodiment, the heterokontophyte belonging to the Labyrinthulomycetes class is a heterokontophyte belonging to the Labyrinthulales order, more particularly to the Thraustochytriceae family or to the Labyrinthulae family.

In a particular embodiment, the heterokontophyte of the Thraustochytriceae are selected from *Schizochytrium* genus, *Aurantochytrium* genus, *Aplanochytrium* genus, *Oblongichytrium* genus, *Sycyoidochytrium* genus, *Botryochytrium* genus, *Parietichytrium* genus, *Traustochytrium* genus, and *Ulkenia* genus.

The *Schizochytrium* genus includes, without limitation, *Schizochytrium* sp., *Schizochytrium limacinum*, and *Schizochytrium aggregatum*.

The *Aurantochytrium* genus includes, without limitation, *Aurantiochytrium* sp., *Aurantiochytrium limacinum*, and *Aurantiochytrium mangrovei*.

The *Aplanochytrium* genus includes, without limitation, *Aplanochytrium* sp., *Aplanochytrium kerguelense*, *Aplanochytrium minutum*, and *Aplanochytrium stocchinoi*.

The *Oblongichytrium* genus includes, without limitation, *Oblongichytrium* sp., *Oblongichytrium minutum*, and *Oblongichytrium multirudimentali*.

The *Sycyoidochytrium* genus includes, without limitation, *Sicyoidochytrium minutum*, and *Sicyoidochytrium* sp.

The *Botryochytrium* genus includes, without limitation, *Botryochytrium* sp., and *Botryochytrium radiatum*.

The *Parietichytrium* genus includes, without limitation, *Parietichytriurm* sp., and *Parietichytriurm sarkarianum*.

The *Traustochytrium* genus includes, without limitation, *Traustochytrium roseum*, *Traustochytrium* sp., *Traustochytrium aggregatum*, *Traustochytrium aureum*, *Traustochytrium kinnei*, *Traustochytrium pachydermum*, and *Traustochytrium striatum*.

The *Ulkenia* includes, without limitation, *Ulkenia* sp., *Ulkenia ameboidea*, *Ulkenia profunda*, and *Ulkenia visurgensis*.

In a particular embodiment, the heterokontophyte of the Labyrinthulae family belongs to the *Labyrinthula* genus. The *Labyrinthula* genus includes, without limitation, *Labyrinthula* sp.

Thus, according to the method for the production of chitosan of the invention, the algal biomass belongs to algae belonging to the phylum Haptophyta, to the phylum Chlorophyta, or to the phylum Heterokontophyta.

In particular, the algae belonging to the phylum Haptophyta are selected from algae belonging to the Prymnesiophyceae class or to the Pavlovophyceae class, the algae belonging to the phylum Chlorophyta are selected from algae belonging to the Trebouxiophyceae class, to the Chlorophyceae class, or to the Chlorodendrophyceae class, and the algae belonging to the phylum Heterokontophyta are selected from algae belonging to the Coscinodiscophyceae class, to the Enstigmatophyceae class, or to the Labyrinthulomycetes class.

More in particular, the algae belonging to the Prymnesiophyceae class are selected from algae belonging to the Isochrysidales order, the algae belonging to the Pavlovophyceae class are selected from algae belonging to the Pavlovales order, the algae belonging to the Trebouxiophyceae class are selected from algae belonging to the Chlorellales order, the algae belonging to the Chlorophyceae class are selected from algae belonging to the Sphaeropleales order or to the Chlamydomonadales order, the algae belonging to the Chlorodendrophyceae class are selected from algae belonging to the Chlorodendrales order, the algae belonging to the Coscinodiscophyceae class are selected from algae belonging to Thalassiosirales order, the algae belonging to the Eustigmatophyceae class are selected from algae belonging to Eustigmatales order, and the algae belonging to the Labyrinthulomycetes class are selected from algae belonging to Labyrinthulales order.

More in particular, the algae belonging to the Isochrysidales order are selected from algae belonging to the Isochrysidaceae family or to the Noelaerhabdaceae family, the algae belonging to the Pavlovales order are selected from algae belonging to the Pavlovaceae family, the algae belonging to the Chlorellales order are selected from algae belonging to the Chlorellaceae family, the algae belonging to the Sphaeropleales order are selected from algae belonging to the Scenedesmaceae family, to the Neochloridaceae family, to the Bracteacoccaceae family, or to the Selenastraceae family, the algae belonging to the Chlamydomonadales order are selected from algae belonging to the Dunaliellaceae family, to the Haematococcaceae family, to the Palmellopsidaceae family, or to the Chlorococcaceae family, the algae belonging to the Chlorodendrales order are selected from algae belonging to the Chlorodendraceae family, the algae belonging to the Thalassiosirales order are selected from algae belonging to the Thalassiosiraceae family or to the Skeletonemaceae family, the algae belonging to the Eustigmatales order are selected from algae belonging to the Eustigmataceae family, and the algae belonging to the Labyrinthulales order are selected from algae belonging to the Thraustochytriceae family or to the Labyrinthulae family.

Even more in particular, the algae belonging to Isochrysidaceae family are selected from algae belonging to the *Isochrysis* genus or to the *Tisochrysis* genus, the algae belonging to Noelaerhabdaceae family are selected from algae belonging to the *Emiliania* genus, the algae belonging to the Pavlovaceae family are selected from algae belonging to the *Pavlova* genus, the algae belonging to Chlorellaceae family are selected from algae belonging to the *Chlorella* genus, to the *Helicosporidium* genus, to the *Chlorella* genus, to the *Muriella* genus, to the *Prototheca* genus, to the *Nannochloris* genus, or to the *Micractinium* genus, the algae belonging to Scenedesmaceae family are selected from algae belonging to the *Scenedesmus* genus, to the *Desmodesmus* genus, or to the *Coelastrella* genus, the algae belonging to the Neochloridaceae family are selected from algae belonging to the *Neochloris* genus, the algae belonging to the Bracteacoccaceae family are selected from algae belonging to the *Bracteacoccus* genus, the algae belonging to the Selenastraceae family are selected from algae belonging to the *Ankistrodesmus* genus, the algae belonging to Dunaliellaceae family are selected from algae belonging to the *Dunaliella* genus, the algae belonging to Haematococcaceae family are selected from algae belonging to the *Haematococcus* genus, the algae belonging to the Palmellopsidaceae family are selected from algae belonging to the *Chlamydocapsa* genus, the algae belonging to Chlorococcaceae family are selected from algae belonging to the *Chlorococcum* genus, the algae belonging to Chlorodendraceae family are selected from algae belonging to the *Tetraselmis* genus, the algae belonging to Thalassiosiraceae family are selected from algae belonging to the *Thalassiosira* genus, the algae belonging to Skeletonemaceae family are selected from algae belonging to the *Skeletonema* genus, the algae belonging to Eustigmataceae family are selected from algae belonging to the *Nannochloropsis* genus, the algae belonging to Thraustochytriceae family are selected from algae belonging to the *Schizochytrium* genus, *Aurantochytrium* genus, *Aplanochytrium* genus, *Oblongichytrium* genus, *Sycyoidochytrium* genus, *Botryochytrium* genus, *Parietichytrium* genus, *Traustochytrium* genus, and *Ulkenia* genus, and the algae belonging to Labyrinthulales family are selected from algae belonging to the *Labyrinthula* genus.

In a particular preferred embodiment, the algae belonging to the *Isochrysis* genus, to the *Tisochrysis* genus, to the *Emiliania* genus, to the *Pavlova* genus, to the *Chlorella* genus, to the *Helicosporidium* genus, to the *Chlorella* genus, to the *Muriella* genus, to the *Prototheca* genus, to the *Nannochloris* genus, to the *Micractinium* genus, to the *Scenedesmus* genus, to the *Desmodesmus* genus, to the *Coelastrella* genus, to the *Neochloris* genus, to the *Bracteacoccus* genus, to the *Ankistrodesmus* genus, to the *Dunaliella* genus, to the *Haematococcus* genus, to the *Chlamydocapsa* genus, to the *Chlorococcum* genus, to the *Tetraselmis* genus, to the *Thalassiosira* genus, to the *Skeletonema* genus, to the *Nannochloropsis* genus, to the *Schizochytrium* genus, to the *Aurantochytrium* genus, to the *Aplanochytrium* genus, to the *Oblongichytrium* genus, to the *Sycyoidochytrium* genus, to the *Botryochytrium* genus, to the *Parietichytrium* genus, to the *Traustochytrium* genus, to the *Ulkenia* genus, or to the *Labyrinthula* genus, is a microalga.

Preferably, the microalga belonging to the *Isochrysis* genus is *Isochrysis galbana*, the microalga belonging to the *Chlorella* genus is *Chlorella saccharophila*, *Chlorella vulgaris*, *Chlorella sorokiniana*, *Chlorella zofingiensis* or *Chlorella* sp., the microalga belonging to the *Scenedesmus* genus is *Scenedesmus* sp, the microalga belonging to the *Desmodesmus* genus is *Desmodesmus subspicatus*, the microalga belonging to the *Haematococcus* genus is *Haematococcus pluvialis*, the microalga belonging to the *Thalassiosira* genus is *Thalassiosira pseudonana*, and the microalga belonging to the *Nannochloropsis* genus is *Nannochloropsis gaditana*.

According to the invention, both naturally-occuring algae from the phylum Haptophyta, of the phylum Chlorophyta and of the phylum Heterokontophyta, and genetically modified algae from these phyla are included, wherein genetically modified algae are those algae whose genetic material has been altered using genetic engineering techniques.

According to the first step of the method for the production of chitosan of the invention, the chitosan producing algal biomass as described above is cultured under suitable growing conditions that allow the production of chitosan.

Algal biomass growing conditions allowing the production of chitosan according to the invention relate to growing conditions including particular culture media, $CO_2$ concentration, temperature, exposition to light, pH, etc. which are known by the skilled person and can be determined experimentally for a particular chitosan producing alga, particularly microalga, biomass belonging to microalgae of the Haptophyta phylum, to microalgae of the Chlorophyta phylum, or to microalgae of the phylum Heterokontophyta according to the invention.

Practically any medium suitable for growing can be used; nevertheless, illustrative, non-limitative examples of said media include: f/2 (Guillard R R & Ryther J H 1962 Can. J. Microbiol. 8: 229-239) and derivatives including f/2×2, Erds (Tompkins J. et al. 1995 Culture Collection of Algae and Protozoa. Catalog of Strains. Ambleside, UK, 204 pp.), K/2 (Keller M D et al. 1987 J. Phycol. 23: 633-638), Kühl's medium (Kühl A 1962 Vortag Bot. Hrsg. Deut. Botan. Ges. 1: 157-166), Bold's Basal Medium (BBM) (Bischoff H W & Bold H C 1963 University of Texas Publications 6318: 1-95), and BG11 (also known as BlueGreen medium).

The $CO_2$ contained in the air as carbon source for the photosynthesis may be bubbled through the culture and, optionally, may be supplemented with pure carbon dioxide. Thus, the culture can be performed in the absence of aeration or with aeration. In a particular embodiment, the culture is carried out without aeration. In another embodiment, the culture is performed with aeration, for example, with air or with up to 5% $CO_2$ enriched air, at a rate of delivery comprised between more than 0 and 1 L/min.

If necessary, the culture can be cooled by a flow of cold water over the surface of the culture vessel or by controlling the air temperature with refrigerated air or conditioning units. In a particular, non-limiting, example the temperature ranges from about 17° C. to about 30° C.

In another particular, non-limiting, example the pH can vary between about 6 and about 9.5, preferably between about 6.6 and about 7.8.

The algal biomass according to the method of the invention may be grown under photoautotrophic, mixotrophic, or heterotrophic growth conditions. Photoautotrophic growth involves synthesis of the algal food from inorganic substances using light as energy source and the capability of using carbon dioxide as its principal source of carbon. Mixotrophic growth involves the use of different sources of energy and carbon. Heterotrophic growth involves use of organic carbon for growth. Mixotrophic and heterotrophic growth conditions are known in the art and include, without limitation, conditions described by Yanna (Yanna L et al. 2009 Biotechnol. Let. 31 (7): 1043-1049), Pérez-García (Pérez-García O et al. 2011 Water Res. 45(1): 11-36), Cheirsilp & Torpee (Cheirsilp B & Torpee T 2012 Biores. Technol. 110: 510-516).

In a particular embodiment, the algal biomass belongs to microalgae growing under photoautotrophic growth conditions. Natural light is usually sufficient to maintain cultures in the laboratory. Artificial lighting by fluorescent bulbs may also be employed for culture maintenance and experimental purposes. Light intensity should range between 0.2-50% of full daylight, with 5-10% most often employed. Light intensity and quality can be manipulated with filters. Many microalgal species do not grow well under constant illumination, and hence a light/dark (LD) cycle may be used (maximum 16:8 LD, usually 14:10 or 12:12).

The algae biomass can be cultured with or without mixing, preferably with mixing. Mixing prevents sedimentation to ensure that all cells of the population are equally exposed to the light and nutrients, to avoid thermal stratification (e.g. in outdoor cultures) and to improve gas exchange between the culture medium and the air. Depending on the scale of the culture system, mixing may be achieved by stirring by hand (test tubes, erlenmeyers), aerating (bags, tanks), or using paddle wheels and jetpumps in open ponds.

Exemplary, non-limiting, growing conditions include 1-5% $CO_2$, 15-30° C., preferably 20-25° C., 5-10 days culture, light and/or shaking. In a particular embodiment, the chitosan algal biomass is cultured until the stationary growth phase is reached, i.e. until the net growth of the culture is zero (due to nitrogen, light, nutrients, etc, limitation and involving biochemical changes in the cells) and the cell density is relatively constant. The growth rate of an algal population is a measure of the increase in biomass over time and it is determined from the exponential phase. The duration of exponential phase in cultures depends upon the size of the innoculum, the growth rate and the capacity of the medium and culturing conditions to support algal growth. Cell count and dry weight are common units of biomass determination. In vivo fluorescence and turbidity can be used as surrogate measures of algal growth which enable higher temporal resolution.

Particular, non-limiting, suitable growing conditions that allow the production of chitosan by an algal biomass belonging to algae belonging to the phylum Haptophyta, to the phylum Chlorophyta, or to the phylum Heterokontophyta are shown in Example 1.

The algae belonging to the phylum Haptophyta, to the phylum Chlorophyta or to the phylum Heterokontophyta of the algal biomass can be collected from the environment or can be cultured in a photobioreactor. In a particular embodiment, the algal biomass is cultured in a photobioreactor in a suitable medium, under a suitable luminous intensity, at a suitable temperature.

The algae can be obtained from nature or from commercially available sources including ATCC (American Type Culture Collection), UTEX (Culture Collection of Algae, University of Texas at Austin), CSIRO (Commonwealth Scientific and Industrial Research Organisation). CCAP (Culture collection of Algae and protozoa), SCCAP (Scandinavian Culture Collection for Algae and Protozoa), Plymouth Culture Collection of Marine Microalgae, RCC (Roscoff Culture Collection), SAG (The Culture Collection of Algae at Goettingen University), NCMA (National Center for Marine Algae and Microbiota), Algobank-Caen, CCALA (Culture Collection of Autotrophic Organisms), CPCC (Canadian Phycological Culture Center), CAUP (Culture collection of algae of Charles University in Prague), ACOI (Coimbra Collection of Algae), NIES (Microbial Culture Collection at National Institute for Environmental Studies).

In a second step of the method for the production of chitosan of the invention, an algal extract comprising said chitosan is recovered from the culture.

In a particular embodiment of the first method of the invention, the chitosan produced by said method is not purified from the algal biomass, so the algal extract comprising chitosan is equivalent to the chitosan producing biomass after production of said chitosan. In particular, the chitosan producing algal biomass is not disrupted (e.g. by homogenization) after chitosan production. In another particular embodiment, an algal extract comprising chitosan is recovered from the culture, wherein said recovery further comprises additional steps, particularly a step of disruption of the algal biomass and/or a step of purification of the chitosan from the algal biomass, wherein the algal biomass is disrupted before recovering the chitosan.

Biomass extraction techniques according to the invention include liquid-solid extraction, liquid-liquid extraction, partitioning, acid-base extractions, ultrasound extraction (UE), microwave assisted extraction (MAE), solid-phase extraction (SPE), supercritical fluid extraction (SFE), and pressurised solvent extraction (PSE), as described in Segneanu A E et al. 2013 Biomass Extraction Methods Chapter 15, http://dx.doi.org/10.5772/55338).

In a particular embodiment, the chitosan producing algal biomass is removed from the culture or harvested by conventional techniques including, without limitation, filtration, flocculation, flotation, centrifugation, or any combination thereof. In a particular embodiment, the chitosan producing algal biomass is removed and recovered by centrifugation. In a particular additional embodiment, the chitosan producing algal biomass may be dried after being harvested. Algal biomass drying methods include, without limitation, sun drying and advanced techniques including vacuum drying, freeze drying, drum drying, oven-drying, spray-drying and fluidized-bed drying. In particular, freeze-drying is widely used for dewatering algal biomass, since it is a gentle process in which all cell constituents are preserved without rupturing the cell wall.

Methods for biomass disruption, in particular for algal biomass cell disruption, are known in the art and include, without limitation, routinely techniques including homogenization, autoclave, bead-beating, sonication, microwave and osmotic shock, as well as the cationic surfactant-based method described by Huang & Kim (Huang W C & Kim J D 2012 Bioresour Technol 149: 579-581). In a particular embodiment, the chitosan producing algal biomass disruption is performed by homogenization. Methods for homogenization of an algal biomass are known by the skilled person and include, without limitation, high pressure homogenization (e.g. by using a pressure homogenizer). Additional homogenization methods according to the invention include exposure to high/low pH, including homogenization in the presence of 2% sodium hydroxide.

Thus, the first method of the invention allows the recovery of an algal extract comprising chitosan from the culture of a chitosan producing algal biomass. Chitosan may be present in the algal extract recovered in the first method of the invention in a very broad concentration range. In a particular embodiment, chitosan is present in the algal extract recovered in the first method of the invention at a concentration comprised between about 0.001% and about 99.998%) by weight with respect to the total weight of the algal extract, preferably between about 0.1% and about 99.998%, preferably between 0.1% and 75% by weight, more preferably between 0.1% and 45% by weight, still more preferably between 1% and 15% by weight.

In a particular embodiment, the chitosan may be further purified from the algal extract comprising chitosan obtained from the algal biomass. Thus, chitosan may be further purified from the algal extract, resulting in an algal extract of chitosan wherein said chitosan is present at a concentraction of at least 95% by weight with respect to the total weight of the microalgal extract, preferably of at least 96% by weight, more preferably of at least 98% by weigth.

Methods for the purification of chitosan from the algal extract comprising chitosan obtained from the algal biomass include, without limitation, the method described by Hirano & Nagao for the preparation of colloidal chitin by methanesulfonic acid (Hirano S & Nagao N 1988 Agric. Biol. Chem. 52(8): 2111-2112), as well as those methods disclosed in U.S. Pat. No. 2,795,579 A, and US2009/0137526A1. Additional methods include, without limitation, those described by Hayes (Hayes M et al. 2008 Biotech. J. 3(7): 871-877), by Niederhofer (Niederhofer A et al. 2004 Biopharmaceutics 57(1): 101-105), by Weiping (Weiping W et al. 2008 Carbohydrate Polymers 74(1): 127-132), by Abdou S et al. 2008 Biores. Tech. 99(5): 1359-1367), by Pochanavanich (Pochanavanich P et al. 2002 Letters Appl. Microbiol. 35(1): 17-21), and by Nitar (Nitar N et al. 2002 Biotech. Lett. 24(2): 131-134).

In a further aspect, the present invention relates to the chitosan obtained according to the method for the production of chitosan of the invention as described above.

In a particular embodiment, the chitosan obtained according to the method for the production of chitosan of the invention shows at least one of the following characteristics:

- the molecular weight of said chitosan according to the invention is between 10 and 60 kDa, more preferably between 15 and 50 kDa.
- the degree of acetylation of said chitosan according to the invention ranges from 1 to 40%, preferably between 7 and 35%.
- the degree of polymerization of said chitosan according to the invention ranges from 50 to 500, preferably between 100 and 250.
- the polydispersity index of said chitosan according to the invention is less than or equal to 2.0, preferably ranging between 1.0 and 2.0.

The chitosan obtained by the first method of the invention can be quantified or semi-quantified. Methods for chitosan quantification are known by the skilled person. In a particular embodiment, the chitosan obtained by the first method of the invention is detected, and optionally (semi)-quantified, by chitosan-binding specific proteins as described, in a way of a non-limiting example, by Nampally (Nampally M et al. 2012 Appl. Environ. Microbiol. 78(9): 3114-3119).

In a further aspect, the present invention relates to an algal extract comprising chitosan obtained by the first method of the invention as described above. In a particular embodiment, said algal extract is a microalgal extract.

In a particular embodiment, the algal extract according to the invention, particularly microalgal extract, which comprises chitosan, may also include additional components other than chitosan. Said additional components may be naturally occurring compounds in algae, such as metabolites, carotenes, chlorophylls, lipids, carbohydrates and the like or, alternatively, said additional components may be produced during the process for producing the algal extract of the invention.

Metabolites include any intermediate of product of metabolism, particularly of the algal metabolism. In a particular embodiment, this term includes those products of metabolism, particularly of the algal metabolism, with a molecular weight of less than 1500 Daltons.

Carotenes include unsaturated hydrocarbon compounds of formula $C_{40}H_x$. Carotenes include, without limitation, α-carotene, β-carotene, alloxanthin, crocoxanthin, diatoxanthin, diadinoxanthin, echinenone, fucoxanthin, loroxanthin, lutein, monadoxanthin, myxol glycosides and oscillol glycosides, neoxanthin, nostoxanthin, peridinin, prasinoxanthin, siphonaxanthin, vaucheriaxanthin, violaxanthin, and zeaxanthin.

Chlorophyls include pigments comprising a porphyrin ring, found in cyanobacteria, algae and plants, and that are involved in the photosynthesis, including without limitation chlorophyll A, chlorophyll B, and chlorophyll C.

Illustrative, non-limitative, examples of lipids which can be present in the chitin and/or chitosan comprising algal extract of the invention include fatty acids (i.e., carboxylic acids with a long aliphatic tail (chain), usually consisting of 4 to 28 carbon atoms, which is either saturated or unsaturated), including polyunsaturated fatty acids (PUFAs), i.e., fatty acids that contain more than one double bond in their backbone (although some monounsaturated omega-9 fatty acids are also considered as PUFAs). By illustrative, the microalgal extract of the invention can contain fatty acids such as, for example, caprylic acid (C8:0), capric acid (C10:0), undecanoic acid (C11:0 (IS)), lauric acid (C12:0), tridecanoic acid (C13:0), myristic acid (C14:0), myristoleic acid (C14:1 n5), pentadecanoic acid (C15:0), cis-10-pentadecenoic acid (C15:1 n5), palmitic acid (C16:0), palmitoleic acid (C16:1 n7), hexadecanoic acid (C17:0), cis-10-hexadecanoic acid (C17:1 n7), stearic acid (C18:0), elaidic acid (C18:1t n9), oleic acid (C18:1c n9), linolelaidic acid (C18:2t n6), linoleic acid [LA] (C18:2c n6), gamma-linoleic acid [GLA] (C18:3 n6), arachidic acid (C20:0), alpha-linolenic acid [ALA] (C18:3 n3), cis-11-eicosenoic acid (C20:1 n9), heneicosanoic acid (C21:0), cis-11,14-eicosadienoic acid (C20:2 n6), cis-8,11,14-eicosatrienoic acid (C20:3 n6), behenic acid (C22:0), arachidonic acid [ARA] (C20:4 n6), cis-11,14,17-eicosatrienoic acid (C20:3 n3), euricic acid (C22:1 n9), tricosanoic acid (C23:0), cis-5,8,11,14,17-eicosapentaenoic acid [EPA] (C20:5 n3), cis-13,16-docosadienoic acid (C22:2 n6), lignoceric acid (C24:0), nervonic acid (C:24:1 n9), cis-4,7,10,13,16-docosapentaenoic acid (C22:5 n6), cis-4,7,10,13,16,19-docosahexanoic acid [DHA] (C22:6 n3), etc.

Illustrative, non-limitative, examples of carbohydrates include structural carbohydrates in microalgae such as cellulose, mannan, algaenan, hemicellulose, beta-glucans, amongst others.

Besides comprising chitosan, the algal extract obtained by the first method of the invention, additional algal components can be present in said algal extract in a very broad concentration range. The amounts in which the different components that may be present in the other algal components fraction can vary broadly depending among other things on the algae, the solvent used for producing the extract, the extraction conditions, etc. Nevertheless, in a particular embodiment, chitosan is present in the algal extract obtained by the method of the invention at a concentration comprised between about 0.1% and about 99.998% by weight with respect to the total weight of the algal extract, preferably between 1% and about 99.998% by weight, preferably between 10% and 99.5% by weight, more preferably between 10% and 99% by weight, still more preferably between 30% and 98.5% by weight, even more preferably between 50% and 98% by weight. In some particular embodiments, the algal extract obtained by the first method of the invention comprises from 1% to 99.998% by weight of other algal components, for example, between 10% and 99.998% by weight, between 20% and 99.998% by weight, between 30% and 99.998% by weight, between 40% and 99.998% by weight, between 45% and 99.998% by weight, between 50% and 99.998% by weight, between 55% and 99.998% by weight, between 60% and 99.998% by weight, between 70% and 99.998% by weight, between 80% and 99.998% by weight, between 90% and 99.998% by weight. In some specific embodiments, the algal extract obtained by the first method of the invention comprises between 80% and 98.5% by weight, between 89.7% and 96.9% by weight, or between 79.9% and 94.94% by weight, of the other algal components.

3. Method for the Production of Chitin of the Invention

The authors of the present invention have found that algae belonging to the phylum Chlorophyta are useful in the production of chitin. Particularly, the chlorophytes *Chlorococcum* sp., *Scenedesmus* sp., *Chlorella vulgaris* (CS41), *Haematococcus pluvialis*, *Bracteacoccus* sp., *Chlorella* sp., *Chlorella saccharophila* and *Desmodesmus subspicatus* produce chitin in significant amounts (see Examples 1 and 2). Furthermore, the chitin obtained according to the method shows a low polydispersity, i.e. is highly homogenous, rendering said chitin suitable for therapeutic applications.

Therefore, in another aspect, the present invention relates to a method for the production of chitin (method of the invention for the production of chitin, or second method of the invention) that comprises:

culturing a chitin producing algal biomass under suitable growing conditions for the production of chitin,
   disrupting the algal biomass, and
   recovering an algal extract comprising said chitin from the culture,
   wherein the algal biomass comprises algae belonging to the phylum Chlorophyta, and wherein the chitin producing algal biomass is disrupted before recovering said algal extract comprising chitin.

Thus, in a first step of the second method of the invention, said method comprises culturing chitin producing algal biomass under suitable growing conditions that allow the production of chitin.

According to the invention, the chitin producing algal biomass, particularly microalgal biomass, includes not only the biological material which constitutes the alga organism, but also the biological material or organic matter generated in a biological process, spontaneous or not, associated to said alga organism. The chitin producing algal biomass according to the invention includes an algal biomass comprising chitin producing algae, more particularly microalgae. Methods to determine whether an organism, particularly an alga, more particularly a microalga, is a chitin producing microalga are known by the skilled person and include, without limitation, chitin specific detection by chitin-binding specific proteins, as described, in a way of a non-limiting example, by Nampally (Nampally M et al. 2012 Appl. Environ. Microbiol. 78(9): 3114-3119; see Example 1 in this application). Additional exemplary, non-limiting assays, include the assay to identify chitin based on chitin-binding protein Chbp fused to a His-tag and to a Strep-tag by Herasimenka (Herasimenka Y et al. 2010 Int. J. Mol. Sci. 11: 3122-3137), the classical test of van Wiselingh based on the purple color developed when chitosan is treated with iodine in acid medium, the test by Benjaminson based on conjugation of chitinase with fluorescent compounds to localize chitin by ultraviolet light microscopy (Benjaminson 1969 Stain Tech, 44: 27), chitin detection by use of fluorescein-conjugated wheat germ lectin (Galun M et al. 1976 Arch Microbiol 108: 9) or by use of wheat germ lectin labeled with colloidal gold (Horisberger M & Vonlanthen 1978 Arch. Microbiol. 119: 107).

The chitin producing algal biomass according to the invention includes an algal biomass comprising chitin producing algae, in particular, an algal biomass that belongs to algae belonging to the phylum Chlorophyta.

Algae belonging to the phylum Chlorophyta have been described and listed above in the context of the method for the production of chitosan of the invention and incorporated herein.

In particular, the algae belonging to the phylum Chlorophyta are selected from algae belonging to the Trebouxiophyceae class, to the Chlorophyeeae class, or to the Chlorodendrophyceae class.

More in particular, the algae belonging to the Trebouxiophyceae class are selected from algae belonging to the Chlorellales order, the algae belonging to the Chlorophyeeae class are selected from algae belonging to the Sphaeropleales order or to the Chlamydomonadales order, the algae belonging to the Chlorodendrophyceae class are selected from algae belonging to the Chlorodendrales order.

More in particular, the algae belonging to the Chlorellales order are selected from algae belonging to the Chlorellaceae family, algaealgae, the algae belonging to the Sphaeropleales order are selected from algae belonging to the Scenedesmaceae family, to the Neochloridaeeae family, to the Bracteacoccaceae family, or to the Selenastraceae family, the algae belonging to the Chlamydomonadales order are selected from algae belonging to the Dunaliellaeeae family, to the Haematocoecaeeae family, to the Palmellopsidaeeae family, or to the Chlorococcaceae family, the algae belonging to the Chlorodendrales order are selected from algae belonging to the Chlorodendraceae family.

Even more in particular, the algae belonging to Chlorellaceae family are selected from algae belonging to the *Chlorella* genus, to the *Helicosporidium* genus, to the *Chlorella* genus, to the *Muriella* genus, to the *Prototheca* genus, to the *Nannochloris* genus, or to the *Micractinium* genus, the algae belonging to Scenedesmaceae family are selected from algae belonging to the *Scenedesmus* genus, to the *Desmodesmus* genus, or to the *Coelastrella* genus, the algae belonging to the Neochloridaceae family are selected from algae belonging to the *Neochloris* genus, the algae belonging to the Bracteacoccaceae family are selected from algae belonging to the *Bracteacoccus* genus, the algae belonging to the Selenastraceae family are selected from algae belonging to the *Ankistrodesmus* genus, the algae belonging to Dunaliellaeeae family are selected from algae belonging to the *Dunaliella* genus, the algae belonging to Haematococcaceae family are selected from algae belonging to the *Haematococcus* genus, the algae belonging to the Palmellopsidaeeae family are selected from algae belonging to the *Chlamydocapsa* genus, the algae belonging to Chlorococcaceae family are selected from algae belonging to the *Chlorococcum* genus, the algae belonging to Chlorodendraceae family are selected from algae belonging to the *Tetraselmis* genus.

In a particular preferred embodiment, the algae belonging to the *Chlorella* genus, to the *Muriella* genus, to the *Prototheca* genus, to the *Nannochloris* genus, to the *Micractinium* genus, to the *Scenedesmus* genus, to the *Desmodesmus* genus, to the *Coelastrella* genus, to the *Neochloris* genus, to the *Bracteacoccus* genus, to the *Ankistrodesmus* genus, to the *Dunaliella* genus, to the *Haematococcus* genus, to the *Chlamydocapsa* genus, to the *Chlorococcum* genus, or to the *Tetraselmis* genus, is a microalga.

Preferably, the microalga belonging to the *Chlorella* genus is *Chlorella saccharophila*, *Chlorella vulgaris* (CS41), *Chlorella sorokiniana* or *Chlorella* sp., the microalga belonging to the *Haematococcus* genus is *Haematococcus pluvialis*, the microalga belonging to the *Thalassiosira* genus is *Thalassiosira pseudonana*, the microalga belonging to *Scenedesmus* genus is *Scenedesmus* sp. or *Scenedesmus subspikatus*.

According to the invention, both naturally-occuring algae from the phylum Chlorophyta, and genetically modified algae from said phylum are included, wherein genetically modified algae are those algae whose genetic material has been altered using genetic engineering techniques.

According to the first step of the method for the production of chitin of the invention, the chitin producing algal biomass as described above is cultured under suitable growing conditions that allow the production of chitin.

Algal biomass growing conditions allowing the production of chitin according to the invention relate to growing conditions including particular culture media, $CO_2$ concentration, temperature, exposition to light, pH, etc. which are known by the skilled person and can be determined experimentally for a particular chitin producing alga, particularly microalga, biomass belonging to microalgae of the Chlorophyta phylum according to the invention.

Suitable media for growing algae have been described above in the context of the method for the production of chitosan of the invention and incorporated herein. Photoautotrophic, mixotrophic, or heterotrophic algal biomass growth conditions have been described above as well. Further growing conditions concerning mixing, $CO_2$, temperature, and light have been described above in the context of the first method of the invention and incorporated herein. In a particular embodiment, the chitin algal biomass is cultured until the stationary growth phase is reached. Particular, non-limiting, suitable growing conditions that allow the production of chitin by an algal biomass belonging to algae belonging to the phylum Chlorophyta are shown in Example 1.

The algae belonging to the phylum Chlorophyta of the algal biomass can be collected from the environment or can be cultured in a photobioreactor. The algae can be obtained from nature or from commercially available sources as previously described.

In a second step of the method for the production of chitin of the invention, the algal biomass is disrupted, more in particular, the chitin producing algal biomass is disrupted before the step of recovering said algal extract comprising chitin. Methods for biomass disruption, in particular for algal biomass cell disruption, have been described in the context of the first method of the invention for the production of chitosan and incorporated herein.

In a third step of the method for the production of chitin of the invention, the algal extract comprising the chitin is recovered from the culture.

According to the invention, an algal extract comprising chitin is recovered from the culture, wherein said recovery further comprises additional steps, particularly a step of disruption of the algal biomass and a step of purification of the chitin from the algal biomass. Biomass extraction techniques and algal biomass harvesting methods according to the invention have been described above in the context of the first method of the invention.

Thus, the second method of the invention allows the recovery of an algal extract comprising chitin from the culture of a chitin producing algal biomass. Chitin may be present in the algal extract recovered in the method of the invention in a very broad concentration range. In a particular embodiment, chitin is present in the algal extract recovered in the second method of the invention at a concentration comprised between about 0.001% and about 99.998% by weight with respect to the total weight of the algal extract, preferably between about 0.1% and about 99.998%, preferably between 0.1% and 75% by weight, more preferably between 0.1% and 45% by weight, still more preferably between 1% and 15% by weight.

In a particular embodiment, the chitin may be further purified from the algal extract comprising chitin obtained from the algal biomass. Thus, chitin may be further purified from the algal extract, resulting in a algal extract of chitin wherein said chitin is present at a concentraction of at least 95% by weight with respect to the total weight of the microalgal extract, preferably of at least 96% by weight, more preferably of at least 98% by weight. Methods for chitin purification have been described above in the context of the first method of the invention.

In a particular embodiment, the chitin obtained according to the method for the production of chitin of the invention shows at least one of the following characteristics:
the degree of polymerization of said chitin according to the invention ranges from 50 to 500, preferably between 100 and 250.
the polydispersity index of said chitin according to the invention is less than or equal to 2.0, preferably ranging between 1.0 and 2.0.

In a further aspect, the present invention relates to the chitin obtained according to the second method of the invention as described above. The chitin obtained by the second method of the invention can be quantified or semiquantified by methods described above.

In a further aspect, the present invention relates to an algal extract comprising chitin obtained by the second method of the invention as described above. In a particular embodiment, said algal extract is a microalgal extract.

In a particular embodiment, the algal extract according to the invention, particularly microalgal extract, which comprises chitin, may also include additional components other than chitin. Said additional components may be naturally occurring compounds in algae, such as metabolites, carotenes, chlorophylls, lipids, carbohydrates and the like or, alternatively, said additional components may be produced during the process for producing the algal extract of the invention. Said additional components have been described above in the context of the first method of the invention.

4. Method for the Production of Chitin and Chitosan of the Invention

The inventors have found that algae belonging to the phylum Chlorophyta are useful in the production of chitin and chitosan. Particularly, chlorophytes of the genus *Chlorococcum, Scenedesmus, Desmodesmuss, Chlorella, Haematococcus* and *Bracteacoccus* produce chitin and chitosan in significant amounts Thus, in a further aspect, the invention relates to a method for the production of a composition comprising chitin and chitosan (third method of the invention, or method for the production of chitin and chitosan of the invention) that comprises:
culturing a chitin and chitosan producing algal biomass under suitable growing conditions for the production of chitin and chitosan,
disrupting the algal biomass, and
recovering an algal extract comprising said chitin and chitosan from the culture, and
wherein the algal biomass comprises algae belonging to the phylum Chlorophyta, and
wherein the chitin and chitosan producing algal biomass is disrupted before recovering said algal extract comprising chitin and chitosan.

Thus, in a first step of the third method of the invention, said method comprises culturing a chitin and chitosan producing algal biomass under suitable growing conditions that allow the production of chitin and chitosan.

According to the invention, the chitin and chitosan producing algal biomass, particularly microalgal biomass, includes not only the biological material which constitutes the alga organism, but also the biological material or organic matter generated in a biological process, spontaneous or not, associated to said alga organism. The chitin and chitosan producing algal biomass according to the invention includes an algal biomass comprising chitin and chitosan producing algae, more particularly microalgae. Methods to determine whether an organism, particularly an alga, more particularly a microalga, is a chitin and chitosan producing microalga are known by the skilled person and include, without limitation, chitin and chitosan specific detection as previously described in the context of the first and second methods of the invention.

The chitin and chitosan producing algal biomass according to the invention includes an algal biomass comprising chitin and chitosan producing algae, in particular, an algal biomass that belongs to algae belonging to the phylum Chlorophyta.

Algae belonging to the phylum Chlorophyta have been described and listed above in the context of the first method of the invention for the production of chitosan and incorporated herein.

In particular, the algae belonging to the phylum Chlorophyta are selected from algae belonging to the Trebouxiophyceae class, to the Chlorophyceae class, or to the Chlorodendrophyceae class.

More in particular, the algae belonging to the Trebouxiophyceae class are selected from algae belonging to the Chlorellales order, the algae belonging to the Chlorophyceae class are selected from algae belonging to the Sphaeropleales order or to the Chlamydomonadales order, the algae belonging to the Chlorodendrophyceae class are selected from algae belonging to the Chlorodendrales order.

More in particular, the algae belonging to the Chlorellales order are selected from algae belonging to the Chlorellaceae family, the algae belonging to the Sphaeropleales order are selected from algae belonging to the Scenedesmaceae family, to the Neochloridaceae family, to the Bracteacoccaceae family, or to the Selenastraeeae family, the algae belonging to the Chlamydomonadales order are selected from algae belonging to the Dunaliellaceae family, to the Haematococcaceae family, to the Palmellopsidaceae family, or to the Chlorococcaceae family, the algae belonging to the Chlorodendrales order are selected from algae belonging to the Chlorodendraceae family.

Even more in particular, the algae belonging to Chlorellaceae family are selected from algae belonging to the *Chlorella* genus, to the *Helicosporidium* genus, to the *Chlorella* genus, to the *Muriella* genus, to the *Prototheca* genus, to the *Nannochloris* genus, or to the *Micractinium* genus, the algae belonging to Scenedesmaceae family are selected from algae belonging to the *Scenedesmus* genus, to the *Desmodesmus* genus, or to the *Coelastrella* genus, the algae belonging to the Neochloridaceae family are selected from algae belonging to the *Neochloris* genus, the algae belonging to the Bracteacoccaceae family are selected from algae belonging to the *Bracteacoccus* genus, the algae belonging to the Selenastraeeae family are selected from algae belonging to the *Ankistrodesmus* genus, the algae belonging to Dunaliellaceae family are selected from algae belonging to the *Dunaliella* genus, the algae belonging to Haematococcaceae family are selected from algae belonging to the *Haematococcus* genus, the algae belonging to the Palmellopsidaceae family are selected from algae belonging to the *Chlamydocapsa* genus, the algae belonging to Chlorococcaceae family are selected from algae belonging to the *Chlorococcum* genus, the algae belonging to Chlorodendraceae family are selected from algae belonging to the *Tetraselmis* genus.

In a particular preferred embodiment, the algae belonging to the *Chlorella* genus, to the *Muriella* genus, to the *Prototheca* genus, to the *Nannochloris* genus, to the *Micractinium* genus, to the *Scenedesmus* genus, to the *Desmodesmus* genus, to the *Coelastrella* genus, to the *Neochloris* genus, to the *Bracteacoccus* genus, to the *Ankistrodesmus* genus, to the *Dunaliella* genus, to the *Haematococcus* genus, to the *Chlamydocapsa* genus, to the *Chlorococcum* genus, or to the *Tetraselmis* genus, is a microalga.

Preferably, the microalga belonging to the *Chlorella* genus is *Chlorella saccharophila* or *Chlorella vulgaris* (CS41), the microalga belonging to the *Haematococcus* genus is *Haematococcus pluvialis*, and the microalga belonging to the *Thalassiosira* genus is *Thalassiosira pseudonana*.

According to the invention, both naturally-occuring algae from the phylum Chlorophyta, and genetically modified algae from said phylum are included, wherein genetically modified algae are those algae whose genetic material has been altered using genetic engineering techniques.

According to the first step of the method for the production of chitin and chitosan of the invention, the chitin and chitosan producing algal biomass as described above is cultured under suitable growing conditions that allow the production of chitin and chitosan.

Algal biomass growing conditions allowing the production of chitin and chitosan according to the invention relate to growing conditions including particular culture media, $CO_2$ concentration, temperature, exposition to light, pH, etc. which are known by the skilled person and can be determined experimentally for a particular chitin and chitosan producing alga, particularly microalga, biomass belonging to microalgae of the Chlorophyta phylum according to the invention.

Suitable media for growing algae have been described above in the context of the first method of the invention for the production of chitosan and incorporated herein. Photoautotrophic, mixotrophic, or heterotrophic algal biomass growth conditions have been described above as well. Further growing conditions concerning mixing, $CO_2$, temperature, and light have been described above in the context of the first method of the invention and incorporated herein. In a particular embodiment, the chitin and chitosan algal biomass is cultured until the stationary growth phase is reached. Particular, non-limiting, suitable growing conditions that allow the production of chitin and chitosan by an algal biomass belonging to algae belonging to the phylum Chlorophyta are shown in Example 1.

The algae belonging to the phylum Chlorophyta of the algal biomass can be collected from the environment or can be cultured in a photobioreactor. The algae can be obtained from nature or from commercially available sources as previously described.

In a second step of the method for the production of chitin and chitosan of the invention, the algal biomass is disrupted, more in particular, the chitin and chitosan producing algal biomass is disrupted before the step of recovering said algal extract comprising chitin and chitosan. Methods for biomass disruption, in particular for algal biomass cell disruption, have been described in the context of the first method of the invention for the production of chitosan and incorporated herein.

In a third step of the third method of the invention, the algal extract comprising the chitin and chitosan is recovered from the culture.

In a particular embodiment, the chitin and chitosan produced by the third method of the invention is not purified from the algal biomass, so the algal extract comprising chitin and chitosan is equivalent to the chitin and chitosan producing biomass after production of said chitin and chitosan. In a particular preferred embodiment, an algal extract comprising chitin and chitosan is recovered from the culture, wherein said recovery further comprises additional steps, particularly a step of disruption of the algal biomass and a step of purification of the chitin and chitosan from the algal biomass. Biomass extraction techniques and algal biomass harvesting methods according to the invention have been described above in the context of the first method of the invention.

Thus, the third method of the invention allows the recovery of an algal extract comprising chitin and chitosan from the culture of a chitin and chitosan producing algal biomass. Chitin and chitosan may be present in the algal extract recovered in the method of the invention in a very broad concentration range. In a particular embodiment, chitin and chitosan are present in the algal extract recovered in the second method of the invention at a concentration comprised between about 0.001% and about 99.998%) by weight with respect to the total weight of the algal extract, preferably between about 0.1% and about 99.998%, preferably between 0.1% and 75% by weight, more preferably between 0.1% and 45% by weight, still more preferably between 1% and 15% by weight.

In a particular embodiment, the chitin and chitosan may be further purified from the algal extract comprising chitin and chitosan obtained from the algal biomass. Thus, chitin and chitosan may be further purified from the algal extract, resulting in a algal extract of chitin and chitosan wherein said chitin and chitosan are present at a concentraction of at least 95% by weight with respect to the total weight of the microalgal extract, preferably of at least 96% by weight, more preferably of at least 98%) by weigth. Methods for chitin purification have been described above in the context of the first method of the invention.

In a further aspect, the present invention relates to a composition comprising the chitin and chitosan obtained according to the method for the production of chitin of the invention as described above. The chitin and chitosan obtained by the third method of the invention can be quantified or semi-quantified by methods described above.

In a further aspect, the present invention relates to an algal extract comprising chitin and chitosan obtained by the third method of the invention as described above. In a particular embodiment, said algal extract is a microalgal extract.

In a particular embodiment, the algal extract according to the invention, particularly microalgal extract, which comprises chitin and chitosan, may also include additional components other than chitin and chitosan. Said additional components may be naturally occurring compounds in algae, such as metabolites, carotenes, chlorophylls, lipids, carbohydrates, and the like or, alternatively, said additional components may be produced during the process for producing the algal extract of the invention. Said additional components have been described above in the context of the first method of the invention.

In a particular embodiment, the chitosan in the composition obtained according to the method for the production of a composition comprising chitin and chitosan of the invention shows at least one of the following characteristics:
- the molecular weight of said chitosan according to the invention is between 10 and 60 kDa, more preferably between 15 and 50 kDa.
- the degree of acetylation of said chitosan according to the invention ranges from 1 to 40%, preferably between 7 and 35%.
- the degree of polymerization of said chitosan according to the invention ranges from 50 to 500, preferably between 100 and 250.
- the polydispersity index of said chitosan according to the invention is less than or equal to 2.0, preferably ranging between 1.0 and 2.0.

In a particular embodiment, the chitin in the composition obtained according to the method for the production of a composition comprising chitin and chitosan of the invention shows at least one of the following characteristics:
- the degree of polymerization of said chitin according to the invention ranges from 50 to 500, preferably between 100 and 250.
- the polydispersity index of said chitin according to the invention is less than or equal to 2.0, preferably ranging between 1.0 and 2.0.

5. Products of the Invention

In a further aspect, the present invention relates to a chitosan characterized by a molecular weight of 10-60 kDa, a degree of acetilation of 1-40%, a degree of polymerization of 50-500 and/or a polidispersity index of less than or equal to 2.0. Methods to determine the degree of acetylation, the degree of polymerization and the polydispersity index have been mentioned above and incorporated herein.

In a particular embodiment, the chitosan of the invention shows at least one of the following characteristics:
- the molecular weight of said chitosan according to the invention is between 10 and 60 kDa, more preferably between 15 and 50 kDa.
- the degree of acetylation of said chitosan according to the invention ranges from 1 to 40%, preferably between 7 and 35%.
- the degree of polymerization of said chitosan according to the invention ranges from 50 to 500, preferably between 100 and 250.
- the polydispersity index of said chitosan according to the invention is less than or equal to 2.0, preferably ranging between 1.0 and 2.0.

In a further aspect, the present invention relates to a chitin characterized by a polydispersity index of less than or equal to 2.0 and/or a degree of polymerization ranging between 50 and 500.

In a particular embodiment, the chitin of the invention shows at least one of the following characteristics:
- the degree of polymerization of said chitin according to the invention ranges from 50 to 500, preferably between 100 and 250.
- the polydispersity index of said chitin according to the invention is less than or equal to 2.0, preferably ranging between 1.0 and 2.0.

In a further aspect, the invention relates to a composition comprising chitin and chitosan, wherein said chitosan is characterized by a molecular weight of 10-60 kDa, a degree of acetilation of 1-40%, a degree of polymerization of 50-500 and/or a polidispersity index of less than or equal to 2.0. In a particular embodiment, the chitin of the composition of the invention is characterized by a polydispersity index of less than or equal to 2.0 and/or a degree of polymerization ranging between 50 and 500. Thus, the invention relates to a composition comprising chitin and chitosan, wherein said chitosan is characterized by a molecular weight of 10-60 kDa, a degree of acetilation of 1-40%, a degree of polymerization of 50-500 and/or a polidispersity index of less than or equal to 2.0, and/or wherein said chitin is characterized by degree of polymerization ranging between 50 and 500 and a polidispersity index of less than or equal to 2.0.

In a particular embodiment, the chitosan of the composition comprising chitin and chitosan of the invention shows at least one of the following characteristics:
- the molecular weight of said chitosan according to the invention is between 10 and 60 kDa, more preferably between 15 and 50 kDa.
- the degree of acetylation of said chitosan according to the invention ranges from 1 to 40%, preferably between 7 and 35%.

the degree of polymerization of said chitosan according to the invention ranges from 50 to 500, preferably between 100 and 250.

the polydispersity index of said chitosan according to the invention is less than or equal to 2.0, preferably ranging between 1.0 and 2.0.

In a particular embodiment, the chitin of the composition comprising chitin and chitosan of the invention shows at least one of the following characteristics:

the degree of polymerization of said chitin according to the invention ranges from 50 to 500, preferably between 100 and 250.

the polydispersity index of said chitin according to the invention is less than or equal to 2.0, preferably ranging between 1.0 and 2.0.

6. Compositions of the Invention

The person skilled in the art will understand that the chitosan, the chitin, or the combination of chitin and chitosan obtained, respectively, by the first, second or third method of the invention, as well as the algal extract comprising said chitosan, chitin or combination thereof obtained by the methods of the invention, preferably a microalgal extract comprising said chitosan, chitin, or combination thereof by the methods of the invention, can be part of a food or feed, or of a agricultural, cosmeceutical, cosmetic, nutraceutical, or pharmaceutical product, which constitutes an additional aspect of the present invention. Said products can be in a liquid, semi-solid or solid form.

Thus, in a further aspect, the present invention relates to a food, feed, agricultural, cosmeceutical, cosmetic, nutraceutical or pharmaceutical composition comprising the chitosan, the chitin or the combination of chitin and chitosan obtained, respectively, by the first, second and third methods of the invention, or comprising a algal extract comprising chitosan, chitin, or the combination of chitin and chitosan obtained by the methods of the invention, wherein said composition comprises between about 0.1% and about 99.998% by weight of said chitin and/or chitosan, or of said algal extract.

Thus, the food, feed, agricultural, cosmeceutical, cosmetic, nutraceutical or pharmaceutical composition comprising chitosan and/or chitin obtained by the methods of the invention or comprising an algal extract comprising said chitosan and/or chitin, comprises said chitosan and/or chitin, or algal extract, at a concentration comprised between about 0.1% and about 99.998% by weight with respect to the total weight of the composition, preferably between 1% and 99.5% by weight, more preferably between 10% and 99% by weight, still more preferably between 30% and 98.5% by weight, even more preferably between 50% and 98% by weight.

In a particular embodiment, the chitosan and/or the chitin obtained by the methods of the invention or the algal extract comprising said chitosan and/or chitin obtained by the methods of the invention are part of a food or feed. As used herein, the term "food" is any substance or product of any nature, solid or liquid, natural or processed which due to its characteristics, applications, components, preparation and state of preservation, can usually or ideally be used for some of the following purposes: a) as normal nutrition for human beings or animals or as pleasurable foods; or b) as dietetic products, in special cases of human or animal food. The term "feed" includes all the natural materials and finished products of any origin which, separately or conveniently mixed with one another, are suitable as animal food. A ready-to-eat food is that which does not need to be diluted by means of an aqueous solution suitable for consumption for example.

In principle, the ingredients present in a ready-to-eat food are balanced and there is no need to add additional ingredients to the food to make it ready to eat, such considered by a person skilled in the art. A concentrated food is that in which one or more ingredients are present at a higher concentration than in a ready-to-eat food, therefore for use it is necessary to dilute it by means of an aqueous solution suitable for consumption for example. Non-limiting, illustrative examples of foods provided by this invention include both dairy products and derivatives, for example, fermented milks, yoghurt, kephir, curd, cheeses, butters, ice creams, milk-based desserts, etc., and non-dairy products, such as baked products, cakes and pastries, cereals, chocolates, jams, juices, other fruit derivatives, oils and margarines, prepared dishes, etc.

In a particular embodiment, the food comprises between 0.1% and 5% by weight of the the chitosan and/or the chitin obtained by the methods of the invention or the algal extract comprising said chitosan and/or chitin obtained by the methods of the invention.

In a particular embodiment, the composition of the invention is an agricultural composition comprising chitosan and/or chitin obtained by the methods of the invention, or an algal extract comprising said chitosan and/or chitin obtained by the methods of the invention. The term "agricultural composition", as used herein, relates to a composition suitable for use in the cultivation of animals, plants, fungi and other life forms for food, fiber, biofuel, medicinal and other products used to sustain and enhance human life.

In a particular embodiment, the composition of the invention is a cosmeceutical composition comprising chitosan and/or chitin obtained by the methods of the invention, or an algal extract comprising said chitosan and/or chitin obtained by the methods of the invention. The term "cosmeceutical composition", as used herein, relates to a composition suitable for use in the body or animal body comprising one or more cosmeceutical products (functional cosmetics, dermoceuticals or active cosmetics), i.e., topical hybrid products with cosmetical-pharmaceutical characteristics containing active ingredients having effect on user's skin, hair and/or nails, at higher and more effective concentrations, therefore they are located in an intermediate level between cosmetic and drug. Illustrative examples of cosmeceutical products according to the invention include, in addition to chitin and/or chitosan, essential oils, ceramides, enzymes, minerals, peptides, vitamins, etc.

In a particular embodiment, the cosmeceutical composition comprises between 0.1% and 5% by weight of the chitosan and/or the chitin obtained by the methods of the invention or the algal extract comprising said chitosan and/or chitin obtained by said methods of the invention.

In a particular embodiment, the composition of the invention is a cosmetic composition comprising chitosan and/or chitin obtained by the methods of the invention, or an algal extract comprising said chitosan and/or chitin obtained by the methods of the invention. The term "cosmetic composition", as used herein, relates to a composition suitable for use in personal hygiene of human beings or animals, or in order to enhance the natural beauty or change the body appearance without affecting the structure or functions of the human or animal body, comprising one or more products providing such effects. If desired, the cosmetic composition may contain, in addition to chitin and/or chitosan, one or more cosmetic products, i.e., substances or mixtures intended to be placed in contact with the external parts of the human or animal body (epidermis, hair system, nails, lips and external genital organs) or with the teeth and the buccal mucosa, for the exclusive or main purpose of cleaning them, perfuming them, changing their appearance, protecting them, keeping them in good condition or correcting body odors. Illustrative examples of cosmetic products include the products contained in the INCI (International Nomenclature of Cosmetic Ingredients) list.

In a particular embodiment, the cosmetic composition comprises between 0.1% and 5% by weight of the chitosan and/or the chitin obtained by the methods of the invention or the algal extract comprising said chitosan and/or chitin obtained by the methods of the invention.

In a particular embodiment, the composition of the invention is a nutracetical composition comprising chitosan and/or chitin obtained by the methods of the invention, or a algal extract comprising said chitosan and/or chitin obtained by the method of the invention. The term "nutracetical composition", as used herein, relates to a composition suitable for use in human beings or animals, comprising one or more natural products with therapeutic action which provide a health benefit or have been associated with disease prevention or reduction, and it includes dietary supplements presented in a non-food matrix (e.g., capsules, powder, etc.) of a concentrated natural bioactive product usually present (or not) in the foods and which, when taken in a dose higher than that existing in those foods, exerts a favorable effect on health which is greater than the effect which the normal food may have. Therefore, the term "nutraceutical composition" includes isolated or purified food products as well as additives or food supplements which are generally presented in dosage forms normally used orally, for example, capsules, tablets, sachets, drinkable phials, etc.; such products provide a physiological benefit or protection against diseases, generally against chronic diseases. If desired, a nutraceutical composition may contain, in addition to chitin and/or chitosan, one or more nutraceuticals (products or substances associated with disease prevention or reduction), for example, flavonoids, omega-3 fatty acids, etc., and/or one or more prebiotics (non-digestible food ingredients which stimulate probiotic activity and/or growth), for example, oligofructose, pectin, inulin, galacto-oligosaccharides, lactulose, human milk oligosaccharides, dietary fiber, etc.

In a particular embodiment, the nutraceutical composition comprises between 0.1% and 5% by weight of the chitosan and/or the chitin obtained by the methods of the invention or the algal extract comprising said chitosan and/or chitin obtained by the method of the invention.

In a particular embodiment, the composition of the invention is a pharmaceutical composition comprising chitosan and/or chitin obtained by the methods of the invention, or a algal extract comprising said chitosan and/or chitin obtained by the methods of the invention. The term "pharmaceutical composition", as used herein, relates to a composition comprising a therapeutically effective amount of the chitin and/or chitosan obtained by the method of the invention or of the algal extract comprising the chitosan and/or chitin obtained by the methods of the invention and at least one pharmaceutically acceptable excipient or carrier. The term "therapeutically effective amount" as used herein in relation to chitosan and/or chitin obtained by the method of the invention or to the algal extract comprising the chitosan and/or chitin obtained by the method of the invention comprised by the pharmaceutical composition of the invention, relates to the sufficient amount of chitin, chitosan or algal extract thereof to provide the desired effect, i.e. to achieve an appreciable prevention, cure, delay, reduction of severity or amelioration of one or more symptoms derived from a disease, and will generally be determined by, among other causes, the characteristics of the agent itself and the therapeutic effect to be achieved. It will also depend on the subject to be treated, the severity of the disease suffered by said subject, the chosen dosage form, etc. For this reason, the doses mentioned in this invention must be considered only as guides for the person skilled in the art, who must adjust the doses depending on the aforementioned variables. In an embodiment, the effective amount produces the amelioration of one or more symptoms of the disease that is being treated. The terms "pharmaceutically acceptable excipient", or "pharmaceutically acceptable carrier", refer to a non-toxic solid, semisolid or liquid filler, diluent, encapsulating material or formulation auxiliary of any conventional type. A pharmaceutically acceptable carrier is essentially non-toxic to recipients at the dosages and concentrations employed, and are compatible with other ingredients of the formulation. Suitable carriers include, but are not limited to water, dextrose, glycerol, saline, ethanol, and combinations thereof. The carrier can contain additional agents such as wetting or emulsifying agents, pH buffering agents, or adjuvants, which enhance the effectiveness of the formulation. Adjuvants could be selected from the group consisting of sterile liquids, such as water and oils, including those of petroleum, animal, vegetable, or synthetic origin, such as peanut oil, soybean oil, mineral oil, sesame oil, and similars. Water or saline aqueous solutions and aqueous dextrose and glycerol solutions, particularly for injectable solutions, are preferably used as vehicles. Suitable pharmaceutical vehicles are described in "Remington's Pharmaceutical Sciences" by E. W. Martin, $22^{th}$ Edition, 2012.

The combination of compounds of the pharmaceutical compositions of the invention may be found as a prodrug, salt, solvate or clatrate, whether in an isolated dosage form or in combination with additional active agents.

The pharmaceutical compositions comprising chitosan and/or chitin obtained by the methods of the invention, or a algal extract comprising said chitosan and/or chitin obtained by the method of the invention can occur at any pharmaceutical form of administration considered appropriate for the selected administration route, for example, by systemic, oral, parenteral or topical administration, for which it will include the pharmaceutically acceptable excipients necessary for formulation of the desired method of administration. Thus, one or more suitable unit dosage forms of the pharmaceutical composition can be administered by a variety of routes including parenteral, intravenous and intramuscular routes included, as well as by direct injection into a particular tissue.

The effective quantity of the pharmaceutical composition can vary within a wide range and, in general, will vary depending on the particular circumstances of application, duration of the exposure and other considerations. The amount administered will vary depending on various factors including, but not limited to, the composition chosen, the particular disease, the weight, the physical condition, and the age of the subject. Such factors can be readily determined by the clinician employing animal models or other test systems, which are well known in the art.

When the pharmaceutical composition of the invention is prepared for administration, in certain embodiments they are combined with a pharmaceutically acceptable carrier, diluent or excipient to form a pharmaceutical formulation, or unit dosage form. The total active ingredient (i.e., chitin and/or chitosan obtained by the method of the invention, or a algal extract comprising said chitin and/or chitosan obtained by the method of the invention) in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing chitosan and/or chitin obtained by the methods of the invention, or an algal extract comprising said chitosan and/or chitin obtained by the method of the invention, can be prepared by procedures known in the art using well known and readily available ingredients.

Solid dosage forms for oral administration may include conventional capsules, sustained release capsules, conventional tablets, sustained-release tablets, chewable tablets, sublingual tablets, effervescent tablets, pills, suspensions, powders, granules and gels. At these solid dosage forms, the active compounds can be mixed with at least one inert excipient such as sucrose, lactose or starch. Such dosage forms can also comprise, as in normal practice, additional substances other than inert diluents, e.g. lubricating agents such as magnesium stearate. In the case of capsules, tablets, effervescent tablets and pills, the dosage forms may also comprise buffering agents. Tablets and pills can be prepared with enteric coatings.

Liquid dosage forms for oral administration may include emulsions, solutions, suspensions, syrups and elixirs pharmaceutically acceptable containing inert diluents commonly used in the technique, such as water. Those compositions may also comprise adjuvants such as wetting agents, emulsifying and suspending agents, and sweetening agents, flavoring and perfuming agents.

The pharmaceutical composition comprising chitosan and/or chitin obtained by the methods of the invention, or a algal extract comprising said chitosan and/or chitin obtained by the method of the invention, may be formulated for parenteral administration (e.g., by injection, for example, bolus injection or continuous infusion) and may be presented in unit dose form in ampules, pre-filled syringes, small volume infusion containers or in multi-dose containers with an added preservative. The probe may take such forms as suspensions, solutions, or emulsions in oily or aqueous vehicles, and may contain formulatory agents such as suspending, stabilizing and/or dispersing agents. Alternatively, the chitosan and/or chitin, or the algal extract thereof, may be in powder form, obtained by aseptic isolation of sterile solid or by lyophilization from solution, for constitution with a suitable vehicle, e.g., sterile, pyrogen-free water, before use. Injectable preparations, for example, aqueous or oleaginous suspensions, sterile injectable may be formulated according with the technique known using suitable dispersing agents, wetting agents and/or suspending agents. Among the acceptable vehicles and solvents that can be used are water, Ringer's solution and isotonic sodium chloride solution. Sterile oils are also conventionally used as solvents or suspending media.

The composition comprising chitosan and/or chitin obtained by the methods of the invention, or a algal extract comprising said chitosan and/or chitin obtained by the methods of the invention, can additionally include conventional excipients, e.g. pharmaceutically acceptable carriers suitable for parenteral application which do not react damaging with the active compounds. Suitable pharmaceutically acceptable vehicles include, for example, water, salt solutions, alcohol, vegetable oils, polyethylene glycols, gelatin, lactose, amylose, magnesium stearate, talc, surfactants, silicic acid, viscous paraffin, perfume oil, monoglycerides and diglycerides of fatty acids, fatty acid esters petroetrals, hydroxymethyl cellulose, polyvinylpyrrolidone and similars. Optional additional ingredients of the composition include diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0, saline solutions, and water.

Several drug delivery systems are known and can be used to administer the agent or composition of the invention, including, for example, encapsulation in liposomes, microbubbles, emulsions, microparticles, microcapsules and similars. The required dosage can be administered as a single unit or in a sustained release form.

Sustainable-release forms and appropriate materials and methods for their preparation are described in, for example, "Modified-Release Drug Delivery Technology", Rathbone, M. J. Hadgraft, J. and Roberts, M. S. (eds.), Marcel Dekker, Inc., New York (2002), "Handbook of Pharmaceutical Controlled Release Technology", Wise, D. L. (ed.), Marcel Dekker, Inc. New York, (2000).

Even though individual needs vary, determination of optimal ranges for effective amounts of chitosan and/or chitin obtained by the methods of the invention, or a algal extract comprising said chitosan and/or chitin obtained by the methods of the invention, belongs to the common experience of those experts in the art. In general, the dosage needed to provide an effective amount of such compound, which can be adjusted by one expert in the art will vary depending on age, health, fitness, sex, diet, weight, degree of alteration, frequency of treatment and the nature and extent of impairment or illness, medical condition of the patient, route of administration, pharmacological considerations such as activity, efficacy, pharmacokinetic and toxicology profile of the particular compound used, if using a system drug delivery, and if the compound is administered as part of a combination of drugs.

In a particular embodiment, the pharmaceutical composition comprises between 0.1% and 5% by weight of the chitosan and/or the chitin obtained by the methods of the invention or the algal extract comprising said chitosan and/or chitin obtained by the methods of the invention.

7. Use of the Chitosan and/or Chitin Obtained by the Methods of the Invention

The chitosan, the chitin, or the combination thereof obtained by the methods of the invention for the production of chitosan, chitin or combinations thereof according to the invention and described above, as well as the algal, preferably microalgal, extract comprising said chitosan and/or chitin, may be useful in many applications, including medical, pharmaceutical and cosmetic applications. Thus, in a further aspect, the invention relates to the use of the chitosan, the chitin, or combinations thereof obtained according to the method for the production of chitosan, chitin, or combinations thereof of the invention as described above, or of the algal, preferably microalgal, extract comprising said chitosan, chitin or combinations thereof obtained according to the methods of the invention, as an anti-acne agent, an anti-inflammatory agent, an anti-irritant agent, an anti-microbial agent, an anti-oxidant agent, an anti-tumor agent, a conditioning agent, a drug delivery agent, a fat-absorption blocking agent, a film-forming agent, a hypocholesterolemic agent, an immunostimulating agent, a lubricant agent, a wetting agent, a wound healing agent, a dermal filler agent, a material for breast implants or a plant growth promoter agent.

Alternatively, the invention relates to the chitosan, the chitin, or combinations thereof obtained according to the methods of the invention, as well as to the algal, preferably microalgal, extract comprising said chitosan and/or chitin obtained according to the methods of the invention, for use as an anti-acne agent, an anti-inflammatory agent, an anti-irritant agent, an anti-microbial agent, an anti-oxidant agent, an anti-tumor agent, a conditioning agent, a drug delivery agent, a fat-absorption blocking agent, a film-forming agent, a hypocholesterolemic agent, an immunostimulating agent, a lubricant agent, a wetting agent, a wound healing agent, a dermal filler agent, a material for breast implants or a plant growth promoter agent.

Anti-acne agents, when topically administered at the site of acne comedomes or microcomedomes, lead to a visible reduction of symptoms associated with the epithelial condition of acne vulgaris.

Anti-inflammatory agents reduce acute and/or chronic inflammatory responses, and are useful in preventing or treating an inflammatory-related disease.

Anti-irritant agents prevent or reduce soreness, roughness, or inflammation of a bodily part (e.g., skin).

Antimicrobial agents are agents capable of killing microorganisms and/or inhibiting their growth.

Anti-oxidant agents inhibit oxidation or reactions promoted by oxygen or peroxides or other free radicals and/or free radical intermediates.

Anti-tumor agents are compounds with antiproliferative, antioncogenic and/or carcinostatic properties which can be used to inhibit tumor growth, proliferation and/or development. Depending on whether or not they can spread by invasion and metastasis, tumours are classified as being either benign or malignant: benign tumours are tumours that cannot spread by invasion or metastasis, i.e., they only grow locally; whereas malignant tumours are tumours that are capable of spreading by invasion and metastasis.

Conditioning agents are compounds useful in conditioning, e.g. hair conditioning agents suitable for use in hair conditioning and that improve the condition of hair.

Drug delivery agents are those agents that target a pharmaceutical compound in the body where appropriate to safely achieve its therapeutic effect.

Fat-absorption blocking agents, or fat-absorption inhibitors, are agents that block the absorption of dietary fat in the gastrointestinal tract of a subject.

Film-forming agents, also known as film formers, are compounds (generally polymers or resins) that leave a film on the substrate to which they are applied, for example, after a solvent accompanying the film former has evaporated, absorbed into and/or dissipated on the substrate.

Hypocholesterolemic agents, also known as hypolipemic agents, reduce cholesterol levels in those subjects with hypercholesterolemia, reducing the risk of a cardiovascular disease.

Immunostimulating agents, also known as immunostimulants, immunoaetivators, immunoaeeelerators or adjuvants, are agents stimulating the innate immune response.

Lubricant agents reduce the friction between surfaces in mutual contact, reducing the heat generated when the surfaces move.

Wetting agents, also known as dispersing agents, promote the proper wetting of a hydrophobic material, e.g., by lowering the interfacial tension and contact angle between solid particles and liquid vehicle.

Wound healing agents are those agents that promote organ or tissue (e.g. skin) repair by itself after injury, involving sequential steps of hemostasis, inflammation, proliferation and remodeling.

Dermal filler agents are agents that promote soft-tissue long-lasting augmentation, addressing certain signs of facial aging by filling soft-tissue defects caused by age, scar formation or disease.

Materials for breast implants are related to prosthesis used to change the size, shape, and contour of a woman's breast. In reconstructive plastic surgery, breast implants can be placed to restore a natural looking breast mound for post-mastectomy breast reconstruction patients or to correct congenital defects and deformities of the chest wall. They are also used cosmetically to enhance or enlarge the appearance of the breast through breast augmentation surgery.

Agents promoting plant growth are agents aimed at enhancing growth in plants, including fertilizers.

Additional uses of the chitin and/or the chitosan obtained according to the method of the invention, as well as of the algal, preferably microalgal, extract comprising said chitin and/or chitosan, include other well-known uses of chitin and of chitosan as described, without limitation, in Cheba B A 2011 Global J. Biotech. Biochem. 6(3): 149-153, Rinaudo M 2006 Prog. Polym. Sci. 31: 603-632, Dutta P K et al. 2004 J. Sci. Ind. Res. 63: 20-31, Xia W 2011 Food Hydrocolloids 25: 170-179, and Dai T et al. 2011 Expert Rev. Anti. Infect. Ther. 9(7): 857-879, and that include waste water treatment, agrochemical uses, environmental uses, textile uses and industrial uses.

Further uses of chitosan obtained according to the first method of the invention, as well as of the algal, preferably microalgal, extract comprising said chitosan include additional well-known uses as follows and described in Miranda et al. (Miranda C et al. 2012, http://dx.doi.org/10.5772/51200), Yogeshkumar et al. (Yogeshkumar G et al. 2013 Int J Res Pharm Biomed Sci 4(1): 312-331), Marques M et al. (Marques M et al. 2011 Aesthetic Surg J 31(5): 540-55); Ma X et al. (Ma X et al. 2014 J Matter Chem B 2: 2749-2763), WO 2015092030 A1, and Ito M et al. (Ito M et al. 2000 Jpn H Pharmacol 82:218-225):

Therapeutic application including, without limitation, wound healing/coagulation, medical devices (including, without limitation, resorbable sutures), blood cholesterol control, anti-tumoral agent, skin burns treatment, artificial skin, contact lenses, drug delivery and released control, bone/cartilague treatment, neuroprotection, anti-inflammatory, injectable medical devices (including, without limitation, dermal fillers), preservation of male fertility, dentistry (moist wound healing, coagulation, dental implants, dental plaque inhibition, toothpaste and chewing gums), anti-microbial, gene therapy, analgesic, peripheral nerve prosthesis, kidney function modulator, immunomodulatory, and vaccine adjuvant, Nutritional application including, without limitation, fat-blockers, encapsulation of nutraceuticals, infant feed ingredient, antigastritis agent and anti-ulcer, Biotechnological applications including, without limitation, enzyme immobilization, Cosmetical applications including, without limitation, face, hand and body creams, hair treatment, moisturizers, antimicrobial, and anti-acne, Animal nutrition including, without limitation, livestock and fish feed additive, Food industry including, without limitation, removal of dyes, solids and acids, preservatives, colour stabilization, controlled moisture transfer between food and surrounding environment, controlled release of antimicrobial substances, reduction of oxygen partial pressure Application in agriculture including, without limitation, seed coating, leaf coating, soil conditioner, hydroponic fertilizer, controlled agrochemical release, pest management, growth promoter, plant self-defence, increase germination and sprouting, and frost protection, Applications in material science including, without limitation, fiber and textile materials, bioplastics, biofoams, and paper industry, Water treatment applications including, without limitation, removal of metal ions, flocculation/coagulation, water filtration and elimination if dyes, proteins and aminoacids.

Therefore, the chitosan obtained by the method for the obtention of chitosan of the invention described above, as well as the algal, preferably microalgal, extract comprising said chitosan may be useful in many medical applications, including wound healing/coagulation, blood cholesterol control, anti-tumoral agent, skin burns treatment, artificial skin, contact lenses, drug delivery and released control, bone/cartilague treatment, neuroprotection, anti-inflammatory, injectable medical devices (including, without limitation, dermal fillers), preservation of male fertility, dentistry (moist wound healing, coagulation, dental implants, dental plaque inhibition, toothpaste and chewing gums), anti-microbial, gene therapy, analgesic, peripheral nerve prosthesis, kidney function modulator, immunomodulatory, and vaccine adjuvant. Thus, in a further aspect, the invention relates to the chitosan obtained by the method for the obtention of chitosan of the invention described above, as well as the algal, preferably microalgal, extract comprising said chitosan, for use in the prevention and/or treatment of wound healing, coagulation, blood cholesterol levels, skin burns, skin damage, bone/cartilague disease, inflammation, male infertility, moist wound healing, coagulation, dental plaque, microbial infection, pain, kidney diseases, and immunomodulation. Alternatively, the invention relates to the use of chitosan obtained by the method for the obtention of chitosan of the invention described above, as well as the algal, preferably microalgal, extract comprising said chitosan, for manufacturing a medicament useful in the treatment and/or prevention of wound healing/coagulation, blood cholesterol levels, skin burns, skin damage, bone/cartilague disease, inflammation, male infertility, moist wound healing, coagulation, dental plaque, microbial infection, pain, kidney diseases, and immunomodulation. Alternatively, the invention relates to a method for the prevention and/or treatment of wound healing/coagulation, blood cholesterol levels, skin burns, skin damage, bone/cartilague disease, inflammation, male infertility, moist wound healing, coagulation, dental plaque, microbial infection, pain, kidney diseases, and immunomodulation in a subject in need thereof that comprises administering to said subject a therapeutically effective amount of chitosan obtained by the method for the obtention of chitosan of the invention described above, or the algal, preferably microalgal, extract comprising said chitosan. As indicated previously, the chitosan, the chitin, or combinations thereof obtained by the methods of the invention described above, as well as the algal, preferably microalgal, extract comprising said chitosan and/or chitin, may be useful in many applications, including medical applications such as anti-tumor agent. Thus, in a further aspect, the invention relates to the chitosan, the chitin or the combinations thereof obtained by the methods for the production of chitosan, chitin or combinations thereof of the invention, to the algal, preferably microalgal, extract comprising said chitosan and/or chitin for use in the prevention and/or treatment of cancer. Alternatively, the invention relates to the use of the chitosan, chitin, or combinations thereof obtained by the method for the production of chitosan, chitin or combinations thereof of the invention, or of the algal, preferably microalgal, extract comprising said chitosan and/or chitin for manufacturing a medicament useful in the treatment of cancer in a subject. Alternatively, the invention relates to a method for the prevention and/or treatment of cancer in a subject in need thereof that comprises administering to said subject a therapeutically effective amount of the chitosan, the chitin or combinations thereof obtained by the method for the production of chitosan, chitin or combinations thereof of the invention, or of the algal, preferably microalgal, extract comprising said chitosan and/or chitin.

The term "cancer" relates to a disease characterized by uncontrolled cell division (or by an increase of survival or apoptosis resistance), by the ability of said cells to invade other neighbouring tissues (invasion) or by the spread to other areas of the body where the cells are not normally located (metastasis) through the lymphatic and blood vessels. As used herein, the term cancer includes, but is not limited to, the following types of cancer: breast cancer; biliary tract cancer; bladder cancer; brain cancer including glioblastomas and medulloblastomas; cervical cancer; choriocarcinoma; colon cancer; endometrial cancer; esophageal cancer; gastrointestinal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodglun's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will-be known to one of ordinary skill in the art.

The term "prevention" relates to the capacity to prevent, minimize or hinder the onset or development of a disease or condition, in particular cancer, before its onset.

The term "subject" relates to any subject, particularly a mammalian subject, for whom therapy is desired. Mammalian subjects include humans, domestic animals, farm animals, and zoo, sports, or pet animals such as dogs, cats, guinea pigs, rabbits, rats, mice, horses, cattle, cows, and so on. In a preferred embodiment of the invention, the subject is a mammal. In a more preferred embodiment of the invention, the subject is a human.

The term "therapeutically effective amount", as used herein in relation to the compound for use according to the invention (i.e., chitin and/or chitosan obtained by the method of the invention, or the microalgal extract comprising said chitin and/or chitosan), relates to an amount of said compound that provides the desired effect, for example, an appreciable prevention, cure, delay, reduction of severity or amelioration of one or more symptoms derived from a disease, in particular cancer. The therapeutically effective amount of a compound will be generally determined by taking into consideration different features such, for example, the characteristics of the product itself and the therapeutic effect to be achieved, the particulars of the subject to be treated, the severity of the injury suffered by said subject, the chosen dosage form, etc. In an embodiment, the therapeutically effective amount of the compound is an amount that ameliorates, attenuates or eliminates one or more symptoms of cancer in the treated subject.

Even though individual needs vary, determination of optimal ranges for therapeutically effective amounts of the compounds for use according to the invention belongs to the common experience of those experts in the art. In general, the dosage needed to provide an effective treatment, which can be adjusted by one expert in the art, will vary depending on age, health, fitness, sex, diet, weight, degree of alteration of the receptor, frequency of treatment, nature and condition of the injury, nature and extent of impairment or illness, medical condition of the subject, route of administration, pharmacological considerations such as activity, efficacy, pharmacokinetic and toxicology profile of the particular compound used, if using a system drug delivery, and if the compound is administered as part of a combination of drugs. The amount of the compound for use according to the invention that is therapeutically effective in the prevention and/or treatment of cancer in a subject can be determined by conventional clinical techniques (see, for example, The Physician's Desk Reference, Medical Economics Company, Inc., Oradell, N.J., 1995, and Drug Facts and Comparisons, Inc., St. Louis, Mo., 1993).

The term "treatment" relates to both therapeutic measures and prophylactic or preventive measures, wherein the object is to prevent or slow down (lessen) an undesired physiological change or disorder, such as cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

8. Microalgae for the Production of Chitosan and/or Chitin and Uses Thereof

In a further aspect, the invention relates to the use of an alga for the production of chitosan, chitin, or a combination thereof.

Thus, in a further aspect, the invention relates to the use of an alga for the production of chitosan wherein said alga is selected from chitosan producing algae belonging to the phylum Haptophyta, to the phylum Chlorophyta, or to the phylum Heterokontophyta.

In a further aspect, the invention relates to the use of an alga for the production of chitin wherein said alga is selected from chitin producing algae belonging to the phylum Chlorophyta. In a particular embodiment, the algal biomass is disrupted before recovering the algal extract comprising chitin.

In a further aspect, the invention relates to the use of an alga for the production of a composition comprising chitin and chitosan wherein said alga is selected from chitin and chitosan producing algae belonging to the phylum Chlorophyta. In a particular embodiment, the algal biomass is disrupted before recovering the algal extract comprising chitin and chitosan.

Algae belonging to the phylum Haptophyta, to the phylum Chlorophyta, and to the phylum Heterokontophyta according to the present invention have been described above in the context of the methods of the invention and incorporated herein, In particular, the algae belonging to the phylum Haptophyta are selected from algae belonging to the Prymnesiophyceae class or to the Pavlovophyceae class, the algae belonging to the phylum Chlorophyta are selected from algae belonging to the Trebouxiophyceae class, to the Chlorophyceae class, or to the Chlorodendrophyceae class, and the algae belonging to the phylum Heterokontophyta are selected from algae belonging to the Coscinodiscophyceae class, to the Eustigmatophyceae class, or to the Labyrinthulomycetes class.

More in particular, the algae belonging to the Prymnesiophyceae class are selected from algae belonging to the Isochrysidales order, the algae belonging to the Pavlovophyceae class are selected from algae belonging to the Pavlovales order, the algae belonging to the Trebouxiophyceae class are selected from algae belonging to the Chlorellales order, the algae belonging to the Chlorophyceae class are selected from algae belonging to the Sphaeropleales order or to the Chlamydomonadales order, the algae belonging to the Chlorodendrophyceae class are selected from algae belonging to the Chlorodendrales order, the algae belonging to the Coscinodiscophyceae class are selected from algae belonging to Thalassiosirales order, the algae belonging to the Eustigmatophyceae class are selected from algae belonging to Eustigmatales order, and the algae belonging to the Labyrinthulomycetes class are selected from algae belonging to Labyrinthulales order.

More in particular, the algae belonging to the Isochrysidales order are selected from algae belonging to the Isochrysidaceae family or to the Noelaerhabdaceae family, the algae belonging to the Pavlovales order are selected from algae belonging to the Pavlovaceae family, the algae belonging to the Chlorellales order are selected from algae belonging to the Chlorellaceae family, the algae belonging to the Sphaeropleales order are selected from algae belonging to the Scenedesmaceae family, to the Neochloridaceae family, to the Bracteacoccaceae family, or to the Selenastraeeae family, the algae belonging to the Chlamydomonadales order are selected from algae belonging to the Dunaliellaceae family, to the Haematococcaceae family, to the Palmellopsidaceae family, or to the Chlorococcaceae family, the algae belonging to the Chlorodendrales order are selected from algae belonging to the Chlorodendraceae family, the algae belonging to the Thalassiosirales order are selected from algae belonging to the Thalassiosiraceae family or to the Skeletonemaceae family, the algae belonging to the Eustigmatales order are selected from algae belonging to the Eustigmataceae family, and the algae belonging to the Labyrinthulales order are selected from algae belonging to the Thraustochytriceae family or to the Labyrinthulale family.

Even more in particular, the algae belonging to Isochrysidaceae family are selected from algae belonging to the *Isochrysis* genus or to the *Tisochrysis* genus, the algae belonging to Noelaerhabdaceae family are selected from algae belonging to the *Emiliania* genus, the algae belonging to the Pavlovaceae family are selected from algae belonging to the *Pavlova* genus, the algae belonging to Chlorellaceae family are selected from algae belonging to the *Chlorella* genus, to the *Helicosporidium* genus, to the *Chlorella* genus, to the *Muriella* genus, to the *Protothecca* genus, to the *Nannochloris* genus, or to the *Micractinium* genus, algaealgaethe algae belonging to Scenedesmaceae family are selected from algae belonging to the *Scenedesmus* genus, to the *Desmodesmus* genus, or to the *Coelastrella* genus, the algae belonging to the Neochloridaceae family are selected from algae belonging to the *Neochloris* genus, the algae belonging to the Bracteacoccaceae family are selected from algae belonging to the *Bracteacoccus* genus, the algae belonging to the Selenastraceae family are selected from algae belonging to the *Ankistrodesmus* genus, the algae belonging to Dunaliellaceae family are selected from algae belonging to the *Dunaliella* genus, the algae belonging to Haematococcaceae family are selected from algae belonging to the *Haematococcus* genus, the algae belonging to the Palmellopsidaceae family are selected from algae belonging to the *Chlamydocapsa* genus, the algae belonging to Chlorococcaceae family are selected from algae belonging to the *Chlorococcum* genus, the algae belonging to Chlorodendraceae family are selected from algae belonging to the *Tetraselmis* genus, the algae belonging to Thalassiosiraceae family are selected from algae belonging to the *Thalassiosira* genus, the algae belonging to Skeletonemaceae family are selected from algae belonging to the *Skeletonema* genus, the algae belonging to Eustigmataceae family are selected from algae belonging to the *Nannochloropsis* genus, the algae belonging to Thraustochytriceae family are selected from algae belonging to the *Schizochytrium* genus, *Aurantochytrium* genus, *Aplanochytrium* genus, *Oblongichytrium* genus, *Sycyoidochytrium* genus, *Botryochytrium* genus, *Parietichytrium* genus, *Traustochytrium* genus, and *Ulkenia* genus, and the algae belonging to Labyrinthulales family are selected from algae belonging to the *Labyrinthula* genus.

In a particular preferred embodiment, the algae belonging to the *Isochrysis* genus, to the *Tisochrysis* genus, to the *Emiliania* genus, to the *Pavlova* genus, to the *Chlorella* genus, to the *Helicosporidium* genus, to the *Chlorella* genus, to the *Muriella* genus, to the *Protothecca* genus, to the *Nannochloris* genus, to the *Micractinium* genus, to the *Scenedesmus* genus, to the *Desmodesmus* genus, to the *Coelastrella* genus, to the *Neochloris* genus, to the *Bracteacoccus* genus, to the *Ankistrodesmus* genus, to the *Dunaliella* genus, to the *Haematococcus* genus, to the *Chlamydocapsa* genus, to the *Chlorococcum* genus, to the *Tetraselmis* genus, to the *Thalassiosira* genus, to the *Skeletonema* genus, to the *Nannochloropsis* genus, to the *Schizochytrium* genus, to the *Aurantochytrium* genus, to the *Aplanochytrium* genus, to the *Oblongichytrium* genus, to the *Sycyoidochytrium* genus, to the *Botryochytrium* genus, to the *Parietichytrium* genus, to the *Traustochytrium* genus, to the *Ulkenia* genus, or to the *Labyrinthula* genus, is a microalga.

Preferably, the microalga belonging to the *Isochrysis* genus is *Isochrysis galbana*, the microalga belonging to the *Chlorella* genus is *Chlorella saccharophila, Chlorella vulgaris, Chlorella sorokiniana, Chlorella zofingiensis* or *Chlorella* sp., the microalga belonging to the *Scenedesmus* genus is *Scenedesmus* sp. or *Scenedesmus subspicatus*, the microalga belonging to the *Desmodesmus* genus is *Desmodesmus subspicatus*, the microalga belonging to the *Haematococcus* genus is *Haematococcus pluvialis*, the microalga belonging to the *Thalassiosira* genus is *Thalassiosira pseudonana*, and the microalga belonging to the *Nannochloropsis* genus is *Nannochloropsis gaditana*.

According to the invention, both naturally-occuring algae from the phylum Haptophyta, of the phylum Chlorophyta and of the phylum Heterokontophyta as previously described, and genetically modified algae from said phyla are included.

The invention is described in detail below by means of the following examples which are to be construed as merely illustrative and not limitative of the scope of the invention. The work leading to this invention has received funding from the European Union Seventh Framework Programme (FP7/2007-2013) under grant agreement no. 613931.

EXAMPLE 1

Identification of Microalgae Producing Chitin and Chitosan

The authors of the present invention have determined the presence of chitin and of chitosan in significant amounts in microalgae of the class Trebouxiophyceae and of the class Chlorophyceae, as well as chitosan in microalgae of the class Eustigmatophyceae by means of using chitin binding proteins (CBPs) and chitosan affinity proteins (CAPs, Nampally et al. 2012, ad supra). Semi-quantitative determinations carried out by means of the affinity technique indicated that the proportion of chitin and of chitosan in the microalgae identified by the inventors is higher than that in other species that have already been described in the art as producers, such as diatoms (*Thalassiosira pseudonana*) or fungi (*Mucor circinelloides*), respectively.

While previous studies have focused on chitin and chitosan content in the cell wall or the culture medium, the experiments performed by the inventors demonstrate that the chitin and the chitosan produced by green microalgae identified in the present invention are found inside the inner cell wall or in the cytoplasm, the cell membrane or between the cell membrane and the cell wall.

Materials and Methods

Microalgae Culture and Biomass Production

Diatoms of the genera *Chaetoceros* and *Phaeodactylum* are known to not produce chitin, and therefore their biomass was used as a negative control. Since the green microalga *Chlamydomonas reinhardtii* is the most widely studied on a genetic level and there are no indications of chitin or chitosan production, it was also used as a negative control. Biomasses of the fungus zygomycota *Mucor circinelloides* and of the diatom *Thalassiosira pseudonana* were used as positive controls (for chitosan and chitin production, respectively) in biomass together with chitosan obtained from chemical deacetylation (75%) of chitin extracted from shrimp shell (Sigma C3646) (data not shown).

A group of green microalgae representative of the majority genera in the number of species and about which there is no reliable information concerning chitin or chitosan production, were selected for study. The following genera were included: *Haematococcus, Chlorococcum, Bracteacoccus, Isochrysis, Nannochloropsis, Chlorella* and *Scenedesmus*.

The diatoms *Thalassiosira pseudonana, Chaetoceros gracilis* and *Phaeodactylum tricornutum* were cultured in 300 ml of F/2×2 culture medium aerated with 5% $CO_2$ until reaching the stationary phase (8 days). Temperature and light were kept at 25° C. and 50 µmol $m^{-2}s^{-1}$, respectively. The fungus *Mucor circinelloides* was cultured in 120 ml of YPG medium for 5 days to an optical density of 2.44 at 540 nm. Growth conditions were: 28° C. and stirring at 100 rpm.

*Chlamydomonas reinhardtii* was cultured in 470 ml of TAP medium for 9 days until reaching the stationary phase. Growth conditions were 50 µmol m$^{-2}$s$^{-1}$ of light at 25° C.

*Haematococcus pluvialis* was cultured in 300 ml of Kuhl medium for 14 days at 40 µmol m$^{-2}$s$^{-1}$ of light, 25° C. and 5% $CO_2$ until reaching the stationary phase.

*Chlorococcum* sp. was taken to the stationary phase in BBM culture medium aerated with 5% $CO_2$, at 50 µmol m$^{-2}$s$^{-1}$ of light and a temperature of 25° C.

*Bracteacoccus* sp. was cultured in 800 ml of BG11 medium until reaching the stationary phase after 15 days. Growth conditions were 50 µmol m$^{-2}$s$^{-1}$ of light, 25° C. and aeration with 1% $CO_2$.

*Isochrysis galbana* was cultured to the stationary phase in 900 ml of F/2×2 medium for 9 days. Growth conditions were 50 µmol m$^{-2}$s$^{-1}$ of light, 1% $CO_2$, 25° C.

*Nannochloropsis gaditana* was cultured to the stationary phase in a 450 ml culture for 18 days. Growth conditions were 50 µmol m$^{-2}$s$^{-1}$ of light, 1% $CO_2$, 30° C., and a medium particularly optimized for this organism was used.

*Chlorella vulgaris* was cultured in 325 ml of BBM medium for 22 days until reaching the stationary phase. Growth conditions were 50 µmol m$^{-2}$s$^{-1}$ of light, 5% $CO_2$, 25° C.

*Chlorella saccharophila* was cultured in 450 ml of BBM culture medium for 16 days until reaching the stationary phase. Growth conditions were 50 µmol m$^{-2}$s$^{-1}$ of light, 5% $CO_2$ and 25° C.

*Scenedesmus* sp. was cultured in 300 ml of F/2×2 medium at 50 µmol m$^{-2}$s$^{-1}$ of light for 8 days until reaching the stationary phase. The culture was aerated with 5% $CO_2$ and the temperature was kept at 25° C.

Biomass Harvest and Disruption

The biomass of each of the microorganisms was recovered from the liquid culture by centrifuging at 5,000 g for 10 minutes and was then immediately frozen in liquid nitrogen and put away at −80° C. Then part of the biomass was homogenized by pressure using a cell disruptor, subjecting the sample to 2.5 kbars of pressure 5 times. Proper homogenization of the samples was confirmed by optical microscopy.

Chitin and Chitosan Detection

GFP fusion to CBPs and CAPs allows detecting chitin and chitosan, respectively, in the cell wall (intact biomass) and inside the cell (homogenized biomass) by means of fluorescence. CBP-GFP and CAP-GFP were obtained from the laboratory of Prof. Bruno M. Moerschbacher from the University of Munster, Germany (Nampaly et al. 2012 ad supra). The experiment was performed in Nunclon Delta Surface 96-well plates at room temperature. First the samples were incubated in a 2% BSA PBS solution (mass-volume) for 2 hours under stirring at 100 rpm. Then 3 washes were performed with Tween 20 0.05% PBS stirring at 100 rpm for 10 minutes each. Next, the samples were incubated in a solution of 1.6 µM CBP or 1.6 µM CAP in 5% BSA TBS for 1 hour stirring at 100 rpm. Two more washes were performed before the final reading to remove all those proteins that had not specifically bound to chitin or chitosan. All centrifugations between incubations and washes were done in a plate centrifuge at 2700 rpm for 10 minutes. The reading of the fluorescence signal of each of the samples was finally taken with a Biotek FLX800 plate fluorometer equipped with a 485/20 nm excitation filter and a 528/20 nm emission filter.

Results and Discussion

Affinity proteins developed by Nampally et al. were used for this study. Said proteins have been specifically designed by means of directed mutagenesis for specifically detecting chitin (CBPs) and chitosan (CAPs) (Nampally et al. 2012, Fuenzalida J P et al. 2014 Biomacromolecules 15(7): 2532-2539).

A semi-quantitative assessment of the chitin and chitosan content in a number of microalgae species comprising the phyla Chlorophyta and Haptophyta, as well as of the chitin and chitosan-producing fungus *Mucor circinelloides*, was obtained as a result of screening by means of affinity proteins. Table 1 shows the results normalized for screening chitin in both whole biomass and in homogenized biomass. It can be seen that the genera *Chlorella* and *Scenedesmus* belonging to the phyla Chlorophyta have the highest concentration of chitin, followed by the heterokontophyta *Thalassiosira* and the chlorophytes *Bracteacoccus* and *Haematococcus*. Except in heterokontophyta, homogenized biomass has a higher concentration of chitin, indicating that it is mostly found deep inside the cell wall, or inside the cell, embedded in the cell mebrane or between the cell mebrane and the cell wall, and not necessarily fixed to or included homogeneously in the cell wall as occurs in fungi. In the case of the heterokontophyta *Thalassiosira*, chitin fibers are known to emerge from the cell wall, so significant differences cannot be observed between whole and homogenized biomass.

With respect to the presence of chitosan, once again, the chlorophyta of the genera *Chlorella* and *Scenedesmus* have the highest amount of chitosan, and again, within the inner boundaries delimited by the cell wall. A significant amount of chitosan is surprisingly detected in the heterokontophyta *Thalassiosira*, and, as was to be expected, in the fungus used as a positive control *M. circinelloides*. Significant amounts of chitin or chitosan were not found in negative controls (the chlorophyta *C. reinhardtii* and the heterokontophyta *P. tricornutum* and *C. gracilis*), as expected.

EXAMPLE 2

Microalgal Chitin and Chitosan Extraction and Characterization

The inventors confirmed the presence of chiting and chitosan in microalgal cells by using chitin binding proteins and chitosan affinity proteins. In this case the polymers were extracted from the microalgal cell wall and characterized using standard methods for the characterization of chitin and chitosan.

While in previous studies the presence of chitin-like glycans is suggested after detecting the presence of amino-sugars in the cell walls through the use of colorimetric assays or cell wall degradating enzymes, the experiments performed by the inventors demonstrate the presence of chitin and chitosan in microalgae by extracting and characterizing the polymers directly.

In this case, the characterized chitin was obtained from *Desmodesmus subspicatus* AC 139 and the characterized chitosan was obtained from *Chlorella vulgaris* H1993.

Materials and Methods

Microalgae Culture and Biomass Production

*Desmodesmus subspicatus* AC 139 was obtained from the collection of microalgal cultures from the University of Caen Basse-Normandie (Algobank). It was cultured in 0.95 mL of Bold Basal Medium (BBM) to the end of the exponential phase at 50 µmol m$^{-2}$s$^{-1}$ of light. The culture was aerated with 5% $CO_2$ and the temperature was kept at 25° C.

*Chlorella vulgaris* H1993 was obtained from the culture collection of Algae of Charles University (CAUP). It was cultured in 0.95 mL of BBM medium to the stationary phase at 50 μmol m$^{-2}$s$^{-1}$ of light. The culture was aerated with 5% $CO_2$ and the temperature was kept at 25° C.

Biomass Harvest and Disruption

The biomass of each of these microorganisms was recovered from the liquid culture by centrifuging at 5,000 g for 10 minutes and was then immediately frozen in liquid nitrogen and stored at −80° C. Then part of the biomass was homogenized by pressure using a cell disruptor, subjecting the sample to 5 cycles of 2.5 kbars of pressure. Proper homogenization of the samples was confirmed by optical microscopy.

Chitin and Chitosan Extraction

The protocol followed to extract chitin and chitosan from these particular samples consisted first on deproteinizing the disrupted biomass at 2% sodium hydroxide for 2 h at 90° C. Secondly, the solubilisation of the chitosan fraction in 10% acetic acid for 6 hours at 65° C. separates the chitin and chitosan fractions. Thirdly, the chitosan fraction is precipitated with sodium hydroxide. Finally both fractions are washed thoroughly with water, ethanol and acetone and vacuum dried.

Chitin and Chitosan Characterization

Techniques such as Fourier Transform Infra Red spectroscopy (FTIR) and Nuclear Magnetic Resonance spectroscopy (1H-NMR) have been used for the identification of the polymers and the determination of the degree of acetylation (DA). The average molecular weight (MW) and the polidispersity of weights (PI) were determined using Size Exclusion Cromatography (SEC) coupled to a Refractive Index detector (IR) and a Multi-Angle Light Scattering detector (MALS).

For the IR analysis, 1-2 mg of chitin or chitosan samples were ground to a very fine powder with KBr. The mixture was pressed in a mould to form a KBr disc containing the sample. The sample was analysed using a Thermo Nicolet NEXUS 470 FTIR.

For the 1H-NMR analysis, 5 mg of the sample is diluted in deuterium oxide with 1% deuterium chloride at 70° C. for 30 minutes. Then the 1H-NMR was performed in a Bruker 500 Mhz NMR spectrometer at 70° C. and 400 Mhz.

For the SEC-IR-MALS analysis the sample was separated by gel permeation chromatography (Novema® columns from PSS 30 Å, 3000 Å, 3000 Å and guard column; I.D.: 8 mm) and detected with a refractive index detector (Agilent Serie 1200 RID®), a viscometer detector (PSS ETA-2010 differential viscometer®) and multi-angle-laser-light-scattering (PSS SLD 7000 MALLS®) equipped with a 5 mW He/Ne laser operating at _____=632.8 nm. Light intensity measurements were derived following the classical Rayleigh-Debye equation allowing us to deduce the Mw. The dn/dc was deduced from a polynomial based on previous studies that relates the dn/dc with the degree of acetylation. A degassed 0.2 M acetic acid/0.15 M ammonium acetate buffer (pH=4.5) was used as eluent. The flow rate was maintained at 0.6 mL/min.

Results and Discussion

Figure 2:
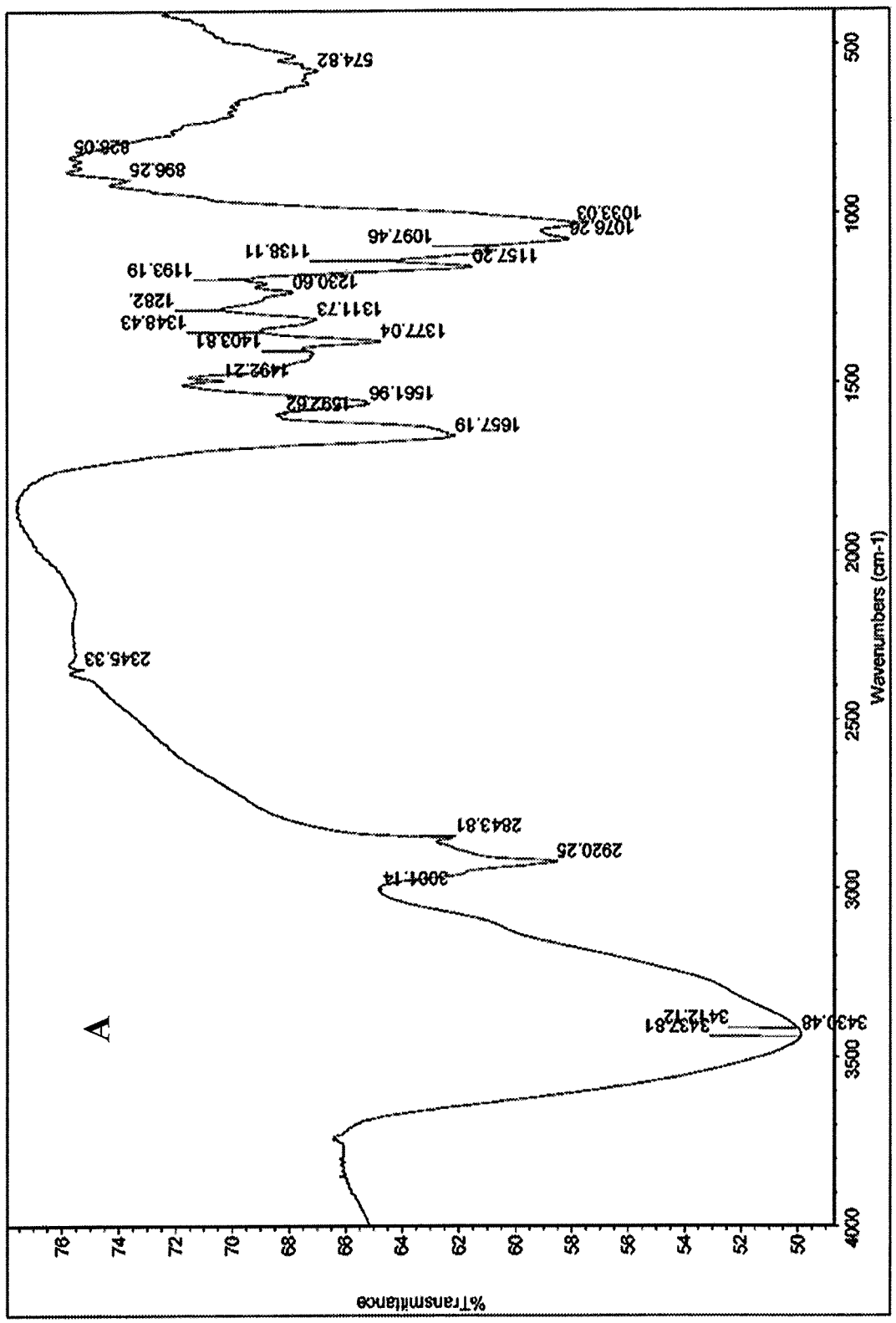
FIG. 2 shows a comparison of the FTIR spectra of a commercially available pure chitin sample from Sigma Aldrich (reference C7170, A) with the insoluble fraction in 10% acetic acid of a disrupted microalgal sample, more in particular the chlorophyta *Desmodesmus subspicatus* AC139 (B). This comparison proves the presence of chitin in a microalgal sample.
Figure 2:
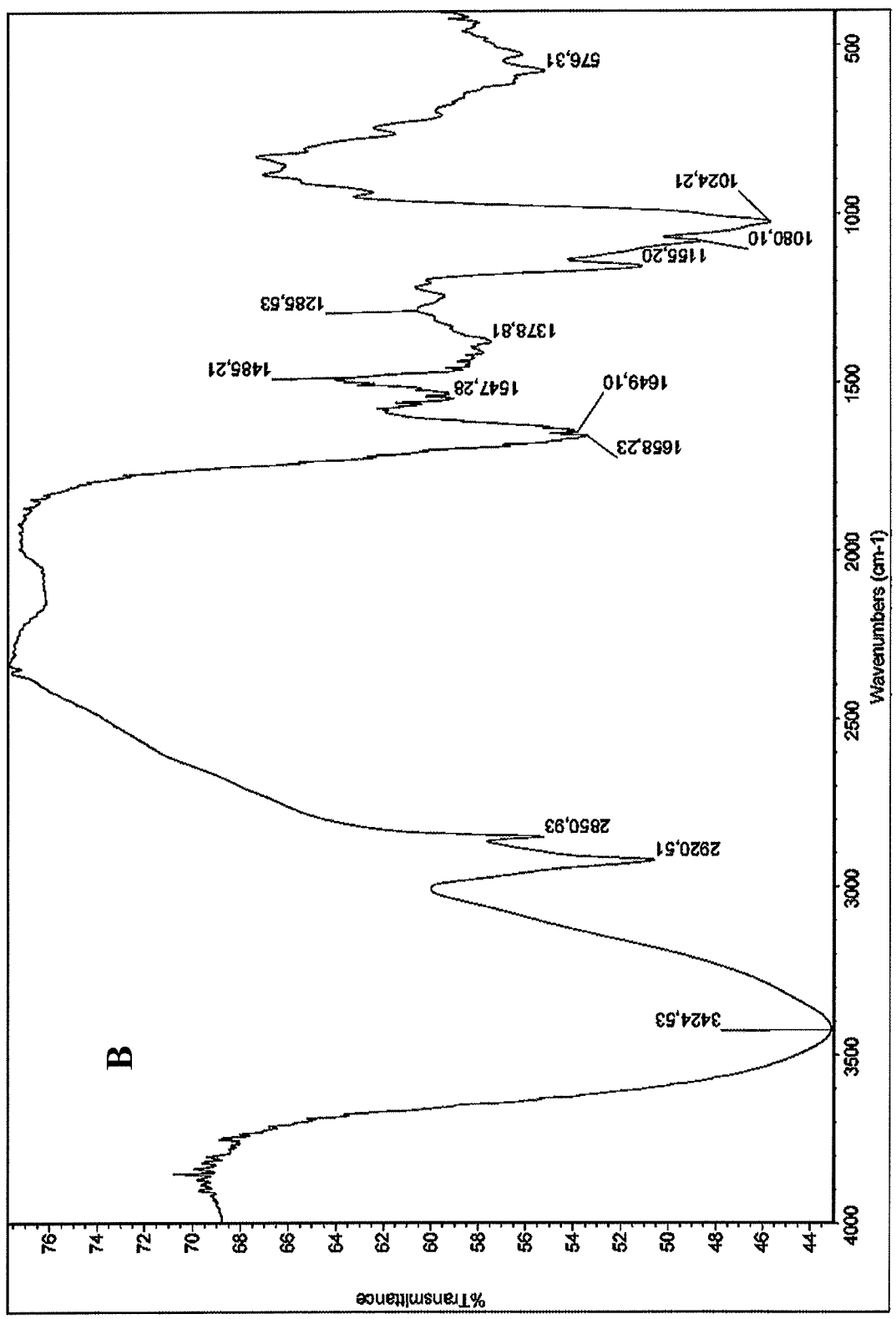

FIG. 2 shows a comparison of the spectrum of pure chitin from Sigma Aldrich reference C7170 (A) and the spectrum of the chitin fraction (insoluble fraction in 10% acetic acid) from *Desmodesmus subspicatus* AC 139 (B). The FTIR shows the representative bands for chitin in both the standard and the microalgal samples.

Figure 3:
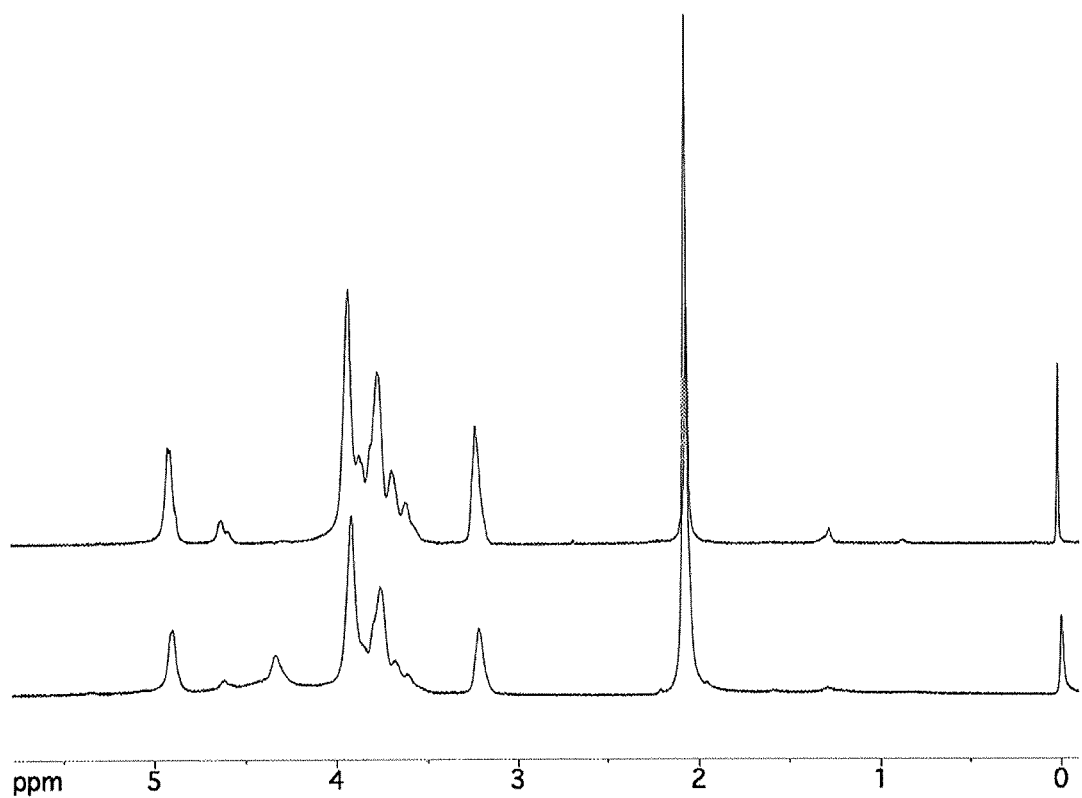
FIG. 3 shows a comparison of the H1-NMR spectra of a commercially available pure chitosan sample 25% acetylated from Sigma Aldrich (reference C3646, top of the figure) with the soluble fraction in 10% acetic acid of a disrupted microalgal sample, more in particular the chlorophyta *Chlorella vulgaris* H1993 (bottom). This comparison shows the presence of chitosan in a microalgal sample.

FIG. 3 shows a comparisson of the H1 NMR espectra from pure chitosan 25% DA from Sigma Aldrich reference C3646 (top) with the chitosan fraction (soluble fraction in 10% acetic acid) from from *Chlorella* vulgaris H1993 (bottom). In order to determine the degree of acetylation the integral values of proton H1 of the deacetylated monomer and of the acetylated monomer were used. Trimethylsilyl propionoc acid (TMSP-d4) was used as internal reference. The degree of acetylation of the chitosan from *Chlorella vulgaris* H1993 was determined to be 25%.

The chitosan from *Chlorella vulgaris* H1993 was further characterized using SEC-MALS-RI to determine the molecular weight, the degree of polymerization and the polidisperity index. The average molecular weight was determined to be 25.3 kDA. The degree of polymerization was determined to be 145. Finally, the polidispersity index was determined to be 1.7.

A further characterization of the chitosan and chitin obtained according to Example 2 is shown in Table 2.

TABLE 2

Characterization of chitin and chitosan

| Species | FTIR (Chitin) | Degree of acetylation (%) (Chitosan) | Molecular weight (kDa) (Chitosan) | Degree of polymerisation (Chitosan) | Polidispersity (Chitosan) |
|---|---|---|---|---|---|
| *Chlorella vulgaris* H193 | yes | 25 | 25.3 | 145 | 1.7 |
| *Desmodesmus subspicatus* AC139 | yes | N.A. | N.A. | N.A. | N.A. |

N.A.—not applicable

TABLE 1

Chitin and chitosan content in analyzed samples. Normalized data (ratios) with respect to autofluorescence of each biomass are shown.

| | Genus | Species | Chitin (whole biomass) | Chitin (homogenated biomass) | Chitosan (whole biomass) | Chitosan (homogenated biomass) |
|---|---|---|---|---|---|---|
| Fungi | Zygomicota (+control) | *Mucor circinelloides* | 2.22 | 1.60 | 6.76 | 5.94 |
| Microalgae | Chlorophyta (−control) | *Chlamydomonas reinhardtii* | 2.56 | 1.92 | 1.86 | 1.55 |
| | Heterokontophyta (+control) | *Thalassiosira pseudonana* | 14.20 | 9.51 | 7.89 | 7.22 |
| | Heterokontophyta (−control) | *Phaeodactylum tricornutum* | 1.61 | 3.11 | 2.20 | 3.77 |
| | | *Chaetoceros gracilis* | 1.74 | 3.34 | 1.84 | 2.13 |
| | Haptophyta | *Isochrysis galbana* | 2.36 | 1.77 | 5.60 | 3.84 |
| | Chlorophyta | *Chlorococcum* sp. | 1.21 | 3.34 | 1.10 | 1.95 |

TABLE 1-continued

Chitin and chitosan content in analyzed samples. Normalized data (ratios) with respect to autofluorescence of each biomass are shown.

| Genus | Species | Chitin (whole biomass) | Chitin (homogenated biomass) | Chitosan (whole biomass) | Chitosan (homogenated biomass) |
|---|---|---|---|---|---|
| | Scenedesmus sp. | 2.11 | 22.57 | 1.64 | 6.22 |
| | Chlorella vulgaris | 2.38 | 15.18 | 10.66 | 34.05 |
| | Haematococcus pluvialis | 2.48 | 9.00 | 1.24 | 2.08 |
| | Bracteacoccus sp. | 2.61 | 10.57 | 1.94 | 2.62 |
| | Chlorella saccharophila | 5.02 | 17.29 | 7.80 | 16.18 |
| Heterokontophyta | Nannochloropsis gaditana | 2.50 | 4.28 | 2.25 | 4.75 |

The invention claimed is:

1. A chitosan characterized by a molecular weight of 15-50 kDa and a degree of acetylation of 7-35%, and further characterized by a degree of polymerization of 50-500, and/or a polydispersity index of less than or equal to 2.0.

2. The chitosan according to claim 1, wherein the chitosan was obtained by a method comprising the steps of:
   (a) culturing the chitosan in a culture by producing an algal biomass under suitable growing conditions for the production of chitosan, and
   (b) recovering an algal extract comprising said chitosan from the culture,
   wherein the algal biomass comprises algae belonging to of a phylum Haptophyta, to a phylum Chlorophytea, or to a phylum Heterokontophyta.

3. The chitosan according to claim 2, wherein the method further comprises a step of disruption of the algal biomass and/or purification of the chitosan from the algal biomass.

4. The chitosan according to claim 2, wherein
   the algae belonging to the phylum Haptophyta are selected from the algae belonging to Prymnesiophyceae class or Pavlovophyceae class,
   the algae belonging to the phylum Chlorophyta are selected from the algae belonging to Trebouxiophyceae class, Chlorophyceae class, or Chlorodendrophyceae class, and
   the algae belonging to the phylum Heterokontophyta are selected from the algae belonging to Coscinodiscophyceae class, Eustigmatophyceae class, or Labyrinthulomycetes class.

5. A composition for food, feed, agricultural, cosmeceutical, cosmetic, nutraceutical or pharmaceuticals, the composition comprising between about 0.1% and about 99.998% by weight of the chitosan according to claim 1.

6. A method for the production of chitosan obtained by a method comprising the steps of:
   (a) culturing a chitosan producing algal biomass in a culture under suitable growing conditions for the production of chitosan, and
   (b) recovering an algal extract comprising said chitosan from the culture,
   wherein the algal biomass comprises algae belonging to of a phylum Haptophyta, to a phylum Chlorophytea, or to a phylum Heterokontophyta, and
   wherein the chitosan is characterized by a molecular weight of 15-50 kDa and a degree of acetylation of 7-35%, and is further characterized by a degree of polymerization of 50-500, and/or a polydispersity index of less than or equal to 2.0.

7. The method according to claim 6 further comprising a step of disruption of the algal biomass and/or purification of the chitosan from the algal biomass.

8. The method according to claim 7, wherein
   the algae belonging to the phylum Haptophyta are selected from the algae belonging to the Prymnesiophyceae class or Pavlovophyceae class,
   the algae belonging to the phylum Chlorophyta are selected from the algae belonging to Trebouxiophyceae class, Chlorophyceae class, or Chlorodendrophyceae class, and
   the algae belonging to the phylum Heterokontophyta are selected from the algae belonging to Coscinodiscophyceae class, Eustigmatophyceae class, or Labyrinthulomycetes class.

9. The method according to claim 8, wherein
   the algae belonging to the Prymnesiophyceae class are selected from algae belonging to the lsochrysidales order,
   the algae belonging to the Pavlovophyceae class are selected from belonging to the Pavlovales order,
   the algae belonging to the Trebouxiphyceae class are selected from algae belonging to the Chlorellales order,
   the algae belonging to the Chlorophyceae class are selected from algae belonging to the Sphaeropleales order or to the Chlamydomonadales order,
   the algae belonging to the Chlorodendrophyceae class are selected from algae belonging to the Chlorodendrales order,
   the algae belonging to the Coscinodiscophyceae class are selected from algae belonging to Thalassiosirales order,
   the algae belonging to the Eustigmatophyceae class are selected from algae belonging to Eustigmatales order, and
   the algae belonging to the Labyrinthulomycetes class are selected from algae belonging to Labyrinthulales order.

10. The method according to claim 9, wherein
    the algae belonging to the lsochrysidales order are selected from algae belonging to the lsochrysidaceae family or to the Noelaerhabdaceae family,
    the algae belonging to the Pavlovales order are selected from algae belonging to the Pavlovaceae family,
    the algae belonging to the Chlorellales order are selected from algae belonging to the Chlorellaceae family,
    the algae belonging to the Sphaeropleales order are selected from algae belonging to the Scenedesmaceae family, to the Neochloridaceae family, to the Bracteacoccaceae family, or to the Selenastraceae family,
    the algae belonging to the Chlamydomonadales order are selected from algae belonging to the Dunaliellaceae family, to the Haematococcaceae family, or to the Palmellopsidaceae family, or to the Chlorococcaceae family, the algae belonging to the Chlorodendrales order are selected from algae belonging to the Chlorodendraceae family, the algae belonging to the Thalassiosirales order are selected from algae belonging to the Thalassiosiraceae family or to the Skeletonemaceae family, the algae belonging to the Eustigmatales order are selected from algae belonging to the Eustigmataceae family, and the algae belonging to the Labyrinthulales order are selected from algae belonging to the Thraustochytriceae family or to the Labyrinthulale family.

11. The method according to claim 10, wherein the algae belonging to lsochrysidaceae family are selected from algae belonging to the *Isochrysis* genus or to the *Tisochrysis* genus, the algae belonging to Noelaerhabdaceae family are selected from algae belonging to the *Emiliania* genus, the algae belonging to the Pavlovaceae family are selected from algae belonging to the *Pavlova* genus, the algae belonging to Chlorellaceae family are selected from algae belonging to the *Chlorella* genus, to the *Helicosporidium* genus, to the *Chlorella* genus, to the *Muriella* genus, to the *Prototheca* genus, to the *Nannochloris* genus, or to the *Micractinium* genus, the algae belonging to Scenedesmaceae family are selected from algae belonging to the *Scenedesmus* genus, to the *Desmodesmus* genus, or to the *Coelastrella* genus, the algae belonging to the Neochloridaceae family are selected from algae belonging to the *Neochloris* genus, the algae belonging to the Bracteacoccaceae family are selected from algae belonging to the *Bracteacoccus* genus, the algae belonging to the Selenastraceae family are selected from algae belonging to the *Ankistrodesmus* genus, the algae belonging to Dunaliellaceae family are selected from algae belonging to the *Dunaliella* genus, the algae belonging to Haematococcaceae family are selected from algae belonging to the *Haematococcus* genus, the algae belonging to the Palmellopsidaceae family are selected from algae belonging to the *Chlamydocapsa* genus, the algae belonging to Chlorococcaceae family are selected from algae belonging to the *Chlorococcum* genus, the algae belonging to Chlorodendraceae family are selected from algae belonging to the *Tetraselmia* genus, the algae belonging to Thalassiosiraceae family are selected from algae belonging to the *Thalassiosira* genus, the algae belonging to Skeletonemaceae family are selected from algae belonging to the *Skeletonema* genus, the algae belonging to Eustigmataceae family are selected from algae belonging to the *Nannochloropsis* genus, the algae belonging to Thraustochytriceae family are selected from algae belonging to the *Schizochytrium* genus, *Aurantochytrium* genus, *Aplanochytrium* genus, *Oblongichytrium* genus, *Sycyoidochytrium* genus, *Botryochytrium* genus, *Parietichytrium* genus, *Traustochytrium* genus, and *Ulkenia* genus, and the algae belonging to Labyrinthulales family are selected from algae belonging to the *Labyrinthula* genus.

12. The method according to claim 11, wherein the alga is a microalga.

13. The method according to claim 12, wherein the microalga belonging to the *Isochrysis* genus is *Isochrysis galbana*, the microalga belonging to the *Chlorella* genus is *Chlorella saccharophila*, *Chlorella vulgaris*, *Chlorella sorokiniana*, *Chlorella zofingiensis* or *Chlorella* sp., the microalga belonging to the *Scenedesmus* genus is *Scenedesmus* sp. or *Scenedesmus* subspicatus, the microalga belonging to the *Desmodesmus* genus is *Desmodesmus* subspicatus, the microalga belonging to the *Haematococcus* genus is *Haematococcus* pluvialis, the microalga belonging to the *Thalassiosira* genus is *Thalassiosira pseudonana*, and the microalga belonging to the *Nannochloropsis* genus is *Nannochloropsis* gaditana.

14. An algal extract comprising chitosan obtained by the method according to claim 6.

* * * * *